(12) United States Patent
Bondanza et al.

(10) Patent No.: US 11,299,529 B2
(45) Date of Patent: Apr. 12, 2022

(54) CHIMERIC ANTIGEN RECEPTORS

(71) Applicant: AGC Biologies S.p.A., Bresso (IT)

(72) Inventors: Attilio Bondanza, Melzo (IT); Monica Casucci, Paullo (IT); Maria Chiara Bonini, Peschiera Borromeo (IT)

(73) Assignee: AGC Biologics S.p.A., Bresso (IT)

(*) Notice: Subject to any disclaimer, the term of this patent is extended or adjusted under 35 U.S.C. 154(b) by 0 days.

(21) Appl. No.: 15/511,026

(22) PCT Filed: Sep. 14, 2015

(86) PCT No.: PCT/IB2015/057049
§ 371 (c)(1),
(2) Date: Mar. 14, 2017

(87) PCT Pub. No.: WO2016/042461
PCT Pub. Date: Mar. 24, 2016

(65) Prior Publication Data
US 2017/0247428 A1 Aug. 31, 2017

Related U.S. Application Data

(63) Continuation of application No. PCT/IB2015/057049, filed on Sep. 14, 2015.

(30) Foreign Application Priority Data

Sep. 15, 2014 (EP) ..................................... 14184838

(51) Int. Cl.
*C07K 14/71* (2006.01)
*C07K 14/705* (2006.01)
*A61K 39/00* (2006.01)
*C07K 14/48* (2006.01)

(52) U.S. Cl.
CPC .... *C07K 14/70585* (2013.01); *A61K 39/0011* (2013.01); *A61K 39/00111* (2018.08); *A61K 39/001106* (2018.08); *A61K 39/001112* (2018.08); *A61K 39/001113* (2018.08); *A61K 39/001124* (2018.08); *A61K 39/001128* (2018.08); *A61K 39/001168* (2018.08); *A61K 39/001182* (2018.08); *A61K 39/001186* (2018.08); *C07K 14/48* (2013.01); *C07K 14/70503* (2013.01); *C07K 14/70521* (2013.01); *C07K 14/70571* (2013.01); *A61K 2039/5158* (2013.01); *C07K 2319/00* (2013.01); *C07K 2319/03* (2013.01)

(58) Field of Classification Search
CPC ........ C07K 14/70585; C07K 14/70503; C07K 14/70578
See application file for complete search history.

(56) References Cited

U.S. PATENT DOCUMENTS

| | | | |
|---|---|---|---|
| 7,563,776 B2 | 7/2009 | Federico | |
| 8,669,350 B2 | 3/2014 | Chou et al. | |
| 2016/0151465 A1* | 6/2016 | Slawin et al. | |

FOREIGN PATENT DOCUMENTS

| | | |
|---|---|---|
| CN | 103145849 A | 6/2013 |
| JP | 2018-536431 A | 12/2018 |
| RU | 2330884 C2 | 8/2008 |
| WO | WO-99/41397 | 8/1999 |
| WO | WO-01/79518 | 10/2001 |
| WO | WO-2004/035768 A1 | 4/2004 |
| WO | WO-2013/153391 A1 | 10/2013 |
| WO | WO-2014/100385 A1 | 6/2014 |
| WO | WO 2014/138704 A1 | 9/2014 |
| WO | WO 2017/062820 A1 | 4/2017 |

OTHER PUBLICATIONS

Rudinger, in Peptide Hormones, ed. J.A. Parsons, University Park Press, Baltimore, pp. 1-7 (1976).*
Altschul et al., Basic local alignment search tool, J. Mol. Biol., 215(3):403-10 (1990).
Armour et al., Differential binding to human FcgammaRIIa and FcgammaRIIb receptors by human IgG wildtype and mutant antibodies, Mol. Immunol., 40(9):585-93 (2003).
Bondanza et al., IL-7 receptor expression identifies suicide gene-modified allospecific CD8+ T cells capable of self-renewal and differentiation into antileukemia effectors, Blood, 117(24):6469-78 (2011).
Bonini et al., Safety of retroviral gene marking with a truncated NGF receptor, Nat. Med., 9(4):367-9 (2003).
Brentjens et al., Genetically targeted T cells eradicate systemic acute lymphoblastic leukemia xenografts, Clin. Cancer Res., 13(18 Pt. 1):5426-35 (2007).
Casucci et al., CD44v6-targeted T cells mediate potent antitumor effects against acute myeloid leukemia and multiple myeloma, Blood, 122(20):3461-72 (2013).
Ciceri et al., Infusion of suicide-gene-engineered donor lymphocytes after family haploidentical haemopoietic stem-cell transplantation for leukaemia (the TK007 trial): a non-randomised phase I-II study, Lancet Oncol., 10(5):489-500 (2009).
Cieri et al., IL-7 and IL-15 instruct the generation of human memory stem T cells from naive precursors, Blood, 121(4):573-84 (2013).
Coffin et al. (eds.), Retroviruses, pp. 758-763, Cold Spring Harbor, NY: Cold Spring Harbor Laboratory Press (1997).
Devereux et al., A comprehensive set of sequence analysis programs for the VAX, Nucleic Acids Res., 12(1 Pt. 1):387-95 (1984).
Di Stasi et al., T lymphocytes coexpressing CCR4 and a chimeric antigen receptor targeting CD30 have improved homing and antitumor activity in a Hodgkin tumor model, Blood, 113(25):6392-402 (2009).

(Continued)

*Primary Examiner* — Robert C Hayes
(74) *Attorney, Agent, or Firm* — Marshall, Gerstein & Borun LLP

(57) ABSTRACT

A chimeric antigen receptor (CAR) comprising an extracellular spacer which comprises at least part of the extracellular domain of human low affinity nerve growth factor (LNGFR) or a derivative thereof.

19 Claims, 50 Drawing Sheets

Specification includes a Sequence Listing.

(56) References Cited

OTHER PUBLICATIONS

Dotti et al., Design and development of therapies using chimeric antigen receptor-expressing T cells, Immunol. Rev., 257(1):107-26 (2014).
Fehse et al., Selective immunoaffinity-based enrichment of CD34+ cells transduced with retroviral vectors containing an intracytoplasmatically truncated version of the human low-affinity nerve growth factor receptor (deltaLNGFR) gene, Hum. Gene Ther., 8(15):1815-24 (1997).
Hombach et al., T cell activation by recombinant FcepsilonRI gamma-chain immune receptors: an extracellular spacer domain impairs antigen-dependent T cell activation but not antigen recognition, Gene Ther., 7(12):1067-75 (2000).
Hsu et al., Differential expression and ligand binding properties of tumor necrosis factor receptor chimeric mutants, J. Biol. Chem., 268(22):16430-6 (1993).
Imai et al., Chimeric receptors with 4-1BB signaling capacity provoke potent cytotoxicity against acute lymphoblastic leukemia, Leukemia, 18(4):676-84 (2004).
International Preliminary Report on Patentability, International Application No. PCT/IB2015/057049, dated Mar. 21, 2017.
International Search Report and Written Opinion, International Application No. PCT/IB2015/057049, dated Dec. 3, 2015.
Kaneko et al., IL-7 and IL-15 allow the generation of suicide gene-modified alloreactive self-renewing central memory human T lymphocytes, Blood, 113(5):1006-15 (2009).
Maher et al., Human T-lymphocyte cytotoxicity and proliferation directed by a single chimeric TCRzeta/CD28 receptor, Nat. Biotechnol., 20(1):70-5 (2002).
Mavilio et al., Peripheral blood lymphocytes as target cells of retroviral vector-mediated gene transfer, Blood, 83(7):1988-97 (1994).
Miller et al., Improved retroviral vectors for gene transfer and expression, Biotechniques, 7(9):980-90 (1989).
Milone et al., Chimeric receptors containing CD137 signal transduction domains mediate enhanced survival of T cells and increased antileukemic efficacy in vivo, Mol. Ther., 17(8):1453-64 (2009).
Pule et al., A chimeric T cell antigen receptor that augments cytokine release and supports clonal expansion of primary human T cells, Mol. Ther., 12(5):933-41 (2005).
Riviere et al., Effects of retroviral vector design on expression of human adenosine deaminase in murine bone marrow transplant recipients engrafted with genetically modified cells, Proc. Natl. Acad. Sci. USA, 92(15):6733-7 (1995).
Sadelain et al., The basic principles of chimeric antigen receptor design, Cancer Discov., 3(4):388-98 (2013).
Shields et al., High resolution mapping of the binding site on human IgG1 for Fc gamma RI, Fc gamma RII, Fc gamma RIII, and FcRn and design of IgG1 variants with improved binding to the Fc gamma R, J. Biol. Chem., 276(9):6591-604 (2001).
Tatusova et al., BLAST 2 Sequences, a new tool for comparing protein and nucleotide sequences, FEMS Microbiol. Lett., 174(2):247-50 (1999).
Verzeletti et al., Herpes simplex virus thymidine kinase gene transfer for controlled graft-versus-host disease and graft-versus-leukemia: clinical follow-up and improved new vectors, Hum. Gene Ther., 9(15):2243-51 (1998).
Yan et al., Disruption of cysteine-rich repeats of the p75 nerve growth factor receptor leads to loss of ligand binding, J. Biol Chem., 266(18):12099-104 (1991).
Rowley et al, 2004 "Phage display for epitope determination: A paradigm for identifying receptor-ligand interactions" Biotechnology Annual Review, vol. 10, pp. 151-188.
Thomis D et al., A Fas-based suicide switch in human T cells for the treatment of graft-versus-host disease, Blood, 2001, vol. 97(5), pp. 1249-1257.
Zhao Y et al., A herceptin-based chimeric antigen receptor with modified signaling domains leads to enhanced survival of transduced T lymphocytes and antitumor activity, Journal of Immunology, 2009, vol. 183, issue 9, pp. 5563-5574.
Casucci et al., Extracellular NGFR Spacers Allow Efficient Tracking and Enrichment of Fully Functional CAR-T Cells Co-Expressing a Suicide Gene, Frontiers in Immunology, Mar. 21, 2018, vol. 9, article 507.
Casucci et al., An innovative CAR-Tcell spacer allowing selection/tracking and enabling superior antitumor effects in vivo, , Human Gene Therapy, Nov. 14, 2014, vol. 25, 11, p. A48, Abstract OR072.
Hornbach et al., Adoptive immunotherapy with genetically engineered T cells: modification of the IgG1 Fc 'spacer' domain in the extracellular moiety of chimeric antigen receptors avoids 'off-target' activation and unintended initiation of an innate immune response, Gene Therapy, Jun. 17, 2010, 17, pp. 1206-1213.
UnitProt Accession No. P08138, TNR16_HUMAN, Sep. 3, 2014, URL: http://uniprot.org/uniprot/P08138,txt?version=163.

* cited by examiner

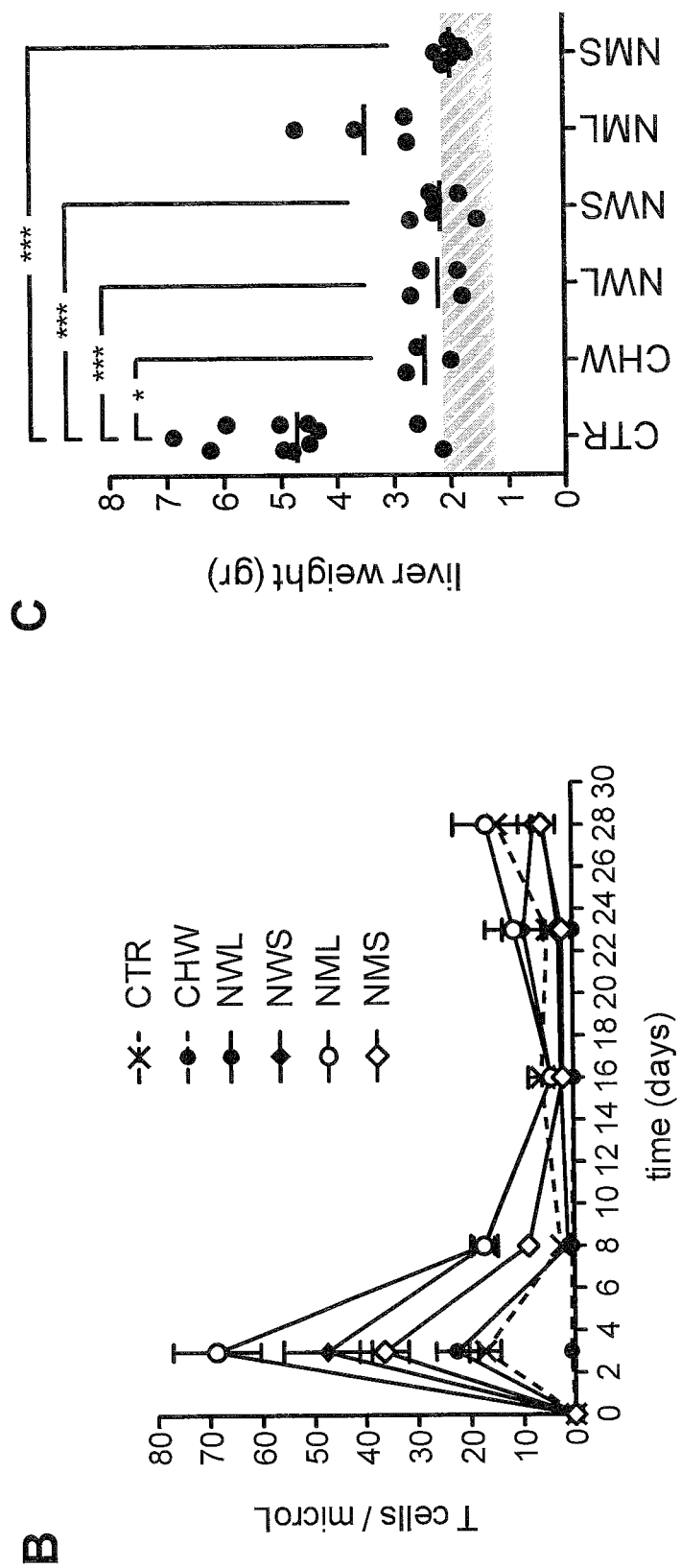
FIG. 6B-C

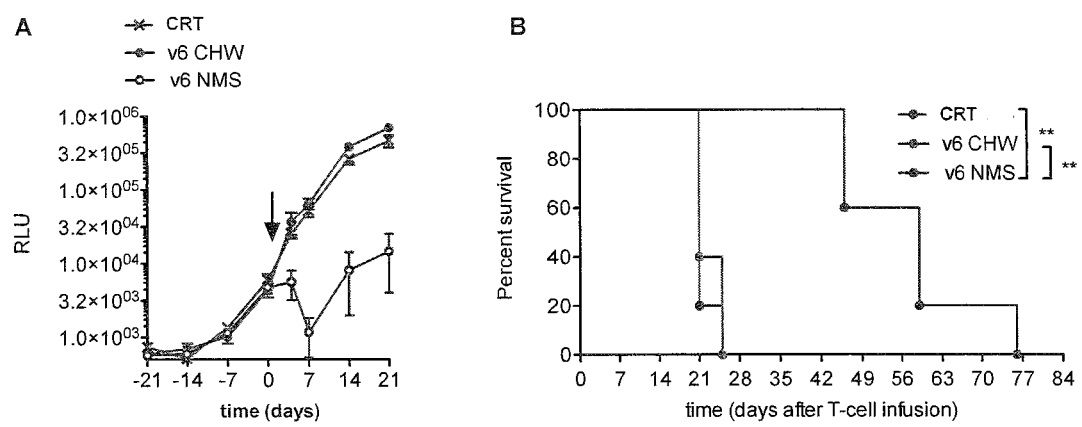
Figure 7BIS

```
        10          20          30          40          50          60
MGAGATGRAM  DGPRLLLLLL  LGVSLGGAKE  ACPTGLYTHS  GECCKACNLG  EGVAQPCGAN 70          80          90         100         110         120
QTVCEPCLDS  VTFSDVVSAT  EPCKPCTECV  GLQSMSAPCV  EADDAVCRCA  YGYYQDETTG 130         140         150         160         170         180
RCEACRVCEA  GSGLVFSCQD  KQNTVCEECP  DGTYSDEANH  VDPCLPCTVC  EDTERQLREC 190         200         210         220         230         240
TRWADAECEE  IPGRWITRST  PPEGSDSTAP  STQEPEAPPE  QDLIASTVAG  VVTTVMGSSQ 250         260         270         280         290         300
PVVTRGTTDN  LIPVYCSILA  AVVVGLVAYI  AFKRWNSCKQ  NKQGANSRPV  NQTPPPEGEK 310         320         330         340         350         360
LHSDSGISVD  SQSLHDQQPH  TQTASGQALK  GDGGLYSSLP  PAKREEVEKL  LNGSAGDTWR 370         380         390         400         410         420
HLAGELGYQP  EHIDSFTHEA  CPVRALLASW  ATQDSATLDA  LLAALRRIQR  ADLVESLCSE

STATSPV
```

FIGURE 8 (SEQ ID NO:14)

FIGURE 9A

CD44v6CAR.28z (SEQ ID NO: 15)

Nucleotides
**ATGGAAGCCCCTGCCCAGCTGCTGTTCCTGCTGCTGCTGTGGCTGCCCGACAC
CACCGGCGAGATCGTGCTGACACAGAGCCCCGCCACCCTGTCTCTGAGCCCTG
GCGAGAGAGCCACCCTGAGCTGTAGCGCCAGCAGCAGCATCAACTACATCTAC
TGGCTGCAGCAGAAGCCCGGCCAGGCCCCCAGAATCCTGATCTACCTGACCAG
CAACCTGGCCAGCGGCGTGCCCGCCAGATTTTCTGGCAGCGGCAGCGGCACCG
ACTTCACCCTGACCATCAGCAGCCTGGAACCCGAGGACTTCGCCGTGTACTAC
TGCCTGCAGTGGTCCAGCAACCCCCTGACCTTCGGCGGAGGCACCAAGGTGGA
AATCAAGCGGGGTGGTGGTGGTTCTGGTGGTGGTGGTTCTGGCGGCGGCGGCT
CCGGTGGTGGTGGATCTGAGGTGCAGCTGGTGGAAAGCGGCGGAGGCCTGGTC
AAGCCTGGCGGCAGCCTGAGACTGAGCTGTGCCGCCAGCGGCTTCACCTTCAG
CAGCTACGACATGAGCTGGGTCCGACAGGCTCCAGGCAAGGGACTGGAATGGG
TGTCCACCATCAGCAGCGGCGGCAGCTACACCTACTACCTGGACAGCATCAAG
GGCCGGTTCACCATCAGCCGGGACAACGCCAAGAACAGCCTGTACCTGCAGAT
GAACAGCCTGCGGGCCGAGGACACCGCCGTCTACTACTGTGCCCGGCAGGGCC
TCGACTACTGGGGCAGAGGCACCCTGGTCACCGTGTC**_CAGCGGGGATCCCGCC
GAGCCCAAATCTCCTGACAAAACTCACACATGCCCACCGTGCCCAGCACCTGA
ACTCCTGGGGGGACGTCAGTCTTCCTCTTCCCCCAAAACCCAAGGACACCC
TCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAA
TGCCAAGACAAAGCCGCGGGAGGAGCAGTACAACAGCACGTACCGTGTGGTCA
GCGTCCTCACCGTCCTGCACCAGGACTGGCTGAATGGCAAGGAGTACAAGTGC
AAGGTCTCCAACAAAGCCCTCCCAGCCCCATCGAGAAAACCATCTCCAAAGC
CAAAGGGCAGCCCCGAGAACCACAGGTGTACACCCTGCCCCCATCCCGGGATG
AGCTGACCAAGAACCAGGTCAGCCTGACCTGCCTGGTCAAAGGCTTCTATCCC
AGCGACATCGCCGTGGAGTGGGAGAGCAATGGGCAACCGGAGAACAACTACAA
GACCACGCCTCCCGTGCTGGACTCCGACGGCTCCTTCTTCCTCTACAGCAAGC
TCACCGTGGACAAGAGCAGGTGGCAGCAGGGGAACGTCTTCTCATGCTCCGTG
ATGCATGAGGCTCTGCACAACCACTACACGCAGAAGAGCCTCTCCCTGTCTCC
GGGTAAAAAAG_**ATCCCAAATTTTGGGTGCTGGTGGTGGTTGGTGGAGTCCTGG
CTTGCTATAGCTTGCTAGTAACAGTGGCCTTTATTATTTTCTGGGTGAGGAGT
AAGAGGAGCAGGCTCCTGCACAGTGACTACATGAACATGACTCCCCGCCGCCC
CGGGCCCACCCGCAAGCATTACCAGCCCTATGCCCCACCACGCGACTTCGCAG
CCT**_ATCGCTCCAGAGTGAAGTTCAGCAGGAGCGCAGACGCCCCGCGTACCAG
CAGGGCCAGAACCAGCTCTATAACGAGCTCAATCTAGGACGAAGAGAGGAGTA
CGATGTTTTGGACAAGAGACGTGGCCGGGACCCTGAGATGGGGGGAAAGCCGA
GAAGGAAGAACCCTCAGGAAGGCCTGTACAATGAACTGCAGAAAGATAAGATG
GCGGAGGCCTACAGTGAGATTGGGATGAAAGGCGAGCGCCGGAGGGGCAAGGG
GCACGATGGCCTTTACCAGGGTCTCAGTACAGCCACCAAGGACACCTACGACG
CCCTTCACATGCAGGCCCTGCCCCCTCGCTAA_

FIGURE 9B

Protein (SEQ ID NO: 16)

**MEAPAQLLFLLLLWLPDTTGEIVLTQSPATLSLSPGERATLSCSASSSINYIY
WLQQKPGQAPRILIYLTSNLASGVPARFSGSGSGTDFTLTISSLEPEDFAVYY
CLQWSSNPLTFGGGTKVEIKRGGGGSGGGGSGGGGSGGGGSEVQLVESGGGLV
KPGGSLRLSCAASGFTFSSYDMSWVRQAPGKGLEWVSTISSGGSYTYYLDSIK
GRFTISRDNAKNSLYLQMNSLRAEDTAVYYCARQGLDYWGRGTLVTVSS**GDPA
EPKSPDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSV
MHEALHNHYTQKSLSLSPGKKDPK**FWVLVVVGGVLACYSLLVTVAFIIFWVRS
KRSRLLHSDYMNMTPRRPGPTRKHYQPYAPPRDFAAYRS**RVKFSRSADAPAYQ
QGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR

Features:
SCFV
*CH2CH3*
CD28
*zeta chain*

FIG. 10 - CD44v6-CAR28z with spacer LNGFR wild-type long (NWL)

Protein sequence

MEAPAQLLFLLLLWLPDTTGEIVLTQSPATLSLSPGERATLSCSASSS
INYIYWLQQKPGQAPRILIYLTSNLASGVPARFSGSGSGTDFTLTISSL
EPEDFAVYYCLQWSSNPLTFGGGTKVEIKRGGGGSGGGGSGGGGS
GGGGSEVQLVESGGGLVKPGGSLRLSCAASGFTFSSYDMSWVRQA
PGKGLEWVSTISSGGSYTYYLDSIKGRFTISRDNAKNSLYLQMNSLRA
EDTAVYYCARQGLDYWGRGTLVTVSS GDP *KEACPTGLYTHSGECCK*
*ACNLGEGVAQPCGANQTVCEPCLDSVTFSDVVSATEPCKPCTECVGL*
*QSMSAPCVEADDAVCRCAYGYYQDETTGRCEACRVCEAGSGLVFSC*
*QDKQNTVCEECPDGTYSDEANHVDPCLPCTVCEDTERQLRECTRWA*
*DAECEEIPGRWITRSTPPEGSDSTAPSTQEPEAPPEQDLIASTVAGVV*
*TTVMGSSQPVVTRGTTDNPK* FWVLVVVGGVLACYSLLVTVAFIIFWVR
SKRSRLLHSDYMNMTPRRPGPTRKHYQPYAPPRDFAAYRS *RVKFSR*
*SADAPAYQQGQNQLYNELNLGRREEYDVLDKRRGRDPEMGGKPQR*
*RKNPQEGLYNELQKDKMAEAYSEIGMKGERRRGKGHDGLYQGLSTA*
*TKDTYDALHMQALPPR*

Legend

CD44v6-specific single-chain fragment

*LNGFR* (sequence taken from the UNIPROT database (P08138, TNR16_HUMAN, position 29-250)

CD28 (sequence taken from the UNIPROT database (P10747, CD28_HUMAN, position 153-220).

*CD3 zeta-chain* (sequence taken from the UNIPROT database (P20963, CD3Z_HUMAN, position 31-143)

FIG. 11 - CD44v6-CAR28z with spacer LNGFR wild-type short (NWS)

Protein sequence

MEAPAQLLFLLLLWLPDTTGEIVLTQSPATLSLSPGERATLSCSASSS
INYIYWLQQKPGQAPRILIYLTSNLASGVPARFSGSGSGTDFTLTISSL
EPEDFAVYYCLQWSSNPLTFGGGTKVEIKRGGGGSGGGGSGGGGS
GGGGSEVQLVESGGGLVKPGGSLRLSCAASGFTFSSYDMSWVRQA
PGKGLEWVSTISSGGSYTYYLDSIKGRFTISRDNAKNSLYLQMNSLRA
EDTAVYYCARQGLDYWGRGTLVTVSSGDP*KEACPTGLYTHSGECCK*
*ACNLGEGVAQPCGANQTVCEPCLDSVTFSDVVSATEPCKPCTECVGL*
*QSMSAPCVEADDAVCRCAYGYYQDETTGRCEACRVCEAGSGLVFSC*
*QDKQNTVCEECPDGTYSDEANHVDPCLPCTVCEDTERQLRECTRWA*
*DAECEEP*KFWVLVVVGGVLACYSLLVTVAFIIFWVRSKRSRLLHSDY
MNMTPRRPGPTRKHYQPYAPPRDFAAYRS*RVKFSRSADAPAYQQG*
*QNQLYNELNLGRREEYDVLDKRRGRDPEMGGKPQRRKNPQEGLYNE*
*LQKDKMAEAYSEIGMKGERRRGKGHDGLYQGLSTATKDTYDALHMQ*
*ALPPR*

Legend

CD44v6-specific single-chain fragment

*LNGFR* (sequence taken from the UNIPROT database (P08138, TNR16_HUMAN, position 29-190).

CD28 (sequence taken from the UNIPROT database (P10747, CD28_HUMAN, position 153-220).

*CD3 zeta-chain* (sequence taken from the UNIPROT database (P20963, CD3Z_HUMAN, position 31-143)

FIG. 12 - CD44v6-CAR28z with spacer LNGFR mutated long (NML)

Protein sequence

MEAPAQLLFLLLLWLPDTTGEIVLTQSPATLSLSPGERATLSCSASSS
INYIYWLQQKPGQAPRILIYLTSNLASGVPARFSGSGSGTDFTLTISSL
EPEDFAVYYCLQWSSNPLTFGGGTKVEIKRGGGGSGGGGSGGGGS
GGGGSEVQLVESGGGLVKPGGSLRLSCAASGFTFSSYDMSWVRQA
PGKGLEWVSTISSGGSYTYYLDSIKGRFTISRDNAKNSLYLQMNSLRA
EDTAVYYCARQGLDYWGRGTLVTVSSGDP*KEACPTGLYTHSGECCK
ACNLGEGVAQPCGANQTVCEPCLDSVTFSDVVSATEPCKPCTECVGL
QSMSAPCVEADDAVCRCAYGYYQDETTGRCEACRVCEAGSGLVFSC
QDKQNTVCEECPDGTYSDEAARAADAECEEIPGRWITRSTPPEGSDS
TAPSTQEPEAPPEQDLIASTVAGVVTTVMGSSQPVVTRGTTDN*PK**FW
VLVVVGGVLACYSLLVTVAFIIFWVRSKRSRLLHSDYMNMTPRRPGP
TRKHYQPYAPPRDFAAYRS***RVKFSRSADAPAYQQGQNQLYNELNLG
RREEYDVLDKRRGRDPEMGGKPQRRKNPQEGLYNELQKDKMAEAYS
EIGMKGERRRGKGHDGLYQGLSTATKDTYDALHMQALPPR*

Legend

CD44v6-specific single-chain fragment

*LNGFR* (sequence taken from the UNIPROT database (P08138, TNR16_HUMAN, position 29-250). Bold: amminoacids that, in the mutated version, has been substituted to the original residues (deleted aa: NHVDPCLPCTVCEDTERQLRECTRW))

CD28 (sequence taken from the UNIPROT database (P10747, CD28_HUMAN, position 153-220).

*CD3 zeta-chain* (sequence taken from the UNIPROT database (P20963, CD3Z_HUMAN, position 31-143)

FIG. 13 - CD44v6-CAR28z with spacer LNGFR mutated short (NMS)

Protein sequence

MEAPAQLLFLLLLWLPDTTGEIVLTQSPATLSLSPGERATLSCSASSS
INYIYWLQQKPGQAPRILIYLTSNLASGVPARFSGSGSGTDFTLTISSL
EPEDFAVYYCLQWSSNPLTFGGGTKVEIKRGGGGSGGGGSGGGGS
GGGGSEVQLVESGGGLVKPGGSLRLSCAASGFTFSSYDMSWVRQA
PGKGLEWVSTISSGGSYTYYLDSIKGRFTISRDNAKNSLYLQMNSLRA
EDTAVYYCARQGLDYWGRGTLVTVSS*GDPKEACPTGLYTHSGECCK*
*ACNLGEGVAQPCGANQTVCEPCLDSVTFSDVVSATEPCKPCTECVGL*
*QSMSAPCVEADDAVCRCAYGYYQDETTGRCEACRVCEAGSGLVFSC*
*QDKQNTVCEECPDGTYSDEAARAADAECEEP*KFWVLVVVGGVLACY
SLLVTVAFIIFWVRSKRSRLLHSDYMNMTPRRPGPTRKHYQPYAPPR
DFAAYRSRVKFSRSADAPAYQQGQNQLYNELNLGRREEYDVLDKRR
GRDPEMGGKPQRRKNPQEGLYNELQKDKMAEAYSEIGMKGERRRG
KGHDGLYQGLSTATKDTYDALHMQALPPR

Legend

CD44v6-specific single-chain fragment

*LNGFR* (sequence taken from the UNIPROT database (P08138, TNR16_HUMAN, position 29-190). Bold: amminoacids that, in the mutated version, has been substituted to the original residues (deleted aa: NHVDPCLPCTVCEDTERQLRECTRW)).

CD28 (sequence taken from the UNIPROT database (P10747, CD28_HUMAN, position 153-220)).

*CD3 zeta-chain* (sequence taken from the UNIPROT database (P20963, CD3Z_HUMAN, position 31-14)

FIG. 14 - CD44v6-CAR28z with spacer LNGFR wild-type long (NWL)

Protein sequence

MEAPAQLLFLLLLWLPDTTGEIVLTQSPATLSLSPGERATLSCSASSS
INYIYWLQQKPGQAPRILIYLTSNLASGVPARFSGSGSGTDFTLTISSL
EPEDFAVYYCLQWSSNPLTFGGGTKVEIKRGGGGSGGGGSGGGGS
GGGGSEVQLVESGGGLVKPGGSLRLSCAASGFTFSSYDMSWVRQA
PGKGLEWVSTISSGGSYTYYLDSIKGRFTISRDNAKNSLYLQMNSLRA
EDTAVYYCARQGLDYWGRGTLVTVSSGDP*KEACPTGLYTHSGECCK*
*ACNLGEGVAQPCGANQTVCEPCLDSVTFSDVVSATEPCKPCTECVGL*
*QSMSAPCVEADDAVCRCAYGYYQDETTGRCEACRVCEAGSGLVFSC*
*QDKQNTVCEECPDGTYSDEANHVDPCLPCTVCEDTERQLRECTRWA*
*DAECEEIPGRWITRSTPPEGSDSTAPSTQEPEAPPEQDLIASTVAGVV*
*TTVMGSSQPVVTRGTTDNPK*FWVLVVVGGVLACYSLLVTVAFIIFWVR
SKRSRLLHSDYMNMTPRRPGPTRKHYQPYAPPRDFAAYRS*RVKFSR*
*SADAPAYQQGQNQLYNELNLGRREEYDVLDKRRGRDPEMGGKPRRK*
*NPQEGLYNELQKDKMAEAYSEIGMKGERRRGKGHDGLYQGLSTATK*
*DTYDALHMQALPPR*

Legend

CD44v6-specific single-chain fragment

*LNGFR* (sequence taken from the UNIPROT database (P08138, TNR16_HUMAN, position 29-250)

CD28 (sequence taken from the UNIPROT database (P10747, CD28_HUMAN, position 153-220).

*CD3 zeta-chain* (sequence taken from the UNIPROT database (P20963, CD3Z_HUMAN, position 31-143, without Q at position 80))

FIG. 15 - CD44v6-CAR28z with spacer LNGFR wild-type short (NWS)

Protein sequence

MEAPAQLLFLLLLWLPDTTGEIVLTQSPATLSLSPGERATLSCSASSS
INYIYWLQQKPGQAPRILIYLTSNLASGVPARFSGSGSGTDFTLTISSL
EPEDFAVYYCLQWSSNPLTFGGGTKVEIKRGGGGSGGGGSGGGGS
GGGGSEVQLVESGGGLVKPGGSLRLSCAASGFTFSSYDMSWVRQA
PGKGLEWVSTISSGGSYTYYLDSIKGRFTISRDNAKNSLYLQMNSLRA
EDTAVYYCARQGLDYWGRGTLVTVSSGDP*KEACPTGLYTHSGECCK*
*ACNLGEGVAQPCGANQTVCEPCLDSVTFSDVVSATEPCKPCTECVGL*
*QSMSAPCVEADDAVCRCAYGYYQDETTGRCEACRVCEAGSGLVFSC*
*QDKQNTVCEECPDGTYSDEANHVDPCLPCTVCEDTERQLRECTRWA*
*DAECEE*PK<u>FWVLVVVGGVLACYSLLVTVAFIIFWVRSKRSRLLHSDY</u>
<u>MNMTPRRPGPTRKHYQPYAPPRDFAAYRS</u>*RVKFSRSADAPAYQQG*
*QNQLYNELNLGRREEYDVLDKRRGRDPEMGGKPRRKNPQEGLYNEL*
*QKDKMAEAYSEIGMKGERRRGKGHDGLYQGLSTATKDTYDALHMQA*
*LPPR*

Legend

CD44v6-specific single-chain fragment

*LNGFR* (sequence taken from the UNIPROT database (P08138, TNR16_HUMAN, position 29-190).

<u>CD28</u> (sequence taken from the UNIPROT database (P10747, CD28_HUMAN, position 153-220).

*CD3 zeta-chain* (sequence taken from the UNIPROT database (P20963, CD3Z_HUMAN, position 31-143, without Q at position 80))

FIG. 16 - CD44v6-CAR28z with spacer LNGFR mutated long (NML)

Protein sequence

MEAPAQLLFLLLLWLPDTTGEIVLTQSPATLSLSPGERATLSCSASSS
INYIYWLQQKPGQAPRILIYLTSNLASGVPARFSGSGSGTDFTLTISSL
EPEDFAVYYCLQWSSNPLTFGGGTKVEIKRGGGGSGGGGSGGGGS
GGGGSEVQLVESGGGLVKPGGSLRLSCAASGFTFSSYDMSWVRQA
PGKGLEWVSTISSGGSYTYYLDSIKGRFTISRDNAKNSLYLQMNSLRA
EDTAVYYCARQGLDYWGRGTLVTVSSGDP*KEACPTGLYTHSGECCK*
*ACNLGEGVAQPCGANQTVCEPCLDSVTFSDVVSATEPCKPCTECVGL*
*QSMSAPCVEADDAVCRCAYGYYQDETTGRCEACRVCEAGSGLVFSC*
*QDKQNTVCEECPDGTYSDEAARADAECEEIPGRWITRSTPPEGSDS*
*TAPSTQEPEAPPEQDLIASTVAGVVTTVMGSSQPVVTRGTTDN*PKFW
VLVVVGGVLACYSLLVTVAFIIFWVRSKRSRLLHSDYMNMTPRRPGP
TRKHYQPYAPPRDFAAYRS*RVKFSRSADAPAYQQGQNQLYNELNLG*
*RREEYDVLDKRRGRDPEMGGKPRRKNPQEGLYNELQKDKMAEAYSE*
*IGMKGERRRGKGHDGLYQGLSTATKDTYDALHMQALPPR*

Legend

CD44v6-specific single-chain fragment

*LNGFR* (sequence taken from the UNIPROT database (P08138, TNR16_HUMAN, position 29-250). Bold: amminoacids that, in the mutated version, has been substituted to the original residues (deleted aa: NHVDPCLPCTVCEDTERQLRECTRW))

CD28 (sequence taken from the UNIPROT database (P10747, CD28_HUMAN, position 153-220).

*CD3 zeta-chain* (sequence taken from the UNIPROT database (P20963, CD3Z_HUMAN, position 31-143, without Q at position 80))

FIG. 17 - CD44v6-CAR28z with spacer LNGFR mutated short (NMS)

Protein sequence

MEAPAQLLFLLLLWLPDTTGEIVLTQSPATLSLSPGERATLSCSASSS
INYIYWLQQKPGQAPRILIYLTSNLASGVPARFSGSGSGTDFTLTISSL
EPEDFAVYYCLQWSSNPLTFGGGTKVEIKRGGGGSGGGGSGGGGS
GGGGSEVQLVESGGGLVKPGGSLRLSCAASGFTFSSYDMSWVRQA
PGKGLEWVSTISSGGSYTYYLDSIKGRFTISRDNAKNSLYLQMNSLRA
EDTAVYYCARQGLDYWGRGTLVTVSSGD*PKEACPTGLYTHSGECCK*
*ACNLGEGVAQPCGANQTVCEPCLDSVTFSDVVSATEPCKPCTECVGL*
*QSMSAPCVEADDAVCRCAYGYYQDETTGRCEACRVCEAGSGLVFSC*
*QDKQNTVCEECPDGTYSDEAARAADAECEEP*KFWVLVVVGGVLACY
SLLVTVAFIIFWVRSKRSRLLHSDYMNMTPRRPGPTRKHYQPYAPPR
DFAAYRS*RVKFSRSADAPAYQQGQNQLYNELNLGRREEYDVLDKRR*
*GRDPEMGGKPRRKNPQEGLYNELQKDKMAEAYSEIGMKGERRRGK*
*GHDGLYQGLSTATKDTYDALHMQALPPR*

Legend

CD44v6-specific single-chain fragment

*LNGFR* (sequence taken from the UNIPROT database (P08138, TNR16_HUMAN, position 29-190). Bold: amminoacids that, in the mutated version, has been substituted to the original residues (deleted aa: NHVDPCLPCTVCEDTERQLRECTRW)).

CD28 (sequence taken from the UNIPROT database (P10747, CD28_HUMAN, position 153-220)).

*CD3 zeta-chain* (sequence taken from the UNIPROT database (P20963, CD3Z_HUMAN, position 31-143, without Q at position 80))

Figure 18 - CD44v6-4GS2-CAR28z with spacer LNGFR wild-type long (NWL)

Protein sequence

MEAPAQLLFLLLLWLPDTTGEIVLTQSPATLSLSPGERATLSCSASSSINYIYWLQ
QKPGQAPRILIYLTSNLASGVPARFSGSGSGTDFTLTISSLEPEDFAVYYCLQWSS
NPLTFGGGTKVEIKRGGGGSGGGGSEVQLVESGGGLVKPGGSLRLSCAASGFTF
SSYDMSWVRQAPGKGLEWVSTISSGGSYTYYLDSIKGRFTISRDNAKNSLYLQMN
SLRAEDTAVYYCARQGLDYWGRGTLVTVSSGDP*KEACPTGLYTHSGECCKACNL*
*GEGVAQPCGANQTVCEPCLDSVTFSDVVSATEPCKPCTECVGLQSMSAPCVEAD*
*DAVCRCAYGYYQDETTGRCEACRVCEAGSGLVFSCQDKQNTVCEECPDGTYSDE*
*ANHVDPCLPCTVCEDTERQLRECTRWADAECEEIPGRWITRSTPPEGSDSTAPST*
*QEPEAPPEQDLIASTVAGVVTTVMGSSQPVVTRGTTDN*PKFWVLVVVGGVLACYS
LLVTVAFIIFWVRSKRSRLLHSDYMNMTPRRPGPTRKHYQPYAPPRDFAAYRS*RV*
*KFSRSADAPAYQQGQNQLYNELNLGRREEYDVLDKRRGRDPEMGGKPRRKNPQ*
*EGLYNELQKDKMAEAYSEIGMKGERRRGKGHDGLYQGLSTATKDTYDALHMQAL*
*PPR*

Legend

CD44v6-4GS2: a CD44v6-specific single-chain fragment (SEQ. ID NO 31)

*LNGFR (sequence taken from the UNIPROT database (P08138, TNR16_HUMAN, position 29-250)*

CD28 (sequence taken from the UNIPROT database (P10747, CD28_HUMAN, position 153-220)

*CD3 zeta-chain* (sequence taken from the UNIPROT database (P20963, CD3Z_HUMAN, position 31-143, without Q at position 80)

Figure 19 - CD44v6-4GS2-CAR28z with spacer LNGFR wild-type short (NWS)

Protein sequence

MEAPAQLLFLLLLWLPDTTGEIVLTQSPATLSLSPGERATLSCSASSSINYIYWLQ
QKPGQAPRILIYLTSNLASGVPARFSGSGSGTDFTLTISSLEPEDFAVYYCLQWSS
NPLTFGGGTKVEIKRGGGGSGGGGSEVQLVESGGGLVKPGGSLRLSCAASGFTF
SSYDMSWVRQAPGKGLEWVSTISSGGSYTYYLDSIKGRFTISRDNAKNSLYLQMN
SLRAEDTAVYYCARQGLDYWGRGTLVTVSSGDP<u>KEACPTGLYTHSGECCKACNL
GEGVAQPCGANQTVCEPCLDSVTFSDVVSATEPCKPCTECVGLQSMSAPCVEAD
DAVCRCAYGYYQDETTGRCEACRVCEAGSGLVFSCQDKQNTVCEECPDGTYSDE
ANHVDPCLPCTVCEDTERQLRECTRWADAECEEPK</u>FWVLVVVGGVLACYSLLVT
VAFIIFWVRSKRSRLLHSDYMNMTPRRPGPTRKHYQPYAPPRDFAAYRS*RVKFSR
SADAPAYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQALPPR*

Legend

CD44v6-4GS2: a CD44v6-specific single-chain fragment (SEQ ID NO 31)

<u>LNGFR</u> (sequence taken from the UNIPROT database (P08138, TNR16_HUMAN, position 29-190).

CD28 (sequence taken from the UNIPROT database (P10747, CD28_HUMAN, position 153-220)

*CD3 zeta-chain* (sequence taken from the UNIPROT database (P20963, CD3Z_HUMAN, position 31-143, without Q at position 80)

Figure 20 - CD44v6-4GS2-CAR28z with spacer LNGFR mutated long (NML)

Protein sequence

**MEAPAQLLFLLLLWLPDTTGEIVLTQSPATLSLSPGERATLSCSASSSINYIYWLQ
QKPGQAPRILIYLTSNLASGVPARFSGSGSGTDFTLTISSLEPEDFAVYYCLQWSS
NPLTFGGGTKVEIKRGGGGSGGGGSEVQLVESGGGLVKPGGSLRLSCAASGFTF
SSYDMSWVRQAPGKGLEWVSTISSGGSYTYYLDSIKGRFTISRDNAKNSLYLQMN
SLRAEDTAVYYCARQGLDYWGRGTLVTVSS**GDP*KEACPTGLYTHSGECCKACNL
GEGVAQPCGANQTVCEPCLDSVTFSDVVSATEPCKPCTECVGLQSMSAPCVEAD
DAVCRCAYGYYQDETTGRCEACRVCEAGSGLVFSCQDKQNTVCEECPDGTYSDE
AARA*ADAECEEIPGRWITRSTPPEGSDSTAPSTQEPEAPPEQDLIASTVAGVVTTV
MGSSQPVVTRGTTDNP*K**FWVLVVVGGVLACYSLLVTVAFIIFWVRSKRSRLLHSD
YMNMTPRRPGPTRKHYQPYAPPRDFAAYRS***RVKFSRSADAPAYQQGQNQLYNE
LNLGRREEYDVLDKRRGRDPEMGGKPRRKNPQEGLYNELQKDKMAEAYSEIGM
KGERRRGKGHDGLYQGLSTATKDTYDALHMQALPPR*

<u>Legend</u>

CD44v6-4GS2: a CD44v6-specific single-chain fragment (SEQ ID NO: 31)

*LNGFR* (sequence taken from the UNIPROT database (P08138, TNR16_HUMAN, position 29-250). Bold: amino acids that, in the mutated version, has been substituted to the original residues (deleted aa: NHVDPCLPCTVCEDTERQLRECTRW (SEQ ID NO: 13))

<u>CD28</u> (sequence taken from the UNIPROT database (P10747, CD28_HUMAN, position 153-220).

*CD3 zeta-chain* (sequence taken from the UNIPROT database (P20963, CD3Z_HUMAN, position 31-143, without Q at position 80))

Figure 21 - CD44v6-4GS2-CAR28z with spacer LNGFR mutated short (NMS)

Protein sequence

MEAPAQLLFLLLLWLPDTTGEIVLTQSPATLSLSPGERATLSCSASSSINYIYWLQ QKPGQAPRILIYLTSNLASGVPARFSGSGSGTDFTLTISSLEPEDFAVYYCLQWSS NPLTFGGGTKVEIKRGGGGSGGGGSEVQLVESGGGLVKPGGSLRLSCAASGFTF SSYDMSWVRQAPGKGLEWVSTISSGGSYTYYLDSIKGRFTISRDNAKNSLYLQMN SLRAEDTAVYYCARQGLDYWGRGTLVTVSSGDP*KEACPTGLYTHSGECCKACNL GEGVAQPCGANQTVCEPCLDSVTFSDVVSATEPCKPCTECVGLQSMSAPCVEAD DAVCRCAYGYYQDETTGRCEACRVCEAGSGLVFSCQDKQNTVCEECPDGTYSDE AARAADAECEE*PKFWVLVVVGGVLACYSLLVTVAFIIFWVRSKRSRLLHSDYMNM TPRRPGPTRKHYQPYAPPRDFAAYRS*RVKFSRSADAPAYQQGQNQLYNELNLGR REEYDVLDKRRGRDPEMGGKPRRKNPQEGLYNELQKDKMAEAYSEIGMKGERRR GKGHDGLYQGLSTATKDTYDALHMQALPPR*

Legend

CD44v6-4GS2: a CD44v6-specific single-chain fragment (SEQ ID NO: 31)

*LNGFR* (sequence taken from the UNIPROT database (P08138, TNR16_HUMAN, position 29-190). Bold: amino acids that, in the mutated version, has been substituted to the original residues (deleted aa: NHVDPCLPCTVCEDTERQLRECTRW (SEQ ID NO: 13)).

*CD28* (sequence taken from the UNIPROT database (P10747, CD28_HUMAN, position 153-220).

*CD3 zeta-chain* (sequence taken from the UNIPROT database (P20963, CD3Z_HUMAN, position 31-143, without Q at position 80)

Figure 26A

CD44v6-4GS2-CAR.28Z NGFR WILD TYPE LONG (V6 NWL) dna.gb aagctttgctcttaggagtttcctaatacatcccaaactcaaatatataaagcatttgacttgttctatgccctagg
gggcgggggaagctaagccagcttttttaacatttaaaatgttaattccattttaaatgcacagatgttttatt
tcataagggtttcaatgtgcatgaatgctgcaatattcctgttaccaaagctagtataaataaaaatagataaac
gtggaaattacttagagtttctgtcattaacgtttccttcctcagttgacaacataaatgcgctgctgagcaagcc
agtttgcatctgtcaggatcaatttcccattatgccagtcatattaattactagtcaattagttgattttattttga
catatacatgtgaatgaaagaccccacctgtaggtttggcaagctagcttaagtaacgccattttgcaaggcatg
gaaaaatacataactgagaatagaaaagttcagatcaaggtcaggaacagatggaacagctgaatatgggcc
aaacaggatatctgtggtaagcagttcctgccccggctcagggccaagaacagatggaacagctgaatatggg
ccaaacaggatatctgtggtaagcagttcctgccccggctcagggccaagaacagatggtccccagatgcggtc
cagccctcagcagtttctagagaaccatcagatgtttccagggtgccccaaggacctgaaatgaccctgtgcctt
atttgaactaaccaatcagttcgcttctcgcttctgttcgcgcgcttatgctccccgagctcaataaaagagccca
caacccctcactcggggcgccagtcctccgattgactgagtcgcccgggtacccgtgtatccaataaaccctctt
gcagttgcatccgacttgtggtctcgctgttccttgggagggtctcctctgagtgattgactaccgtcagcgggg
gtctttcatttgggggctcgtccgggatcgggagacccctgcccagggaccaccgacccaccaccgggaggtaa
gctggccagcaacttatctgtgtctgtccgattgtctagtgtctatgactgattttatgcgcctgcgtcggtactagt
tagctaactagctctgtatctggcggacccgtggtggaactgacgagttcggaacacccggccgcaaccctggg
agacgtcccagggacttcgggggccgttttgtggcccgacctgagtcctaaaatcccgatcgtttaggactcttt
ggtgcaccccccttagaggagggatatgtggttctggtaggagacgagaacctaaaacagttcccgcctccgtc
tgaattttgctttcggtttgggaccgaagccgcgccgcgcgtcttgtctgctgcagcatcgttctgtgttgtctctg
tctgactgtgtttctgtatttgtctgaaaatatgggcccgggctagcctgttaccactcccttaagtttgaccttagg
tcactggaaagatgtcgagcggatcgctcacaaccagtcggtagatgtcaagaagagacgttgggttaccttct
gctctgcagaatggccaacctttaacgtcggatggccgcgagacggcacctttaaccgagacctcatcacccag
gttaagatcaaggtcttttcacctggcccgcatggacacccagaccaggtggggtacatcgtgacctgggaagc
cttggcttttgaccccccctccctgggtcaagccctttgtacaccctaagcctccgcctcctcttcctccatccgcccc
gtctctccccttgaacctcctcgttcgaccccgcctcgatcctccctttatccagccctcactccttctctaggcgc
ccccatatggccatatgagatcttatatggggcaccccgccccttgtaaacttccctgaccctgacatgacaag
agttactaacagcccctctctccaagctcacttacaggctctctacttagtccagcacgaagtctggagacctctg
gcggcagcctaccaagaacaactggaccgaccggtggtacctcacccttaccgagtcggcgacacagtgtggg
tccgccgacaccagactaagaacctagaacctcgctggaaaggaccttacacagtcctgctgaccaccccacc
gccctcaaagtagacggcatcgcagcttggatacacgccgcccacgtgaaggctgccgaccccggggtggac

Figure 26B catcctctagactgccatggaagcccctgcccagctgctgttcctgctgctgctgtggctgcccgacaccaccggc
gagatcgtgctgacacagagccccgccaccctgtctctgagccctggcgagagagccaccctgagctgtagcgc
cagcagcagcatcaactacatctactggctgcagcagaagcccggccaggcccccagaatcctgatctacctga
ccagcaacctggccagcggcgtgcccgccagattttctggcagcggcagcggcaccgacttcaccctgaccatc
agcagcctggaacccgaggacttcgccgtgtactactgctgcagtggtccagcaaccccctgaccttcggcgg
aggcaccaaggtggaaatcaagcggggtggtggtggttctggtggtggtggttctgaggtgcagctggtggaaa
gcggcggaggcctggtcaagcctggcggcagcctgagactgagctgtgccgccagcggcttccttcagcagc
tacgacatgagctgggtccgacaggctccaggcaagggactggaatgggtgtccaccatcagcagcggcggca
gctacacctactacctggacagcatcaagggccggttcaccatcagccgggacaacgccaagaacagcctgta
cctgcagatgaacagcctgcggccgaggacaccgccgtctactactgtgcccggcagggcctcgactactggg
gcagaggcaccctggtcaccgtgtccagcggggatcccaaagaggcctgccccaccggcctgtacacccacag
cggagagtgctgcaaggcctgcaacctgggagagggcgtggcccagccttgcggcgccaatcagaccgtgtgc
gagccctgcctggacagcgtgaccttcagcgacgtggtgtccgccaccgagccctgcaagccttgcaccgagtg
tgtgggcctgcagagcatgagcgcccctgcgtggaagccgacgacgccgtgtgtagatgcgcctacggctact
accaggacgagacaaccggcagatgcgaggcctgtagagtgtgcgaggccggcagcggcctggtgttcagttg
tcaagacaagcagaataccgtgtgtgaagagtgccccgacggcacctacagcgacgaggccaaccacgtgga
cccctgcctgccctgcactgtgtgcgaggacaccgagcggcagctgcgcgagtgcacaagatgggccgacgcc
gagtgcgaagagatccccggcagatggatcaccagaagcaccccccctgagggcagcgacagcaccgcccct
agcacccaggaacctgaggcccctcccgagcaggacctgatcgcctctacagtggccggcgtggtgacaaccg
tgatgggcagctctcagcccgtggtgacacggggcaccaccgacaatcccaaattttgggtgctggtggtggttg
gtggagtcctggcttgctatagcttgctagtaacagtggcctttattattttctgggtgaggagtaagaggagcag
gctcctgcacagtgactacatgaacatgactccccgccgccccgggcccacccgcaagcattaccagccctatg
ccccaccacgcgacttcgcagcctatcgctccagagtgaagttcagcaggagcgcagacgccccgcgtacca
gcagggccagaaccagctctataacgagctcaatctaggacgaagagaggagtacgatgttttggacaagag
acgtggccgggaccctgagatggggggaaagccgagaaggaagaaccctcaggaaggcctgtacaatgaact
gcagaaagataagatggcggaggcctacagtgagattgggatgaaaggcgagcgccggaggggcaaggggc
acgatggcctttaccagggtctcagtacagccaccaaggacacctacgacgcccttcacatgcaggccctgcct
cctcgctaagcatgcaacctcgatccggattagtccaatttgttaaagacaggatatcagtggtccaggctctag
ttttgactcaacaatatcaccagctgaagcctatagagtacgagccatagataaaataaaagatttatttagtc
tccagaaaaggggggaatgaaagaccccacctgtaggtttggcaagctagcttaagtaacgccattttgcaa
ggcatggaaaaatacataactgagaatagagaagttcagatcaaggtcaggaacagatggaacagctgaata
tgggccaaacaggatatctgtggtaagcagttcctgccccggctcagggccaagaacagatggaacagctgaa

Figure 26C tatgggccaaacaggatatctgtggtaagcagttcctgccccggctcagggccaagaacagatggtccccagat
gcggtccagccctcagcagtttctagagaaccatcagatgtttccagggtgccccaaggacctgaaatgaccct
gtgccttatttgaactaaccaatcagttcgcttctcgcttctgttcgcgcgcttctgctccccgagctcaataaaag
agcccacaacccctcactcggggcgccagtcctccgattgactgagtcgcccgggtacccgtgtatccaataaa
ccctcttgcagttgcatccgacttgtggtctcgctgttccttgggagggtctcctctgagtgattgactacccgtca
gcgggggtctttcacacatgcagcatgtatcaaaattaatttggttttttttcttaagtatttacattaaatggccat
agtacttaaagttacattggcttccttgaaataaacatggagtattcagaatgtgtcataaatatttctaattttaa
gatagtatctccattggctttctacttttctttttattttttttgtcctctgtcttccatttgttgttgttgtttgtttg
tttgtttgttggttggttggttaatttttttttaaagatcctacactatagttcaagctagactattagctactctgta
acccagggtgaccttgaagtcatgggtagcctgctgttttagccttcccacatctaagattacaggtatgagctat
cattttggtatattgattgattgattgattgatgtgtgtgtgtgtgattgtgtttgtgtgtgtgactgtgaaaatgtg
tgtatgggtgtgtgtgaatgtgtgtatgtatgtgtgtgtgtgagtgtgtgtgtgtgtgtgtgcatgtgtgtgtgtg
actgtgtctatgtgtatgactgtgtgtgtgtgtgtgtgtgtgtgtgtgtgtgtgtgtgtgtgtgttgtgaaaaaat
attctatggtagtgagagccaacgctccggctcaggtgtcaggttggttttttgagacagagtctttcacttagctt
ggaattcactggccgtcgttttacaacgtcgtgactgggaaaaccctggcgttacccaacttaatcgccttgcag
cacatccccctttcgccagctggcgtaatagcgaagaggcccgcaccgatcgcccttcccaacagttgcgcagc
ctgaatggcgaatggcgcctgatgcggtattttctccttacgcatctgtgcggtatttcacaccgcatatggtgca
ctctcagtacaatctgctctgatgccgcatagttaagccagccccgacacccgccaacacccgctgacgcgccct
gacgggcttgtctgctcccggcatccgcttacagacaagctgtgaccgtctccgggagctgcatgtgtcagaggt
tttcaccgtcatcaccgaaacgcgcgatgacgaaagggcctcgtgatacgcctatttttataggttaatgtcatga
taataatggtttcttagacgtcaggtggcacttttcggggaaatgtgcgcggaaccccatttgtttattttctaa
atacattcaaatatgtatccgctcatgagacaataaccctgataaatgcttcaataatattgaaaaaggaagag
tatgagtattcaacatttccgtgtcgcccttattccctttttgcggcattttgccttcctgtttttgctcacccagaaa
cgctggtgaaagtaaaagatgctgaagatcagttgggtgcacgagtgggttacatcgaactggatctcaacagc
ggtaagatccttgagagttttcgccccgaagaacgttttccaatgatgagcacttttaaagttctgctatgtggcg
cggtattatcccgtattgacgccgggcaagagcaactcggtcgccgcatacactattctcagaatgacttggttg
agtactcaccagtcacagaaaagcatcttacggatggcatgacagtaagagaattatgcagtgctgccataacc
atgagtgataacactgcggccaacttacttctgacaacgatcggaggaccgaaggagctaaccgcttttttgca
caacatggggatcatgtaactcgccttgatcgttgggaaccggagctgaatgaagccataccaaacgacgag
cgtgacaccacgatgcctgtagcaatggcaacaacgttgcgcaaactattaactggcgaactacttactctagct
tcccggcaacaattaatagactggatggaggcggataaagttgcaggaccacttctgcgctcggcccttccggc
tggctggtttattgctgataaatctggagccggtgagcgtgggtctcgcggtatcattgcagcactggggccaga

Figure 26D tggtaagccctcccgtatcgtagttatctacacgacggggagtcaggcaactatggatgaacgaaatagacaga
tcgctgagataggtgcctcactgattaagcattggtaactgtcagaccaagtttactcatatatactttagattgat
ttaaaacttcattttaatttaaaaggatctaggtgaagatcctttttgataatctcatgaccaaaatcccttaacg
tgagttttcgttccactgagcgtcagaccccgtagaaaagatcaaaggatcttcttgagatcctttttttctgcgcg
taatctgctgcttgcaaacaaaaaaaccaccgctaccagcggtggtttgtttgccggatcaagagctaccaactc
tttttccgaaggtaactggcttcagcagagcgcagataccaaatactgtccttctagtgtagccgtagttaggcca
ccacttcaagaactctgtagcaccgcctacatacctcgctctgctaatcctgttaccagtggctgctgccagtggc
gataagtcgtgtcttaccgggttggactcaagacgatagttaccggataaggcgcagcggtcgggctgaacggg
gggttcgtgcacacagcccagcttggagcgaacgacctacaccgaactgagatacctacagcgtgagcattga
gaaagcgccacgcttcccgaagggagaaaggcggacaggtatccggtaagcggcagggtcggaacaggaga
gcgcacgagggagcttccaggggggaaacgcctggtatctttatagtcctgtcgggtttcgccacctctgacttga
gcgtcgatttttgtgatgctcgtcaggggggcggagcctatggaaaaacgccagcaacgcggccttttacggtt
cctggccttttgctggccttttgctcacatgttctttcctgcgttatcccctgattctgtggataaccgtattaccgcc
tttgagtgagctgataccgctcgccgcagccgaacgaccgagcgcagcgagtcagtgagcgaggaagcggaa
gagcgcccaatacgcaaaccgcctctccccgcgcgttggccgattcattaatgcagctggcacgacaggtttccc
gactggaaagcgggcagtgagcgcaacgcaattaatgtgagttagctcactcattaggcaccccaggctttaca
ctttatgcttccggctcgtatgttgtgtggaattgtgagcggataacaatttcacacaggaaacagctatgaccat
gattacgcc

Figure 27A

CD44V6-4GS2-CAR.28Z NGFR WILD TYPE SHORT (V6 NWS) dna.gb aagctttgctcttaggagtttcctaatacatcccaaactcaaatatataaagcatttgacttgttctatgccctagg
gggcgggggaagctaagccagcttttttaacatttaaaatgttaattccattttaaatgcacagatgttttatt
tcataagggtttcaatgtgcatgaatgctgcaatattcctgttaccaaagctagtataaataaaaatagataaac
gtggaaattacttagagtttctgtcattaacgtttccttcctcagttgacaacataaatgcgctgctgagcaagcc
agtttgcatctgtcaggatcaatttcccattatgccagtcatattaattactagtcaattagttgattttatttttga
catatacatgtgaatgaaagaccccacctgtaggtttggcaagctagcttaagtaacgccattttgcaaggcatg
gaaaaatacataactgagaatagaaaagttcagatcaaggtcaggaacagatggaacagctgaatatgggcc
aaacaggatatctgtggtaagcagttcctgccccggctcagggccaagaacagatggaacagctgaatatggg
ccaaacaggatatctgtggtaagcagttcctgccccggctcagggccaagaacagatggtccccagatgcggtc
cagccctcagcagtttctagagaaccatcagatgtttccagggtgccccaaggacctgaaatgaccctgtgcctt
atttgaactaaccaatcagttcgcttctcgcttctgttcgcgcgcttatgctccccgagctcaataaaagagccca
caacccctcactcggggcgccagtcctccgattgactgagtcgcccgggtacccgtgtatccaataaaccctctt
gcagttgcatccgacttgtggtctcgctgttccttgggagggtctcctctgagtgattgactaccgtcagcgggg
gtctttcatttgggggctcgtccgggatcgggagacccctgcccagggaccaccgacccaccaccgggaggtaa
gctggccagcaacttatctgtgtctgtccgattgtctagtgtctatgactgattttatgcgcctgcgtcggtactagt
tagctaactagctctgtatctggcggacccgtggtggaactgacgagttcggaacacccggccgcaaccctggg
agacgtcccagggacttcgggggccgttttgtggcccgacctgagtcctaaaatcccgatcgtttaggactcttt
ggtgcaccccccttagaggagggatatgtggttctggtaggagacgagaacctaaaacagttcccgcctccgtc
tgaattttgctttcggtttgggaccgaagccgcgccgcgcgtcttgtctgctgcagcatcgttctgtgttgtctctg
tctgactgtgtttctgtatttgtctgaaaatatgggcccgggctagcctgttaccactcccttaagtttgaccttagg
tcactggaaagatgtcgagcggatcgctcacaaccagtcggtagatgtcaagaagagacgttgggttaccttct
gctctgcagaatggccaacctttaacgtcggatggccgcgagacggcacctttaaccgagacctcatcacccag
gttaagatcaaggtcttttcacctggcccgcatggacacccagaccaggtggggtacatcgtgacctgggaagc
cttggcttttgacccccctccctgggtcaagccctttgtacacctaagcctccgcctcctcttcctccatccgcccc
gtctctccccttgaacctcctcgttcgacccgcctcgatcctccctttatccagccctcactccttctctaggcgc
ccccatatggccatatgagatcttatatggggcaccccgcccttgtaaacttccctgaccctgacatgacaag
agttactaacagcccctctctccaagctcacttacaggctctctacttagtccagcacgaagtctggagacctctg
gcggcagcctaccaagaacaactggaccgaccggtggtacctcacccttaccgagtcggcgacacagtgtggg
tccgccgacaccagactaagaacctagaacctcgctggaaaggaccttacacagtcctgctgaccaccccacc
gccctcaaagtagacggcatcgcagcttggatacacgccgcccacgtgaaggctgccgaccccggggtggac

Figure 27B catcctctagactgccatggaagcccctgcccagctgctgttcctgctgctgctgtggctgcccgacaccaccggc
gagatcgtgctgacacagagccccgccaccctgtctctgagccctggcgagagagccaccctgagctgtagcgc
cagcagcagcatcaactacatctactggctgcagcagaagcccggccaggcccccagaatcctgatctacctga
ccagcaacctggccagcggcgtgcccgccagattttctggcagcggcagcggcaccgacttcaccctgaccatc
agcagcctggaacccgaggacttcgccgtgtactactgcctgcagtggtccagcaacccccctgaccttcggcgg
aggcaccaaggtggaaatcaagcggggtggtggtggttctggtggtggtggttctgaggtgcagctggtggaaa
gcggcggaggcctggtcaagcctggcggcagcctgagactgagctgtgccgccagcggcttccttcagcagc
tacgacatgagctgggtccgacaggctccaggcaagggactggaatgggtgtccaccatcagcagcggcggca
gctacacctacacctggacagcatcaagggccggttcaccatcagccgggacaacgccaagaacagcctgta
cctgcagatgaacagcctgcgggccgaggacaccgccgtctactactgtgcccggcagggcctcgactactggg
gcagaggcacccctggtcaccgtgtccagcggggatcccaaagaggcctgccccaccggcctgtacacccacag
cggagagtgctgcaaggcctgcaacctgggagagggcgtggcccagccttgcggcgccaatcagaccgtgtgc
gagccctgcctggacagcgtgaccttcagcgacgtggtgtccgccaccgagccctgcaagccttgcaccgagtg
tgtgggcctgcagagcatgagcgcccctgcgtggaagccgacgacgccgtgtgtagatgcgcctacggctact
accaggacgagacaaccggcagatgcgaggcctgtagagtgtgcgaggccggcagcggcctggtgttcagttg
tcaggacaagcagaacaccgtgtgtgaagagtgccccgacggcacctacagcgacgaggccaaccacgtgga
cccctgcctgccctgcactgtgtgcgaggacaccgagcggcagctgcgcgagtgcacaagatgggccgacgcc
gagtgcgaggaacccaaattttgggtgctggtggtggttggtggagtcctggcttgctatagcttgctagtaaca
gtggcctttattattttctgggtgaggagtaagaggagcaggctcctgcacagtgactacatgaacatgactccc
cgccgccccgggcccacccgcaagcattaccagccctatgccccaccacgcgacttcgcagcctatcgctccag
agtgaagttcagcaggagcgcagacgcccccgcgtaccagcagggccagaaccagctctataacgagctcaat
ctaggacgaagagaggagtacgatgttttggacaagagacgtggccgggaccctgagatggggggaaagccg
agaaggaagaaccctcaggaaggcctgtacaatgaactgcagaaagataagatggcggaggcctacagtga
gattgggatgaaaggcgagcgccggaggggcaaggggcacgatggcctttaccagggtctcagtacagccac
caaggacacctacgacgcccttcacatgcaggccctgcctcctcgctaagcatgcaacctcgatccggattagtc
caatttgttaaagacaggatatcagtggtccaggctctagttttgactcaacaatatcaccagctgaagcctata
gagtacgagccatagataaaataaagatttatttagtctccagaaaagggggaatgaaagaccccacct
gtaggtttggcaagctagcttaagtaacgccattttgcaaggcatggaaaatacataactgagaatagagaa
gttcagatcaaggtcaggaacagatggaacagctgaatatgggccaaacaggatatctgtggtaagcagttcc
tgccccggctcagggccaagaacagatggaacagctgaatatgggccaaacaggatatctgtggtaagcagtt
cctgccccggctcagggccaagaacagatggtccccagatgcggtccagccctcagcagtttctagagaaccat
cagatgtttccagggtgccccaaggacctgaaatgaccctgtgccttatttgaactaaccaatcagttcgcttctc

Figure 27C gcttctgttcgcgcgcttctgctccccgagctcaataaaagagcccacaaccccctcactcggggcgccagtcctc
cgattgactgagtcgcccggggtacccgtgtatccaataaaccctcttgcagttgcatccgacttgtggtctcgctg
ttccttgggagggtctcctctgagtgattgactacccgtcagcgggggtctttcacacatgcagcatgtatcaaaa
ttaatttggttttttttcttaagtatttacattaaatggccatagtacttaaagttacattggcttccttgaaataaac
atggagtattcagaatgtgtcataaatatttctaattttaagatagtatctccattggctttctacttttctttattt
tttttgtcctctgtcttccatttgttgttgttgttgtttgtttgtttgttggttggttggttaatttttttttaaagat
cctacactatagttcaagctagactattagctactctgtaacccagggtgaccttgaagtcatgggtagcctgctg
ttttagccttcccacatctaagattacaggtatgagctatcattttggtatattgattgattgattgattgatgtgt
gtgtgtgtgattgtgtttgtgtgtgtgactgtgaaaatgtgtgtatgggtgtgtgtgaatgtgtgtatgtatgtgtgt
gtgtgagtgtgtgtgtgtgtgtgtgcatgtgtgtgtgtgtgactgtgtctatgtgtatgactgtgtgtgtgtgtgt
gtgtgtgtgtgtgtgtgtgtgtgttgtgaaaaatattctatggtagtgagagccaacgctccggctcag
gtgtcaggttggttttgagacagagtctttcacttagcttggaattcactggccgtcgttttacaacgtcgtgact
gggaaaaccctggcgttacccaacttaatcgccttgcagcacatcccccctttcgccagctggcgtaatagcgaag
aggcccgcaccgatcgcccttcccaacagttgcgcagcctgaatggcgaatggcgcctgatgcggtattttctcc
ttacgcatctgtgcggtatttcacaccgcatatggtgcactctcagtacaatctgctctgatgccgcatagttaag
ccagccccgacacccgccaacacccgctgacgcgccctgacgggcttgtctgctcccggcatccgcttacagac
aagctgtgaccgtctccgggagctgcatgtgtcagaggttttcaccgtcatcaccgaaacgcgcgatgacgaaa
gggcctcgtgatacgcctatttttataggttaatgtcatgataataatggtttcttagacgtcaggtggcacttttc
ggggaaatgtgcgcggaacccctatttgtttatttttctaaatacattcaaatatgtatccgctcatgagacaata
accctgataaatgcttcaataatattgaaaaaggaagagtatgagtattcaacatttccgtgtcgcccttattccc
ttttttgcggcattttgccttcctgttttttgctcacccagaaacgctggtgaaagtaaaagatgctgaagatcagtt
gggtgcacgagtgggttacatcgaactggatctcaacagcggtaagatccttgagagttttcgccccgaagaac
gttttccaatgatgagcacttttaaagttctgctatgtggcgcggtattatcccgtattgacgccgggcaagagca
actcggtcgccgcatacactattctcagaatgacttggttgagtactcaccagtcacagaaaagcatcttacgga
tggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgtt
gggaaccggagctgaatgaagccataccaaacgacgagcgtgacaccacgatgcctgtagcaatggcaacaa
cgttgcgcaaactattaactggcgaactacttactctagcttcccggcaacaattaatagactggatggaggcgg
ataaagttgcaggaccacttctgcgctcggcccttccggctggctggtttattgctgataaatctggagccggtga
gcgtgggtctcgcggtatcattgcagcactggggccagatggtaagccctcccgtatcgtagttatctacacgac
ggggagtcaggcaactatggatgaacgaaatagacagatcgctgagataggtgcctcactgattaagcattgg
taactgtcagaccaagtttactcatatatactttagattgatttaaaacttcattttaatttaaaaggatctaggt

Figure 27D gaagatcctttttgataatctcatgaccaaaatcccttaacgtgagttttcgttccactgagcgtcagaccccgta
gaaaagatcaaaggatcttcttgagatcctttttttctgcgcgtaatctgctgcttgcaaacaaaaaaaccaccg
ctaccagcggtggtttgtttgccggatcaagagctaccaactcttttccgaaggtaactggcttcagcagagcgc
agataccaaatactgtccttctagtgtagccgtagttaggccaccacttcaagaactctgtagcaccgcctacat
acctcgctctgctaatcctgttaccagtggctgctgccagtggcgataagtcgtgtcttaccgggttggactcaag
acgatagttaccggataaggcgcagcggtcgggctgaacggggggttcgtgcacacagcccagcttggagcga
acgacctacaccgaactgagatacctacagcgtgagcattgagaaagcgccacgcttcccgaagggagaaag
gcggacaggtatccggtaagcggcagggtcggaacaggagagcgcacgagggagcttccaggggggaaacgc
ctggtatctttatagtcctgtcgggtttcgccacctctgacttgagcgtcgatttttgtgatgctcgtcagggggc
ggagcctatggaaaaacgccagcaacgcggcctttttacggttcctggccttttgctggccttttgctcacatgttc
tttcctgcgttatcccctgattctgtggataaccgtattaccgcctttgagtgagctgataccgctcgccgcagccg
aacgaccgagcgcagcgagtcagtgagcgaggaagcggaagagcgcccaatacgcaaaccgcctctccccgc
gcgttggccgattcattaatgcagctggcacgacaggtttcccgactggaaagcgggcagtgagcgcaacgca
attaatgtgagttagctcactcattaggcaccccaggctttacactttatgcttccggctcgtatgttgtgtggaatt
gtgagcggataacaatttcacacaggaaacagctatgaccatgattacgcc

Figure 28A

CD44v6-4GS2-CAR.28Z NGFR MUTATED LONG (V6 NML) dna.gbb aagctttgctcttaggagtttcctaatacatcccaaactcaaatatataaagcatttgacttgttctatgccctagg
gggcgggggaagctaagccagcttttttaacatttaaaatgttaattccattttaaatgcacagatgttttatt
tcataagggtttcaatgtgcatgaatgctgcaatattcctgttaccaaagctagtataaataaaaatagataaac
gtggaaattacttagagtttctgtcattaacgtttccttcctcagttgacaacataaatgcgctgctgagcaagcc
agtttgcatctgtcaggatcaatttcccattatgccagtcatattaattactagtcaattagttgattttattttga
catatacatgtgaatgaaagaccccacctgtaggtttggcaagctagcttaagtaacgccattttgcaaggcatg
gaaaaatacataactgagaatagaaaagttcagatcaaggtcaggaacagatggaacagctgaatatgggcc
aaacaggatatctgtggtaagcagttcctgccccggctcagggccaagaacagatggaacagctgaatatggg
ccaaacaggatatctgtggtaagcagttcctgccccggctcagggccaagaacagatggtccccagatgcggtc
cagccctcagcagtttctagagaaccatcagatgtttccagggtgccccaaggacctgaaatgaccctgtgcctt
atttgaactaaccaatcagttcgcttctcgcttctgttcgcgcgcttatgctccccgagctcaataaaagagccca
caccccctcactcggggcgccagtcctccgattgactgagtcgcccgggtacccgtgtatccaataaaccctctt
gcagttgcatccgacttgtggtctcgctgttccttgggagggtctcctctgagtgattgactaccgtcagcgggg
gtctttcatttgggggctcgtccgggatcgggagacccctgcccagggaccaccgacccaccaccgggaggtaa
gctggccagcaacttatctgtgtctgtccgattgtctagtgtctatgactgattttatgcgcctgcgtcggtactagt
tagctaactagctctgtatctggcggacccgtggtggaactgacgagttcggaacacccggccgcaaccctggg
agacgtcccagggacttcgggggccgttttgtggcccgacctgagtcctaaaatcccgatcgtttaggactcttt
ggtgcaccccccttagaggagggatatgtggttctggtaggagacgagaacctaaaacagttcccgcctccgtc
tgaattttgctttcggtttgggaccgaagccgcgccgcgcgtcttgtctgctgcagcatcgttctgtgttgtctctg
tctgactgtgtttctgtatttgtctgaaaatatgggcccgggctagcctgttaccactcccttaagtttgaccttagg
tcactggaaagatgtcgagcggatcgctcacaaccagtcggtagatgtcaagaagagacgttgggttaccttct
gctctgcagaatggccaacctttaacgtcggatggccgcgagacggcacctttaaccgagacctcatcacccag
gttaagatcaaggtcttttcacctggcccgcatggacacccagaccaggtggggtacatcgtgacctgggaagc
cttggcttttgacccccctccctgggtcaagcccttgtacaccctaagcctccgcctcctcttcctccatccgcccc
gtctctccccttgaacctcctcgttcgaccccgcctcgatcctccctttatccagccctcactccttctctaggcgc
ccccatatggccatatgagatcttatatggggcaccccgcccttgtaaacttccctgaccctgacatgacaag
agttactaacagcccctctctccaagctcacttacaggctctctacttagtccagcacgaagtctggagacctctg
gcggcagcctaccaagaacaactggaccgaccggtggtacctcacccttaccgagtcggcgacacagtgtggg
tccgccgacaccagactaagaacctagaacctcgctggaaaggaccttacacagtcctgctgaccaccccacc
gccctcaaagtagacggcatcgcagcttggatacacgccgcccacgtgaaggctgccgaccccggggtggac

Figure 28B catcctctagactgccatggaagcccctgcccagctgctgttcctgctgctgctgtggctgcccgacaccaccggc
gagatcgtgctgacacagagccccgccaccctgtctctgagccctggcgagagagccaccctgagctgtagcgc
cagcagcagcatcaactacatctactggctgcagcagaagcccggccaggcccccagaatcctgatctacctga
ccagcaacctggccagcggcgtgcccgccagattttctggcagcggcagcggcaccgacttcaccctgaccatc
agcagcctggaacccgaggacttcgccgtgtactactgctgcagtggtccagcaaccccctgaccttcggcgg
aggcaccaaggtggaaatcaagcggggtggtggtggttctggtggtggtggttctgaggtgcagctggtggaaa
gcggcggaggcctggtcaagcctggcggcagcctgagactgagctgtgccgccagcggcttccttcagcagc
tacgacatgagctgggtccgacaggctccaggcaagggactggaatgggtgtccaccatcagcagcggcggca
gctacacctactacctggacagcatcaagggccggttcaccatcagccgggacaacgccaagaacagcctgta
cctgcagatgaacagcctgcgggccgaggacaccgccgtctactactgtgcccggcagggcctcgactactggg
gcagaggcaccctggtcaccgtgtccagcggggatcccaaagaggcctgccccaccggcctgtacacccacag
cggagagtgctgcaaggcctgcaacctgggagagggcgtggcccagccttgcggcgccaatcagaccgtgtgc
gagccctgcctggacagcgtgaccttcagcgacgtggtgtccgccaccgagccctgcaagccttgcaccgagtg
tgtgggcctgcagagcatgagcgcccctgcgtggaagccgacgacgccgtgtgtagatgcgcctacggctact
accaggacgagacaaccggcagatgcgaggcctgtagagtgtgcgaggccggcagcggcctggtgttcagttg
tcaagacaagcagaataccgtgtgtgaagagtgccccgacggcacctacagcgacgaagccgccagagccgc
cgacgccgagtgcgaagagatccccggcagatggatcaccagaagcaccccccctgagggcagcgacagcac
cgcccctagcacccaggaacctgaggcccctcccgagcaggacctgatcgcctctacagtggccggcgtggtga
caaccgtgatgggcagctctcagcccgtggtgacacggggcaccaccgacaatcccaaattttgggtgctggtg
gtggttggtggagtcctggcttgctatagcttgctagtaacagtggcctttattattttctgggtgaggagtaagag
gagcaggctcctgcacagtgactacatgaacatgactccccgccgccccgggcccacccgcaagcattaccag
ccctatgccccaccacgcgacttcgcagcctatcgctccagagtgaagttcagcaggagcgcagacgcccccgc
gtaccagcagggccagaaccagctctataacgagctcaatctaggacgaagagaggagtacgatgttttggac
aagagacgtggccgggaccctgagatgggggggaaagccgagaaggaagaaccctcaggaaggcctgtacaa
tgaactgcagaaagataagatggcggaggcctacagtgagattgggatgaaaggcgagcgccggaggggca
aggggcacgatggcctttaccagggtctcagtacagccaccaaggacacctacgacgcccttcacatgcaggc
cctgcctcctcgctaagcatgcaacctcgatccggattagtccaatttgttaaagacaggatatcagtggtccag
gctctagttttgactcaacaatatcaccagctgaagcctatagagtacgagccatagataaaataaaagatttta
tttagtctccagaaaaggggggaatgaaagaccccacctgtaggtttggcaagctagcttaagtaacgccatt
ttgcaaggcatggaaaaatacataactgagaatagagaagttcagatcaaggtcaggaacagatggaacagc
tgaatatgggccaaacaggatatctgtggtaagcagttcctgccccggctcagggccaagaacagatggaaca
gctgaatatgggccaaacaggatatctgtggtaagcagttcctgccccggctcagggccaagaacagatggtcc

Figure 28C ccagatgcggtccagccctcagcagtttctagagaaccatcagatgtttccagggtgccccaaggacctgaaat
gaccctgtgccttatttgaactaaccaatcagttcgcttctcgcttctgttcgcgcgcttctgctccccgagctcaat
aaaagagcccacaaccccctcactcggggcgccagtcctccgattgactgagtcgcccgggtacccgtgtatcca
ataaaccctcttgcagttgcatccgacttgtggtctcgctgttccttgggagggtctcctctgagtgattgactacc
cgtcagcgggggtctttcacacatgcagcatgtatcaaaattaatttggttttttttcttaagtatttacattaaatg
gccatagtacttaaagttacattggcttccttgaaataaacatggagtattcagaatgtgtcataaatatttctaa
ttttaagatagtatctccattggctttctacttttctttttattttttttttgtcctctgtcttccatttgttgttgttgttgtt
tgtttgtttgtttgttggttggttggttaattttttttaaagatcctacactatagttcaagctagactattagctact
ctgtaacccagggtgaccttgaagtcatgggtagcctgctgttttagccttcccacatctaagattacaggtatga
gctatcattttggtatattgattgattgattgattgatgtgtgtgtgtgtgattgtgtttgtgtgtgactgtgaaa
atgtgtgtatgggtgtgtgtgaatgtgtgtatgtatgtgtgtgtgtgagtgtgtgtgtgtgtgtgtcatgtgtgtgt
gtgtgactgtgtctatgtgtatgactgtgtgtgtgtgtgtgtgtgtgtgtgtgtgtgtgtgtgtgttgtgaaa
aaatattctatggtagtgagagccaacgctccggctcaggtgtcaggttggttttttgagacagagtctttcactta
gcttggaattcactggccgtcgttttacaacgtcgtgactgggaaaaccctggcgttacccaacttaatcgccttg
cagcacatccccctttcgccagctggcgtaatagcgaagaggcccgcaccgatcgcccttcccaacagttgcgc
agcctgaatggcgaatggcgcctgatgcggtattttctccttacgcatctgtgcggtatttcacaccgcatatggt
gcactctcagtacaatctgctctgatgccgcatagttaagccagccccgacacccgccaacacccgctgacgcg
ccctgacgggcttgtctgctcccggcatccgcttacagacaagctgtgaccgtctccgggagctgcatgtgtcag
aggttttcaccgtcatcaccgaaacgcgcgatgacgaaagggcctcgtgatacgcctatttttataggttaatgtc
atgataataatggtttcttagacgtcaggtggcacttttcggggaaatgtgcgcggaaccccatttgtttattttt
ctaaatacattcaaatatgtatccgctcatgagacaataaccctgataaatgcttcaataatattgaaaagga
agagtatgagtattcaacatttccgtgtcgcccttattcccttttttgcggcatttgccttcctgttttgctcaccca
gaaacgctggtgaaagtaaaagatgctgaagatcagttgggtgcacgagtgggttacatcgaactggatctca
acagcggtaagatccttgagagttttcgccccgaagaacgttttccaatgatgagcacttttaaagttctgctatg
tggcgcggtattatcccgtattgacgccgggcaagagcaactcggtcgccgcatacactattctcagaatgactt
ggttgagtactcaccagtcacagaaaagcatcttacggatggcatgacagtaagagaattatgcagtgctgcca
taaccatgagtgataacactgcggccaacttacttctgacaacgatcggaggaccgaaggagctaaccgctttt
ttgcacaacatggggggatcatgtaactcgccttgatcgttgggaaccggagctgaatgaagccataccaaacga
cgagcgtgacaccacgatgcctgtagcaatggcaacaacgttgcgcaaactattaactggcgaactacttactc
tagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggc
cagatggtaagccctcccgtatcgtagttatctacacgacggggagtcaggcaactatggatgaacgaaataga

Figure 28D cagatcgctgagataggtgcctcactgattaagcattggtaactgtcagaccaagtttactcatatatactttaga
ttgatttaaaacttcatttttaatttaaaaggatctaggtgaagatcctttttgataatctcatgaccaaaatcccttt
aacgtgagttttcgttccactgagcgtcagaccccgtagaaaagatcaaaggatcttcttgagatccttttttctg
cgcgtaatctgctgcttgcaaacaaaaaaaccaccgctaccagcggtggtttgtttgccggatcaagagctacc
aactcttttccgaaggtaactggcttcagcagagcgcagataccaaatactgtccttctagtgtagccgtagtta
ggccaccacttcaagaactctgtagcaccgcctacatacctcgctctgctaatcctgttaccagtggctgctgcca
gtggcgataagtcgtgtcttaccgggttggactcaagacgatagttaccggataaggcgcagcggtcgggctga
acggggggttcgtgcacacagcccagcttggagcgaacgacctacaccgaactgagatacctacagcgtgagc
attgagaaagcgccacgcttcccgaagggagaaaggcggacaggtatccggtaagcggcagggtcggaacag
gagagcgcacgagggagcttcaggggggaaacgcctggtatctttatagtcctgtcgggtttcgccacctctgac
ttgagcgtcgatttttgtgatgctcgtcaggggggcggagcctatggaaaaacgccagcaacgcggccttttac
ggttcctggccttttgctggccttttgctcacatgttctttcctgcgttatcccctgattctgtggataaccgtattac
cgcctttgagtgagctgataccgctcgccgcagccgaacgaccgagcgcagcgagtcagtgagcgaggaagcg
gaagagcgcccaatacgcaaaccgcctctccccgcgcgttggccgattcattaatgcagctggcacgacaggtt
tcccgactggaaagcgggcagtgagcgcaacgcaattaatgtgagttagctcactcattaggcaccccaggctt
tacactttatgcttccggctcgtatgttgtgtggaattgtgagcggataacaatttcacacaggaaacagctatga
ccatgattacgcc

Figure 29A

CD44v6-4GS2-CAR.28Z NGFR MUTATED SHORT (V6 NMS) dna.gb aagctttgctcttaggagtttcctaatacatcccaaactcaaatatataaagcatttgacttgttctatgccctagg
gggcggggggaagctaagccagcttttttaacatttaaaatgttaattccattttaaatgcacagatgttttatt
tcataagggtttcaatgtgcatgaatgctgcaatattcctgttaccaaagctagtataaataaaaatagataaac
gtggaaattacttagagtttctgtcattaacgtttccttcctcagttgacaacataaatgcgctgctgagcaagcc
agtttgcatctgtcaggatcaatttcccattatgccagtcatattaattactagtcaattagttgattttattttga
catatacatgtgaatgaaagaccccacctgtaggtttggcaagctagcttaagtaacgccattttgcaaggcatg
gaaaaatacataactgagaatagaaaagttcagatcaaggtcaggaacagatggaacagctgaatatgggcc
aaacaggatatctgtggtaagcagttcctgccccggctcagggccaagaacagatggaacagctgaatatggg
ccaaacaggatatctgtggtaagcagttcctgccccggctcagggccaagaacagatggtccccagatgcggtc
cagccctcagcagtttctagagaaccatcagatgtttccagggtgccccaaggacctgaaatgaccctgtgcctt
atttgaactaaccaatcagttcgcttctcgcttctgttcgcgcgcttatgctccccgagctcaataaaagagccca
caaccccctcactcggggcgccagtcctccgattgactgagtcgcccgggtacccgtgtatccaataaaccctctt
gcagttgcatccgacttgtggtctcgctgttccttgggagggtctcctctgagtgattgactaccgtcagcgggg
gtctttcatttgggggctcgtccgggatcgggagacccctgcccagggaccaccgacccaccaccgggaggtaa
gctggccagcaacttatctgtgtctgtccgattgtctagtgtctatgactgattttatgcgcctgcgtcggtactagt
tagctaactagctctgtatctggcggacccgtggtggaactgacgagttcggaacacccggccgcaaccctggg
agacgtcccagggacttcggggggccgttttgtggcccgacctgagtcctaaaatcccgatcgtttaggactcttt
ggtgcacccccttagaggagggatatgtggttctggtaggagacgagaacctaaaacagttcccgcctccgtc
tgaattttgctttcggtttgggaccgaagccgcgccgcgcgtcttgtctgctgcagcatcgttctgtgttgtctctg
tctgactgtgtttctgtatttgtctgaaaatatgggcccgggctagcctgttaccactcccttaagtttgaccttagg
tcactggaaagatgtcgagcggatcgctcacaaccagtcggtagatgtcaagaagagacgttgggttaccttct
gctctgcagaatggccaaccttaacgtcggatggccgcgagacggcacctttaaccgagacctcatcacccag
gttaagatcaaggtcttttcacctggcccgcatggacacccagaccaggtggggtacatcgtgacctgggaagc
cttggcttttgacccccctccctgggtcaagccctttgtacacctaagcctccgcctcctcttcctccatccgcccc
gtctctccccttgaacctcctcgttcgaccccgcctcgatcctcctttatccagccctcactccttctctaggcgc
ccccatatggccatatgagatcttatatggggcaccccgccccttgtaaacttccctgaccctgacatgacaag
agttactaacagcccctctctccaagctcacttacaggctctctacttagtccagcacgaagtctggagacctctg
gcggcagcctaccaagaacaactggaccgaccggtggtacctcacccttaccgagtcggcgacacagtgtggg
tccgccgacaccagactaagaacctagaacctgctggaaaggaccttacacagtcctgctgaccaccccacc
gccctcaaagtagacggcatcgcagcttggatacacgccgcccacgtgaaggctgccgaccccggggtggac

Figure 29B catcctctagactgccatggaagcccctgcccagctgctgttcctgctgctgctgtggctgcccgacaccaccggc
gagatcgtgctgacacagagccccgccaccctgtctctgagccctggcgagagagccaccctgagctgtagcgc
cagcagcagcatcaactacatctactggctgcagcagaagcccggccaggcccccagaatcctgatctacctga
ccagcaacctggccagcggcgtgcccgccagattttctggcagcggcagcggcaccgacttcaccctgaccatc
agcagcctggaacccgaggacttcgccgtgtactactgctgcagtggtccagcaacccccctgaccttcggcgg
aggcaccaaggtggaaatcaagcggggtggtggtggttctggtggtggtggttctgaggtgcagctggtggaaa
gcggcggaggcctggtcaagcctggcggcagcctgagactgagctgtgccgccagcggcttccttcagcagc
tacgacatgagctgggtccgacaggctccaggcaagggactggaatgggtgtccaccatcagcagcggcggca
gctacacctactacctggacagcatcaagggccggttcaccatcagccgggacaacgccaagaacagcctgta
cctgcagatgaacagcctgcgggccgaggacaccgccgtctactactgtgcccggcagggcctcgactactggg
gcagaggcaccctggtcaccgtgtccagcggggatcccaaagaggcctgccccaccggcctgtacacccacag
cggagagtgctgcaaggcctgcaacctgggagagggcgtggcccagccttgcggcgccaatcagaccgtgtgc
gagccctgcctggacagcgtgaccttcagcgacgtggtgtccgccaccgagccctgcaagccttgcaccgagtg
tgtgggcctgcagagcatgagcgcccctgcgtggaagccgacgacgccgtgtgtagatgcgcctacggctact
accaggacgagacaaccggcagatgcgaggcctgtagagtgtgcgaggccggcagcggcctggtgttcagttg
tcaggacaagcagaacaccgtgtgtgaagagtgccccgacggcacctacagcgacgaggccgcccgggccgc
cgacgccgagtgcgaggaacccaaattttgggtgctggtggtggttggtggagtcctggcttgctatagcttgct
agtaacagtggcctttattattttctgggtgaggagtaagaggagcaggctcctgcacagtgactacatgaacat
gactccccgccgccccgggcccacccgcaagcattaccagccctatgccccaccacgcgacttcgcagcctatc
gctccagagtgaagttcagcaggagcgcagacgcccccgcgtaccagcagggccagaaccagctctataacg
agctcaatctaggacgaagagaggagtacgatgttttggacaagagacgtggccgggaccctgagatgggggg
gaaagccgagaaggaagaaccctcaggaaggcctgtacaatgaactgcagaaagataagatggcggaggcc
tacagtgagattgggatgaaaggcgagcgccggaggggcaaggggcacgatggcctttaccagggtctcagta
cagccaccaaggacacctacgacgcccttcacatgcaggccctgcctcctcgctaagcatgcaacctcgatccg
gattagtccaatttgttaaagacaggatatcagtggtccaggctctagttttgactcaacaatatcaccagctga
agcctatagagtacgagccatagataaaataaaagattttatttagtctccagaaaaggggggaatgaaaga
ccccacctgtaggtttggcaagctagcttaagtaacgccattttgcaaggcatggaaaaatacataactgagaa
tagagaagttcagatcaaggtcaggaacagatggaacagctgaatatgggccaaacaggatatctgtggtaag
cagttcctgccccggctcagggccaagaacagatggaacagctgaatatgggccaaacaggatatctgtggta
agcagttcctgccccggctcagggccaagaacagatggtccccagatgcggtccagccctcagcagtttctaga
gaaccatcagatgtttccagggtgccccaaggacctgaaatgaccctgtgccttatttgaactaaccaatcagtt
cgcttctcgcttctgttcgcgcgcttctgctccccgagctcaataaaagagcccacaacccctcactcggggcgcc

Figure 29C agtcctccgattgactgagtcgcccgggtacccgtgtatccaataaaccctcttgcagttgcatccgacttgtggt
ctcgctgttccttgggagggtctcctctgagtgattgactacccgtcagcggggtctttcacacatgcagcatgt
atcaaaattaatttggttttttttcttaagtatttacattaaatggccatagtacttaaagttacattggcttccttga
aataaacatggagtattcagaatgtgtcataaatatttctaattttaagatagtatctccattggctttctacttttt
cttttattttttttgtcctctgtcttccatttgttgttgttgttgtttgtttgtttgtttgttggttggttggttaatttttt
ttaaagatcctacactatagttcaagctagactattagctactctgtaacccagggtgaccttgaagtcatgggta
gcctgctgtttagccttcccacatctaagattacaggtatgagctatcattttggtatattgattgattgattgatt
gatgtgtgtgtgtgtgattgtgtttgtgtgtgtgactgtgaaaatgtgtgtatgggtgtgtgtgaatgtgtgtatgta
tgtgtgtgtgtgagtgtgtgtgtgtgtgtgtgcatgtgtgtgtgtgtgactgtgtctatgtgtatgactgtgtgtgt
gtgtgtgtgtgtgtgtgtgtgtgtgtgtgttgtgaaaaaatattctatggtagtgagagccaacgctccgg
ctcaggtgtcaggttggttttttgagacagagtctttcacttagcttggaattcactggccgtcgttttacaacgtcg
tgactgggaaaaccctggcgttacccaacttaatcgccttgcagcacatccccctttcgccagctggcgtaatag
cgaagaggcccgcaccgatcgcccttcccaacagttgcgcagcctgaatggcgaatggcgcctgatgcggtatt
ttctccttacgcatctgtgcggtatttcacaccgcatatggtgcactctcagtacaatctgctctgatgccgcatag
ttaagccagccccgacacccgccaacacccgctgacgcgccctgacgggcttgtctgctcccggcatccgcttac
agacaagctgtgaccgtctccgggagctgcatgtgtcagaggttttcaccgtcatcaccgaaacgcgcgatgac
gaaagggcctcgtgatacgcctatttttataggttaatgtcatgataataatggtttcttagacgtcaggtggcac
ttttcggggaaatgtgcgcggaaccccctatttgtttatttttctaaatacattcaaatatgtatccgctcatgagac
aataaccctgataaatgcttcaataatattgaaaaaggaagagtatgagtattcaacatttccgtgtcgcccctta
ttccctttttgcggcattttgccttcctgttttgctcacccagaaacgctggtgaaagtaaaagatgctgaagat
cagttgggtgcacgagtgggttacatcgaactggatctcaacagcggtaagatccttgagagttttcgccccgaa
gaacgttttccaatgatgagcacttttaaagttctgctatgtggcgcggtattatcccgtattgacgccgggcaag
agcaactcggtcgccgcatacactattctcagaatgacttggttgagtactcaccagtcacagaaaagcatctta
cggatggcatgacagtaagagaattatgcagtgctgccataaccatgagtgataacactgcggccaacttactt
ctgacaacgatcggaggaccgaaggagctaaccgcttttttgcacaacatgggggatcatgtaactcgccttga
tcgttgggaaccggagctgaatgaagccataccaaacgacgagcgtgacaccacgatgcctgtagcaatggca
acaacgttgcgcaaactattaactggcgaactacttactctagcttcccggcaacaattaatagactggatggag
gcggataaagttgcaggaccacttctgcgctcggcccttccggctggctggtttattgctgataaatctggagccg
gtgagcgtgggtctcgcggtatcattgcagcactggggccagatggtaagccctcccgtatcgtagttatctaca
cgacggggagtcaggcaactatggatgaacgaaatagacagatcgctgagataggtgcctcactgattaagca
ttggtaactgtcagaccaagtttactcatatatactttagattgatttaaaacttcattttaatttaaaaggatcta
ggtgaagatcctttttgataatctcatgaccaaaatcccttaacgtgagttttcgttccactgagcgtcagacccc

Figure 29D gtagaaaagatcaaaggatcttcttgagatcctttttttctgcgcgtaatctgctgcttgcaaacaaaaaaaccac
cgctaccagcggtggtttgtttgccggatcaagagctaccaactcttttccgaaggtaactggcttcagcagagc
gcagataccaaatactgtccttctagtgtagccgtagttaggccaccacttcaagaactctgtagcaccgcctac
atacctcgctctgctaatcctgttaccagtggctgctgccagtggcgataagtcgtgtcttaccgggttggactca
agacgatagttaccggataaggcgcagcggtcgggctgaacggggggttcgtgcacacagcccagcttggagc
gaacgacctacaccgaactgagatacctacagcgtgagcattgagaaagcgccacgcttcccgaagggagaa
aggcggacaggtatccggtaagcggcagggtcggaacaggagagcgcacgagggagcttcaggggggaaac
gcctggtatctttatagtcctgtcgggtttcgccacctctgacttgagcgtcgattttgtgatgctcgtcagggggg
gcggagcctatggaaaaacgccagcaacgcggcctttttacggttcctggccttttgctggccttttgctcacatg
ttctttcctgcgttatcccctgattctgtggataaccgtattaccgcctttgagtgagctgataccgctcgccgcag
ccgaacgaccgagcgcagcgagtcagtgagcgaggaagcggaagagcgcccaatacgcaaaccgcctctccc
cgcgcgttggccgattcattaatgcagctggcacgacaggtttcccgactggaaagcgggcagtgagcgcaac
gcaattaatgtgagttagctcactcattaggcaccccaggctttacactttatgcttccggctcgtatgttgtgtgg
aattgtgagcggataacaatttcacacaggaaacagctatgaccatgattacgcc

CHIMERIC ANTIGEN RECEPTORS

CROSS-REFERENCE TO RELATED APPLICATIONS

This application is a U.S. National Stage application of International Application No. PCT/162015/057049, filed Sep. 14, 2015, which claims priority benefit under 35 U.S.C. § 119 of European Patent Application No. 14184838.2, filed Sep. 15, 2014.

INCORPORATION BY REFERENCE OF MATERIAL SUBMITTED ELECTRONICALLY

This application incorporates by reference in its entirety a computer-readable nucleotide/amino acid sequence listing identified as one 142,851 bytes ASCII (text) file named "51646_SeqListing.txt," created Mar. 3, 2017.

FIELD OF THE INVENTION

The present invention relates to chimeric antigen receptors (CARs) comprising low-affinity nerve growth factor receptor (LNGFR) based spacers.

BACKGROUND TO THE INVENTION

Immunotherapy based on adoptive transfer of immune cells (e.g., T cells) into a patient can play an important role in treating disease, in particular cancer. Among many different types of immunotherapeutic agents, one of the most promising therapeutic methods involves the use of chimeric antigen receptors (CARs). CARs are genetically engineered receptors that are designed to target a specific antigen such as a tumor antigen (Sadelain et al., Cancer Discovery. 2013. 3(4):388-98). For example, T cells are transduced with CARs such that T cells expressing CARs kill tumors via the target antigen.

CARs comprise an extracellular ligand binding domain, most commonly a single chain variable fragment of a monoclonal antibody (scFv) linked to intracellular signaling components, most commonly CD3ζ alone or combined with one or more costimulatory domains. A spacer is often added between the extracellular antigen-binding domain and the transmembrane moiety to optimize the interaction with the target.

Most commonly, the constant immunoglobulin IgG1 hinge-CH2-CH3 Fc domain is used as a spacer domain. This spacer is used to select and track cells expressing the CAR. However, the IgG1 spacer may also bind to surface IgG Fc gamma receptors expressed on innate immune cells, like macrophages and natural killer cells (Hombach et al, *Gene Ther* 2000, June; 7(12):1067-75). This binding activates both the engineered T cells and the innate immune cells independent of the specificity of the CAR binding domain leading to an unwanted, off-target, immune response.

There is a need for CARs that do not generate off-target immune responses and are not prematurely cleared by the host immune system. There is also a need for CARs comprising spacer units that facilitate selection of cells genetically engineered to express CARs. The present invention addresses these needs.

SUMMARY OF THE INVENTION

According to a first aspect of the present invention there is provided a chimeric antigen receptor (CAR) comprising an extracellular spacer, which comprises at least part of the extracellular domain of the human low affinity nerve growth factor receptor (LNGFR) or a derivative thereof.

The CAR may comprise at least a fragment of the extracellular domain of the human low affinity nerve growth factor receptor (LNGFR) or a derivative thereof.

Preferably at least part of the LNGFR is suitable for facilitating immunoselection of cells transduced with said CAR.

Preferably the spacer lacks the intracellular domain of LNGFR.

Preferably the extracellular spacer comprises the first three TNFR-Cys domains of LNGFR or fragments or derivatives thereof.

In one embodiment the spacer comprises all four TNFR-Cys domains of LNGFR or fragments or derivatives thereof.

In another embodiment the spacer comprises the fourth TNFR-Cys domain (TNFR-Cys 4) but wherein the following amino acids are removed from said domain: NHVDPCLPCTVCEDTERQLRECTRW (SEQ ID NO: 13). Preferably the NHVDPCLPCTVCEDTERQLRECTRW (SEQ ID NO: 13) sequence is replaced with the following amino acid sequence ARA.

In another embodiment, the spacer comprises the serine/threonine-rich stalk of LNGFR.

In another embodiment, the spacer lacks the serine/threonine-rich stalk of LNGFR.

The spacer may comprise a sequence selected from the group consisting of SEQ ID NO: 1, SEQ ID NO: 3, SEQ ID NO: 5 or SEQ ID NO: 7 or a sequence at least 80, 85, 90, 95, 96, 97, 98 or 99% identical thereto.

In another embodiment, the spacer may consist of a sequence selected from the group consisting of SEQ ID NO: 1, SEQ ID NO: 3, SEQ ID NO: 5 or SEQ ID NO: 7 or a sequence at least 80, 85, 90, 95, 96, 97, 98 or 99% identical thereto.

SEQ ID NO: 1, SEQ ID NO: 3 and SEQ ID NO: 5 are preferred spacer elements.

According to an aspect of the present invention there is provided a chimeric antigen receptor (CAR) comprising
 (i) an antigen-specific targeting domain;
 (ii) an extracellular spacer domain as defined herein;
 (iii) a transmembrane domain;
 (iv) optionally at least one costimulatory domain; and
 (v) an intracellular signaling domain.

Preferably the antigen-specific targeting domain comprises an antibody or fragment thereof, more preferably a single chain variable fragment.

Preferably the antigen-specific targeting domain targets a tumour antigen. Examples of such antigens include CD44, CD19, CD20, CD22, CD23, CD123, CS-1, ROR1, mesothelin, c-Met, PSMA, Her2, GD-2, CEA, MAGE A3 TCR.

Preferably the tumour antigen is isoform 6 of CD44 (CD44v6).

Examples of transmembrane domains include a transmembrane domain of a zeta chain of a T cell receptor complex, CD28 and CD8a.

Examples of costimulatory domains include a costimulating domain from CD28, CD137 (4-1BB), CD134 (OX40), DapIO, CD27, CD2, CD5, ICAM-1, LFA-1, Lck, TNFR-I, TNFR-II, Fas, CD30 and CD40.

Examples of intracellular signaling domains include human CD3 zeta chain, FcγRIII, FcsRI, a cytoplasmic tail of a Fc receptor and an immunoreceptor tyrosine-based activation motif (ITAM) bearing cytoplasmic receptors.

In a preferred embodiment, the antigen-specific targeting domain of the CAR targets CD44v6, the transmembrane domain of the CAR comprises a transmembrane domain of CD28, the intracellular signaling domain of the CAR comprises an intracellular signaling domain of human CD3 zeta chain and the costimulatory domain of the CAR comprises a CD28 endo-costimulating domain.

In another aspect of the present invention there is provided a polynucleotide encoding a CAR of the invention and as defined herein.

Preferably the polynucleotide encodes a spacer domain that comprises the sequence of SEQ ID NO: 2, SEQ ID NO: 4, SEQ ID NO: 6 or SEQ ID NO: 8, or a sequence at least 80, 85, 90, 95, 96, 97, 98 or 99% identical thereto.

In one embodiment, the polynucleotide encodes a spacer domain that consists of the sequence of SEQ ID NO: 2, SEQ ID NO: 4, SEQ ID NO: 6 or SEQ ID NO: 8, or a sequence at least 80, 85, 90, 95, 96, 97, 98 or 99% identical thereto.

In another aspect of the present invention there is provided a vector comprising the polynucleotide of the invention.

In one embodiment, the vector is a viral vector.

In another aspect of the present invention there is provided a cell comprising a CAR, a polynucleotide, or a vector of the present invention. Preferably the cell is a T-cell.

In another aspect of the present invention there is provided a pharmaceutical composition comprising the cell of the invention.

In another aspect of the present invention there is provided a CAR, a polynucleotide, a vector or a cell of the invention for use in therapy, preferably cancer therapy.

In another aspect of the present invention there is provided a CAR of the present invention wherein the antigen-specific targeting domain targets CD44v6 for use in treating tumours that express CD44.

In another aspect of the present invention there is provided a method of treatment comprising administering a CAR, a polynucleotide, a vector or a cell of the invention to a subject in need of the same.

Exemplary CARs are shown in FIGS. 10 to 17.

DESCRIPTION OF THE DRAWINGS

FIG. 7 BIS. LNGFR-spaced CD44v6–CAR.28z T cells mediate superior antimyeloma effects in a well-established disease model. NSG mice were infused with CD44v6+ MM1.S cells expressing luciferase and, after 26 days, treated with LNGFR-spaced CD44v6–CAR.28z T cells (NMS), CH2CH3-spaced CD44v6–CAR.28z T cells (CHVV) or with T cells expressing an irrelevant CAR (CTR), all sorted to >95% purity. A. The circulating amount of tumor cells was evaluated as relative light units (RLU) at the indicated time points. B. Kaplan-Meyer survival curves of treated mice. Results from a Log-Rank test comparing the different conditions are shown (**P<0.01).

FIG. 8. Sequence of human LNGFR.

FIGS. 9A and 9B. Sequence of CD44v6CAR.28z. The SCFV, CH2CH3, CD28 and zeta chain sequences are shown.

FIG. 10. Exemplary sequence of a CD44v6CAR.28z with spacer LNGFR wild-type long (NWL) (SEQ ID NO: 21)

FIG. 11. Exemplary sequence of a CD44v6–CAR28z with spacer LNGFR wild-type short (NWS) (SEQ ID NO: 22)

FIG. 12. Exemplary sequence of a CD44v6–CAR28z with spacer LNGFR mutated long (NML) (SEQ ID NO: 23)

FIG. 13. Exemplary sequence of a CD44v6–CAR28z with spacer LNGFR mutated short (NMS) (SEQ ID NO: 24)

FIG. 14. Exemplary sequence of a CD44v6CAR.28z with spacer LNGFR wild-type long (NWL) (SEQ ID NO: 25)

FIG. 15. Exemplary sequence of a CD44v6–CAR28z with spacer LNGFR wild-type short (NWS) (SEQ ID NO: 26)

FIG. 16. Exemplary sequence of a CD44v6–CAR28z with spacer LNGFR mutated long (NML) (SEQ ID NO: 27)

FIG. 17. Exemplary sequence of a CD44v6–CAR28z with spacer LNGFR mutated short (NMS) (SEQ ID NO: 28)

FIG. 18. Sequence of CD44v6–4GS2-CAR28z, with spacer LNGFR wild-type long (NWL) (SEQ ID NO: 32)

FIG. 19. Sequence of CD44v6–4GS2-CAR28z, with spacer LNGFR wild-type short (NWS) (SEQ ID NO: 33)

FIG. 20. Sequence of CD44v6–4GS2-CAR28z with spacer LNGFR mutated long (NML) (SEQ ID NO: 34)

FIG. 21. Sequence of CD44v6–4GS2-CAR28z with spacer LNGFR mutated short (NMS) (SEQ ID NO: 35)

FIGS. 26A-26D. Polynucleotide sequence of CD44v6–4GS2-CAR28z, with spacer LNGFR wild-type long (NWL) (SEQ ID NO: 37).

FIGS. 27A-27D. Polynucleotide sequence of CD44v6–4GS2-CAR28z, with spacer LNGFR wild-type short (NWS) (SEQ ID NO: 38).

FIGS. 28A-28D. Polynucleotide sequence of CD44v6-4GS2-CAR28z with spacer LNGFR mutated long (NML) (SEQ ID NO: 39).

FIGS. 29A-29D. Polynucleotide sequence of CD44v6-4GS2-CAR28z with spacer LNGFR mutated short (NMS) (SEQ ID NO: 40).

DETAILED DESCRIPTION OF THE INVENTION

Figure 1A:
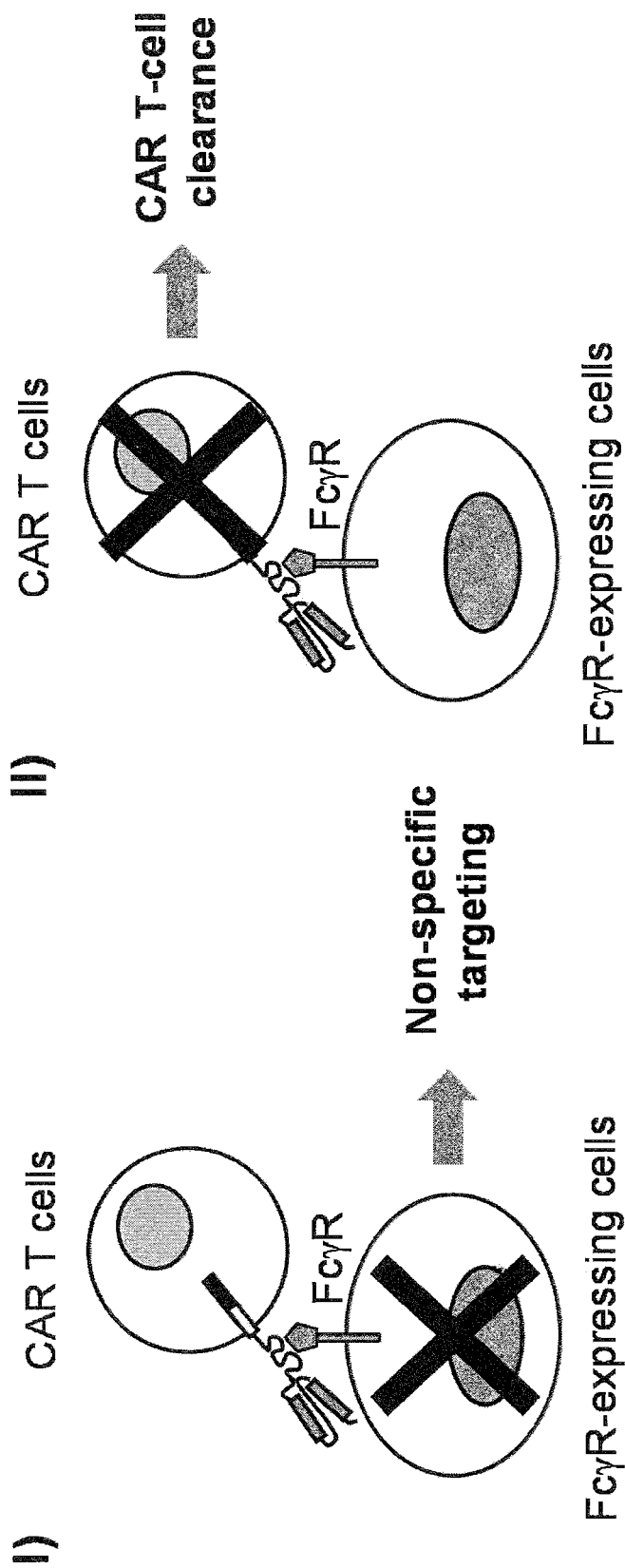
FIG. 1. Rationale of generating different LNGFR-spaced CD44v6–CAR.28z constructs. A. Scheme explaining the limitations of CAR T cells carrying the IgG1 CH2CH3 spacer. B. Structure of the extracellular portion of the low-affinity nerve growth factor receptor (LNGFR) and of the 4 new CAR constructs that have been generated. The CD44v6–CAR.28z carrying the wild-type or the mutated IgG1 CH2CH3 spacer (mCH2CH3) are also included. CHW: CD44v6–CAR.28z carrying the wild-type CH2CH3 spacer. CHM: CD44v6–CAR.28z carrying the mutated CH2CH3 spacer. NWL: CD44v6–CAR.28z carrying the LNGFR wild-type long spacer (including the 4 TNFR-Cys domains and the stalk). NWS: CD44v6–CAR.28z carrying the LNGFR wild-type short spacer (including only the 4 TNFR-Cys domains). NML: CD44v6–CAR.28z carrying the LNGFR mutated long spacer (including the 4 TNFR-Cys domains with a deletion in the fourth domain and the stalk). NMS: CD44v6–CAR.28z carrying the LNGFR mutated short spacer (including the 4 TNFR-Cys domains with a deletion in the fourth domain and the stalk). Curly brackets indicate the spacer length expressed in amino acids. Grey: scFv. White: co-stimulatory domain CD28; Black: CD3ζ.

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F., and Maniatis, T. (1989) *Molecular Cloning: A Laboratory Manual,* 2nd Edition, Cold Spring Harbor Laboratory Press; Ausubel, F. M. et al. (1995 and periodic supplements) *Current Protocols in Molecular Biology,* Ch. 9, 13 and 16, John Wley & Sons; Roe, B., Crabtree, J., and Kahn, A. (1996) *DNA Isolation and Sequencing: Essential Techniques,* John Wiley & Sons; Polak, J. M., and McGee, J. O'D. (1990) *In Situ Hybridization: Principles and Practice,* Oxford University Press; Gait, M. J. (1984) *Oligonucleotide Synthesis: A Practical Approach,* IRL Press; and Lilley, D. M., and Dahlberg, J. E. (1992) *Methods in Enzymology: DNA Structures Part A: Synthesis and Physical Analysis of DNA,* Academic Press. Each of these general texts is herein incorporated by reference.

Chimeric Antigen Receptors

"Chimeric antigen receptor" or "CAR" or "CARs" as used herein refers to engineered receptors which can confer an antigen specificity onto cells (for example T cells such as naive T cells, central memory T cells, effector memory T cells or combinations thereof). CARs are also known as artificial T-cell receptors, chimeric T-cell receptors or chimeric immunoreceptors. Preferably the CARs of the invention comprise an antigen-specific targeting region, an extracellular domain, a transmembrane domain, optionally one or more co-stimulatory domains, and an intracellular signaling domain.

Antigen-specific Targeting Domain

The antigen-specific targeting domain provides the CAR with the ability to bind to the target antigen of interest. The antigen-specific targeting domain preferably targets an antigen of clinical interest against which it would be desirable to trigger an effector immune response that results in tumor killing.

The antigen-specific targeting domain may be any protein or peptide that possesses the ability to specifically recognize and bind to a biological molecule (e.g., a cell surface receptor or tumor protein, or a component thereof). The antigen-specific targeting domain includes any naturally occurring, synthetic, semi-synthetic, or recombinantly produced binding partner for a biological molecule of interest.

Illustrative antigen-specific targeting domains include antibodies or antibody fragments or derivatives, extracellular domains of receptors, ligands for cell surface molecules/receptors, or receptor binding domains thereof, and tumor binding proteins.

In a preferred embodiment, the antigen-specific targeting domain is, or is derived from, an antibody. An antibody-derived targeting domain can be a fragment of an antibody or a genetically engineered product of one or more fragments of the antibody, which fragment is involved in binding with the antigen. Examples include a variable region (Fv), a complementarity determining region (CDR), a Fab, a single chain antibody (scFv), a heavy chain variable region (VH), a light chain variable region (VL) and a camelid antibody (VHH).

In a preferred embodiment, the binding domain is a single chain antibody (scFv). The scFv may be murine, human or humanized scFv.

"Complementarity determining region" or "CDR" with regard to an antibody or antigen-binding fragment thereof refers to a highly variable loop in the variable region of the heavy chain or the light chain of an antibody. CDRs can interact with the antigen conformation and largely determine binding to the antigen (although some framework regions are known to be involved in binding). The heavy chain variable region and the light chain variable region each contain 3 CDRs.

"Heavy chain variable region" or "VH" refers to the fragment of the heavy chain of an antibody that contains three CDRs interposed between flanking stretches known as framework regions, which are more highly conserved than the CDRs and form a scaffold to support the CDRs.

"Light chain variable region" or "VL" refers to the fragment of the light chain of an antibody that contains three CDRs interposed between framework regions.

"Fv" refers to the smallest fragment of an antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence.

Antibodies that specifically bind a tumor cell surface molecule can be prepared using methods well known in the art. Such methods include phage display, methods to generate human or humanized antibodies, or methods using a transgenic animal or plant engineered to produce human antibodies. Phage display libraries of partially or fully synthetic antibodies are available and can be screened for an antibody or fragment thereof that can bind to the target molecule. Phage display libraries of human antibodies are also available. Once identified, the amino acid sequence or polynucleotide sequence coding for the antibody can be isolated and/or determined.

Examples of antigens which may be targeted by the CAR of the invention include but are not limited to antigens expressed on cancer cells and antigens expressed on cells associated with various hematologic diseases, autoimmune diseases, inflammatory diseases and infectious diseases.

Wth respect to targeting domains that target cancer antigens, the selection of the targeting domain will depend on the type of cancer to be treated, and may target tumor antigens. A tumor sample from a subject may be characterized for the presence of certain biomarkers or cell surface markers. For example, breast cancer cells from a subject may be positive or negative for each of Her2Neu, Estrogen receptor, and/or the Progesterone receptor. A tumor antigen or cell surface molecule is selected that is found on the individual subject's tumor cells. Preferably the antigen-specific targeting domain targets a cell surface molecule that is found on tumor cells and is not substantially found on normal tissues, or restricted in its expression to non-vital normal tissues.

Further antigens specific for cancer which may be targeted by the CAR of the invention include but are not limited to any one or more of carcinoembryonic antigen (CEA), prostate specific antigen, PSMA, Her2/neu, estrogen receptor, progesterone receptor, ephrinB2, ROR1, mesothelin, c-Met, GD-2, and MAGE A3 TCR, 4-1BB, 5T4, adenocarcinoma antigen, alpha-fetoprotein, BAFF, B-lymphoma cell, C242 antigen, CA-125, carbonic anhydrase 9 (CA-IX), CCR4, CD152, CD200, CD22, CD19, CD22, CD123, CD221, CD23 (IgE receptor), CD28, CD30 (TNFRSF8), CD33, CD4, CD40, CD44, CD44 v6, CD51, CD52, CD56, CD74, CD80, CS-1, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HGF, human scatter factor receptor kinase, IGF-1 receptor, IGF-I, IgGI, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-Rα, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2 or vimentin.

Antigens specific for inflammatory diseases which may be targeted by the CAR of the invention include but are not limited to any one or more of AOC3 (VAP-1), CAM-3001, CCL11 (eotaxin-1), CD125, CD147 (basigin), CD154 (CD40L), CD2, CD20, CD23 (IgE receptor), CD25 (a chain of IL-2 receptor), CD3, CD4, CDS, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, Lama glama, LFA-1 (CD11a), MEDI-528, myostatin, OX-40, rhuMAb β7, scleroscin, SOST, TGF β1, TNF-a or VEGF-A.

Antigens specific for neuronal disorders which may be targeted by the CAR of the invention include but are not limited to any one or more of beta amyloid or MABT5102A.

Antigens specific for diabetes which may be targeted by the CAR of the invention include but are not limited to any one or more of L-1β or CD3. Other antigens specific for diabetes or other metabolic disorders will be apparent to those of skill in the art.

Antigens specific for cardiovascular diseases which may be targeted by the CARs of the invention include but are not limited to any one or more of C5, cardiac myosin, CD41 (integrin alpha-IIb), fibrin II, beta chain, ITGB2 (CD18) and sphingosine-1-phosphate.

Preferably, the antigen-specific binding domain specifically binds to a tumor antigen. In a specific embodiment, the polynucleotide codes for a single chain Fv that specifically binds CD44v6.

An exemplary antigen-specific targeting domain is a CD44v6-specific single-chain fragment (scFV) such as described in Casucci M et al, *Blood*, 2013, November 14;122(20):3461-72. Such a sequence is shown below:

```
CD44v6-specific single-chain fragment (scFv)
                                       (SEQ ID NO: 17)
MEAPAQLLFLLLLWLPDTTGEIVLTQSPATLSLSPGERATLSCSASSSI

NYIYWLQQKPGQAPRILIYLTSNLASGVPARFSGSGSGTDFTLTISSLE

PEDFAVYYCLQWSSNPLTFGGGTKVEIKRGGGGSGGGGSGGGGSGGGGS

EVQLVESGGGLVKPGGSLRLSCAASGFTFSSYDMSWVRQAPGKGLEWVS

TISSGGSYTYYLDSIKGRFTISRDNAKNSLYLQMNSLRAEDTAVYYCAR

QGLDYWGRGTLVTVSS
```

In one embodiment, the CD44v6-specific single-chain fragment comprises at least 85, 90, 95, 97, 98 or 99% identity to SEQ ID NO: 17.

In a further preferred embodiment, the light chain variable region and the heavy chain variable region of the CD44v6-specific single chain fragment are connected to one another via a peptide linker having the following sequence GGGGSGGGGS (4GS2). Such CD44v6-specific single chain fragment (CD44v6-4GS2) has the following sequence:

```
                                       (SEQ ID NO: 31)
MEAPAQLLFLLLLWLPDTTGEIVLTQSPATLSLSPGERATLSCSASSSI

NYIYWLQQKPGQAPRILIYLTSNLASGVPARFSGSGSGTDFTLTISSLE

PEDFAVYYCLQWSSNPLTFGGGTKVEIKRGGGGSGGGGSEVQLVESGGG

LVKPGGSLRLSCAASGFTFSSYDMSWVRQAPGKGLEWVSTISSGGSYTY

YLDSIKGRFTISRDNAKNSLYLQMNSLRAEDTAVYYCARQGLDYWGRGT

LVTVSS
```

Co-stimulatory Domain

The CAR of the invention may also comprise one or more co-stimulatory domains. This domain may enhance cell proliferation, cell survival and development of memory cells.

Each co-stimulatory domain comprises the co-stimulatory domain of any one or more of, for example, members of the TNFR super family, CD28, CD137 (4-1BB), CD134 (OX40), DapIO, CD27, CD2, CD5, ICAM-1, LFA-1, Lck, TNFR-1, TNFR-II, Fas, CD30, CD40 or combinations thereof. Co-stimulatory domains from other proteins may also be used with the CAR of the invention. Additional co-stimulatory domains will be apparent to those of skill in the art.

In one embodiment the transmembrane and costimulatory domain are both derived from CD28. In one embodiment the transmembrane and intracellular costimulatory domain comprise the sequence below:

```
Transmembrane and intracellular portion of the human CD28 (UNIPROT: P10747, CD28_HUMAN, position 153-220)
                                       (SEQ ID NO: 18)
FWVLVVVGGVLACYSLLVTVAFIIFWVRSKRSRLLHSDYMNMTPRRPG

PTRKHYQPYAPPRDFAAYRS
```

In one embodiment the transmembrane and intracellular signaling domain comprises at least 85, 90, 95, 97, 98 or 99% identity to SEQ ID NO: 18.

In one embodiment the transmembrane domain of CD28 comprises the sequence FVWLVVVGGVLACYSLLVTVAFIIFVW (SEQ ID NO: 29).

In one embodiment the intracellular costimulatory domain of CD28 comprises the sequence RSKRSRLLHSDYMNMTPRRPGPTRKHYQPYAPPRDFAAYRS (SEQ ID NO: 30).

Intracellular Signaling Domain

The CAR of the invention may also comprise an intracellular signaling domain. This domain may be cytoplasmic and may transduce the effector function signal and direct the cell to perform its specialized function. Examples of intracellular signaling domains include, but are not limited to, ζ chain of the T-cell receptor or any of its homologs (e.g., η chain, FcεR1γ and β chains, MB1 (Igα) chain, B29 (Igβ) chain, etc.), CD3 polypeptides (Δ,δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28. The intracellular signaling domain may be human CD3 zeta chain, FcγRIII, FcsRI, cytoplasmic tails of Fc receptors, immunoreceptor tyrosine-based activation motif (ITAM) bearing cytoplasmic receptors or combinations thereof.

Preferable, the intracellular signaling domain comprises the intracellular signaling domain of human CD3 zeta chain.

In one embodiment the intracellular signaling domain of human CD3 zeta chain comprises the following sequence:

```
UNIPROT: P20963, CD3Z_HUMAN, position 31-143
                                            (SEQ ID NO: 20)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR
```

In one embodiment, the intracellular signaling domain comprises at least 85, 90, 95, 97, 98 or 99% identity to SEQ ID NO: 20.

Additional intracellular signaling domains will be apparent to those of skill in the art and may be used in connection with alternate embodiments of the invention.

Transmembrane Domain

The CAR of the invention may also comprise a transmembrane domain. The transmembrane domain may comprise the transmembrane sequence from any protein which has a transmembrane domain, including any of the type I, type II or type III transmembrane proteins. The transmembrane domain of the CAR of the invention may also comprise an artificial hydrophobic sequence. The transmembrane domains of the CARs of the invention may be selected so as not to dimerize. Additional transmembrane domains will be apparent to those of skill in the art. Examples of transmembrane (TM) regions used in CAR constructs are: 1) The CD28 TM region (Pule et al, *Mol Ther*, 2005, November;12(5):933-41; Brentjens et al, *CCR*, 2007, Sep. 15;13(18 Pt 1):5426-35; Casucci et al, *Blood*, 2013, Nov. 14;122(20): 3461-72.); 2) The OX40 TM region (Pule et al, *Mol Ther*, 2005, November;12(5):933-41); 3) The 41BB TM region (Brentjens et al, *CCR*, 2007, Sep. 15;13(18 Pt 1):5426-35); 4) The CD3 zeta TM region (Pule et al, *Mol Ther*, 2005, November;12(5):933-41; Savoldo B, *Blood*, 2009, Jun. 18;113(25):6392-402.); 5) The CD8a TM region (Maher et al, *Nat Biotechnol*, 2002, January;20(1):70-5.; Imai C, *Leukemia*, 2004, April;18(4):676-84; Brentjens et al, *CCR*, 2007, Sep. 15;13(18 Pt 1):5426-35; Milone et al, *Mol Ther*, 2009, August;17(8):1453-64.).

In one embodiment the transmembrane and intracellular signaling domain are both derived from CD28. In one embodiment the transmembrane and intracellular signaling domain comprise the sequence below:

```
Transmembrane and intracellular portion of the human CD28 (UNIPROT: P10747, CD28_HUMAN, position 153-220)
                                            (SEQ ID NO: 18)
FWVLVVVGGVLACYSLLVTVAFIIFWVRSKRSRLLHSDYMNMTPRRPGP

TRKHYQPYAPPRDFAAYRS
```

In one embodiment the transmembrane and intracellular signaling domain comprises at least 85, 90, 95, 97, 98 or 99% identity to SEQ ID NO: 18.

Spacer domain—Low Affinity Nerve Growth Factor Receptor LNGFR

The CAR of the invention comprises an extracellular spacer domain. The extracellular spacer domain is attached to the antigen-specific targeting region and the transmembrane domain.

The CAR of the present invention comprises an extracellular spacer which comprises at least part of the extracellular domain of human low affinity nerve growth factor receptor (LNGFR) or a derivative thereof.

LNGFR is not expressed on the majority of human hematopoietic cells, thus allowing quantitative analysis of transduced gene expression by immunofluorescence, with single cell resolution. Thus, fluorescence activated cell sorter analysis of expression of LNGFR may be performed in transduced cells to study gene expression. Further details on analysis using LNGFR may be found in Mavilio 1994, Blood 83, 1988-1997.

A sequence of human LNGFR is shown in FIG. 8 (SEQ ID NO: 14).

The present invention in one embodiment makes use of a truncated LNGFR (also known as ΔLNGFR). Preferably the LNGFR used in the present invention is truncated in its intracytoplasmic domain. Such a truncation is described in Mavilio 1994.

Thus, preferably the LNGFR spacer of the present invention comprises at least part of the extracellular domain or a derivative thereof but lacks the intracellular domain of LNGFR. The extracellular domain may comprise amino acids 29-250 of LNGFR or a derivative thereof.

```
Extracellular domain of the human LNGFR (UNIPROT # P08138, TNR16_HUMAN, position 29-250)
                                            (SEQ ID NO: 19)
KEACPTGLYTHSGECCKACNLGEGVAQPCGANQTVCEPCLDSVTFSDVV

SATEPCKPCTECVGLQSMSAPCVEADDAVCRCAYGYYQDETTGRCEACR

VCEAGSGLVFSCQDKQNTVCEECPDGTYSDEANHVDPCLPCTVCEDTER

QLRECTRWADAECEEIPGRWITRSTPPEGSDSTAPSTQEPEAPPEQDLI

ASTVAGVVTTVMGSSQPVVTRGTTDN
```

Preferably the LNGFR lacks the signal peptide.

In one embodiment, the spacer comprises at least part of a protein having at least 85, 90, 95, 96, 97, 98 or 99% identity to the extracellular domain of LNGFR (e.g., SEQ ID NO: 19). In one embodiment, the spacer comprises at least part of a protein having at least 85, 90, 95, 96, 97, 98 or 99% identity to amino acids 29-250 of the LNGFR protein.

LNGFR comprises 4 TNFR-Cys domains (TNFR-Cys 1, TNFR-Cys 2, TNFR-Cys 3 and TNFR-Cys 4). Sequences of the domains are exemplified below:

```
TNFR-Cys 1,
                                             SEQ ID NO: 9
ACPTGLYTHSGECCKACNLGEGVAQPCGANQTVC

TNFR-Cys 2,
                                             SEQ ID NO: 10
PCLDSVTFSDVVSATEPCKPCTECVGLQSMSAPCVEADDAVC

TNFR-Cys 3,
                                             SEQ ID NO: 11
RCAYGYYQDETTGRCEACRVCEAGSGLVFSCQDKQNTVC

TNFR-Cys 4,
                                             SEQ ID NO: 12
ECPDGTYSDEANHVDPCLPCTVCEDTERQLRECTRWADAEC
```

In one embodiment, the spacer comprises TNFR-Cys 1, 2 and 3 domains or fragments or derivatives thereof. In another embodiment, the spacer comprises the TNFR-Cys 1, 2, 3 and 4 domains or fragments or derivatives thereof.

In one embodiment the spacer comprises a sequence having at least 80, 85, 90, 95, 96, 97, 98, 99% identity or 100% identity to TNFR-Cys 1 (SEQ ID NO: 9), a sequence having at least 80, 85, 90, 95, 96, 97, 98, 99% identity or 100% identity to TNFR-Cys 2 (SEQ ID NO: 10), or a sequence having at least 80, 85, 90, 95, 96, 97, 98, 99% identity or 100% identity to TNFR-Cys 3 (SEQ ID NO: 11). The spacer may further comprise a sequence having at least 80, 85, 90, 95, 96, 97, 98, 99% identity or 100% identity to TNFR-Cys 4 (SEQ ID NO: 12).

Rather than comprise the full TNFR-Cys 4 domain, the spacer may comprise a TNFR-Cys 4 domain with the following amino acids deleted from said domain: NHVDPCLPCTVCEDTERQLRECTRW (SEQ ID NO: 13). In one embodiment, the NHVDPCLPCTVCEDTERQL-RECTRW (SEQ ID NO: 13) amino acids are replaced with the following amino acid ARA.

In one embodiment the spacer lacks the LNGFR serine/threonine-rich stalk. In another embodiment the spacer comprises the LNGFR serine/threonine-rich stalk.

The spacer may comprise or consist of a sequence of SEQ ID NO: 1 or a sequence having at least 85%, 90%, 95%, 96%, 97%, 98% or 99% identity to SEQ ID NO: 1.

The spacer may comprise or consist of a sequence of SEQ ID NO: 3 or a sequence having at least 85%, 90%, 95%, 96%, 97%, 98% or 99% identity to SEQ ID NO: 3.

The spacer may comprise or consist of a sequence of SEQ ID NO: 5 or a sequence having at least 85%, 90%, 95%, 96%, 97%, 98% or 99% identity to SEQ ID NO: 5.

The spacer may comprise or consist of a sequence of SEQ ID NO: 1 or a sequence having at least 85%, 90%, 95%, 96%, 97%, 98% or 99% identity to SEQ ID NO: 7.

The spacer may confer properties to the CAR such that it allows for immunoselection of cells, preferably T-cells, expressing said CAR.

The CAR of the present invention (comprising the spacer referred to herein) preferably enables T-cells expressing the CAR to proliferate in the presence of cells expressing the antigen for which the CAR is designed.

The CAR of the present invention (comprising the spacer referred to herein) preferably enables T-cells expressing the CAR to mediate therapeutically significant anti-cancer effects against a cancer that the CAR is designed to target.

The CAR of the present invention (comprising the spacer referred to herein) is preferably suitable for facilitating immunoselection of cells transduced with said CAR.

The CAR of the present invention comprising the LNGFR-based spacer avoids activation of unwanted and potentially toxic off-target immune responses and allows CAR-expressing T cells to persist in vivo without being prematurely cleared by the host immune system.

As mentioned below, the present invention also encompasses the use of variants, derivatives, homologues and fragments of the spacer elements described herein.

Derivatives and Fragments

In addition to the specific proteins, peptides and nucleotides mentioned herein, the present invention also encompasses the use of derivatives and fragments thereof.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide retains the desired function.

Typically, amino acid substitutions may be made, for example from 1, 2 or 3 to 10 or 20 substitutions provided that the modified sequence retains the required activity or ability. Amino acid substitutions may include the use of non-naturally occurring analogues.

Proteins or peptides used in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R H |
| AROMATIC | | F W Y |

The derivative may be a homolog. The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 65%, 75%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

A homologous sequence may include a nucleotide sequence which may be at least 50%, 55%, 65%, 75%, 85% or 90% identical, preferably at least 95% or 97% or 99% identical to the subject sequence. Although homology can also be considered in terms of similarity, in the context of the present invention it is preferred to express homology in terms of sequence identity.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) *Nucleic Acids Res.* 12: 387). Examples of other software that can perform sequence comparisons include, but are not limited to, the BLAST package (see Ausubel et al. (1999) *ibid*—Ch. 18), FASTA (Atschul et al. (1990) *J. Mol. Biol.* 403-410) and the GENEWORKS suite of comparison tools. Both BLAST and FASTA are available for offline and online searching (see Ausubel et al. (1999) *ibid*, pages 7-58 to 7-60). However, for some applications, it is preferred to use the GCG Bestfit program. Another tool, called BLAST 2 Sequences is also available for comparing protein and nucleotide sequences (see *FEMS Microbiol. Lett.* (1999) 174: 247-50; *FEMS Microbiol. Lett.* (1999) 177: 187-8).

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percentage homology, preferably percentage sequence identity. The software typically does this as part of the sequence comparison and generates a numerical result.

Fragments typically refer to a selected region of the polypeptide or polynucleotide that is of interest functionally. "Fragment" thus refers to an amino acid sequence that is a portion of a full length polypeptide or a nucleic acid sequence that is a portion of a full-length polynucleotide. Since fragments are of interest functionally e.g., retain the desired functionality, they will therefore exclude e.g. a single amino acid or a single nucleic acid.

Such derivatives and fragments may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Polynucleotides

Polynucleotides of the invention may comprise DNA or RNA. They may be single-stranded or double-stranded. It will be understood by a skilled person that numerous different polynucleotides can encode the same polypeptide as a result of the degeneracy of the genetic code. In addition, it is to be understood that the skilled person may, using routine techniques, make nucleotide substitutions that do not affect the polypeptide sequence encoded by the polynucleotides of the invention to reflect the codon usage of any particular host organism in which the polypeptides of the invention are to be expressed.

The polynucleotides may be modified by any method available in the art. Such modifications may be carried out in order to enhance the in vivo activity or lifespan of the polynucleotides of the invention.

Polynucleotides such as DNA polynucleotides may be produced recombinantly, synthetically or by any means available to those of skill in the art. They may also be cloned by standard techniques.

Longer polynucleotides will generally be produced using recombinant means, for example using polymerase chain reaction (PCR) cloning techniques. This will involve making a pair of primers (e.g. of about 15 to 30 nucleotides) flanking the target sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture with an agarose gel) and recovering the amplified DNA. The primers may be designed to contain suitable restriction enzyme recognition sites so that the amplified DNA can be cloned into a suitable vector.

Codon Optimisation

The polynucleotides used in the present invention may be codon-optimised. Codon optimisation has previously been described in WO 1999/41397 and WO 2001/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Vectors

A vector is a tool that allows or facilitates the transfer of an entity from one environment to another. In accordance with the present invention, and by way of example, some vectors used in recombinant nucleic acid techniques allow entities, such as a segment of nucleic acid (e.g. a heterologous DNA segment, such as a heterologous cDNA segment), to be transferred into a target cell. Vectors may be non-viral or viral. Examples of vectors used in recombinant nucleic acid techniques include, but are not limited to, plasmids, mRNA molecules (e.g. in vitro transcribed mRNAs), chromosomes, artificial chromosomes and viruses. The vector may also be, for example, a naked nucleic acid (e.g. DNA). In its simplest form, the vector may itself be a nucleotide of interest.

The vectors used in the invention may be, for example, plasmid, mRNA or virus vectors and may include a promoter for the expression of a polynucleotide and optionally a regulator of the promoter.

Vectors comprising polynucleotides of the invention may be introduced into cells using a variety of techniques known in the art, such as transformation and transduction. Several techniques are known in the art, for example infection with recombinant viral vectors, such as retroviral, lentiviral, adenoviral, adeno-associated viral, baculoviral and herpes simplex viral vectors; direct injection of nucleic acids and biolistic transformation.

Non-viral delivery systems include but are not limited to DNA transfection methods. Here, transfection includes a process using a non-viral vector to deliver a gene to a target cell.

Typical transfection methods include electroporation, DNA biolistics, lipid-mediated transfection, compacted DNA-mediated transfection, liposomes, immunoliposomes, lipofectin, cationic agent-mediated transfection, cationic facial amphiphiles (CFAs) (*Nat. Biotechnol.* (1996) 14: 556) and combinations thereof.

Retroviral Vectors

In one embodiment, the vector used in the present invention is a retrovirus-based vector which has been genetically engineered so that it cannot replicate and produce progeny infectious virus particles once the virus has entered the target cell. There are many retroviruses that are widely used for delivery of genes both in tissue culture conditions and in living organisms. Examples include and are not limited to murine leukemia virus (MLV), human immunodeficiency virus (HIV-1), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses. A detailed list of retroviruses may be found in Coffin et al., 1997, "retroviruses", Cold Spring Harbour Laboratory Press Eds: J M Coffin, S M Hughes, H E Varmus pp 758-763.

The basic structure of a retrovirus genome is a 5' LTR and a 3' LTR, between or within which are located a packaging signal to enable the genome to be packaged, a primer binding site, integration sites to enable integration into a host cell genome and gag, pol and env genes encoding the packaging components—these are polypeptides required for the assembly of viral particles. More complex retroviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration, and transcription. LTRs also serve as enhancer-promoter sequences and can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

In a defective retroviral vector genome gag, pol and env may be absent or not functional. The R regions at both ends of the RNA are repeated sequences. U5 and U3 represent unique sequences at the 5' and 3' ends of the RNA genome respectively.

More preferably, the viral vector is a targeted vector, that is it has a tissue tropism which is altered compared to the native virus, so that the vector is targeted to particular cells. This may be achieved by modifying the retroviral Env protein. Preferably the envelope protein is a non-toxic envelope or an envelope which may be produced in non-toxic amounts within the primary target cell, such as for example a MMLV amphotropic envelope or a modified amphotropic envelope.

Preferably the envelope is one which allows transduction of human cells. Examples of suitable env genes include, but are not limited to, VSV-G, a MLV amphotropic env such as the 4070A env, the RD114 feline leukaemia virus env or haemagglutinin (HA) from an influenza virus. The Env protein may be one which is capable of binding to a receptor on a limited number of human cell types and may be an engineered envelope containing targeting moieties. The env and gag-pol coding sequences are transcribed from a promoter and optionally an enhancer active in the chosen packaging cell line and the transcription unit is terminated by a polyadenylation signal. For example, if the packaging cell is a human cell, a suitable promoter-enhancer combination is that from the human cytomegalovirus major immediate early (hCMV-MIE) gene and a polyadenylation signal from SV40 virus may be used. Other suitable promoters and polyadenylation signals are known in the art.

MLV

Preferably, the retroviral vector used in the present invention is an Murine Leukemia Virus (MLV) vector. Retroviral vectors derived from the amphotropic Moloney murine leukemia virus (MLV-A) are commonly used in clinical protocols worldwide. These viruses use cell surface phosphate transporter receptors for entry and then permanently integrate into proliferating cell chromosomes. The genes are then maintained for the lifetime of the cell. Gene activity on MLV based constructs are easy to control and can be effective over a long time. Clinical trials conducted with these MLV-based systems have shown them to be well tolerated with no adverse side effects.

An example of an MLV vector for use in the present invention is a vector derived from SFCMM-3, which carries both the suicide gene HSV-tk and the marker gene ΔLNGFR (Verzeletti 98, Human Gene Therapy 9:2243). The original vector used in the preparation of SFCMM-3 is LXSN (Miller et al. Improved retroviral vectors for gene transfer and expression. BioTechniques 7:980-990, 1989) (Genebank accession #28248). LXSN vector was modified by the insertion of the HSV-tk gene into the unique Hpa I site ("blunt cut"), removal of the neo gene by digestion with Hind III and Nae I, and insertion of the cDNA encoding ΔLNGFR in this site.

Lentiviral Vector

In one embodiment, the vector of the present invention may be a lentiviral vector. Lentivirus vectors are part of a larger group of retroviral vectors. A detailed list of lentiviruses may be found in Coffin et al ("Retroviruses" 1997 Cold Spring Harbour Laboratory Press Eds: J M Coffin, S M Hughes, H E Varmus pp 758-763). In brief, lentiviruses can be divided into primate and non-primate groups. Examples of primate lentiviruses include but are not limited to: the human immunodeficiency virus (HIV), the causative agent of human acquired-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells. In contrast, other retroviruses—such as MLV—are unable to infect non-dividing or slowly dividing cells such as those that make up, for example, muscle, brain, lung and liver tissue. As lentiviruses are able to transduce terminally differentiated/primary cells, the use of a lentiviral screening strategy allows library selection in a primary target non-dividing or slowly dividing host cell.

Adenovirus Vectors

In another embodiment, the vector of the present invention may be an adenovirus vector. The adenovirus is a double-stranded, linear DNA virus that does not go through an RNA intermediate. There are over 50 different human serotypes of adenovirus divided into 6 subgroups based on the genetic sequence homology. The natural target of adenovirus is the respiratory and gastrointestinal epithelia, generally giving rise to only mild symptoms. Serotypes 2 and 5 (with 95% sequence homology) are most commonly used in adenoviral vector systems and are normally associated with upper respiratory tract infections in the young.

Adenoviruses are nonenveloped, regular icosahedrons. A typical adenovirus comprises a 140 nm encapsidated DNA virus. The icosahedral symmetry of the virus is composed of 152 capsomeres: 240 hexons and 12 pentons. The core of the particle contains the 36 kb linear duplex DNA which is covalently associated at the 5' ends with the Terminal Protein (TP) which acts as a primer for DNA replication. The DNA has inverted terminal repeats (ITR) and the length of these varies with the serotype.

The adenovirus is a double stranded DNA nonenveloped virus that is capable of in vivo and in vitro transduction of a broad range of cell types of human and non-human origin. These cells include respiratory airway epithelial cells, hepatocytes, muscle cells, cardiac myocytes, synoviocytes, primary mammary epithelial cells and post-mitotically terminally differentiated cells such as neurons.

Adenoviral vectors are also capable of transducing non dividing cells. This is very important for diseases, such as cystic fibrosis, in which the affected cells in the lung epithelium, have a slow turnover rate. In fact, several trials are underway utilising adenovirus-mediated transfer of cystic fibrosis transporter (CFTR) into the lungs of afflicted adult cystic fibrosis patients.

Adenoviruses have been used as vectors for gene therapy and for expression of heterologous genes. The large (36 kilobase) genome can accommodate up to 8 kb of foreign insert DNA and is able to replicate efficiently in complementing cell lines to produce very high titres of up to $10^{12}$. Adenovirus is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome. Instead, it functions episomally (independently from the host genome) as a linear genome in the host nucleus. Hence the use of recombinant adenovirus alleviates the problems associated with random integration into the host genome.

Pox Viral Vectors

Pox viral vectors may be used in accordance with the present invention, as large fragments of DNA are easily cloned into their genome and recombinant attenuated vaccinia variants have been described (Meyer, et al., 1991; Smith and Moss, 1983).

Examples of pox viral vectors include but are not limited to leporipoxvirus: Upton, et al., 1986, (shope fibroma virus); capripoxvirus: Gershon, et al., 1989, (Kenya sheep-1); orthopoxvirus: Weir, et al., 1983, (vaccinia); Esposito, et al.,1984, (monkeypox and variola virus); Hruby, et al., 1983, (vaccinia); Kilpatrick, et al., 1985, (Yaba monkey tumour virus); avipoxvirus: Binns, et al., (1988) (fowlpox); Boyle, et al., 1987, (fowlpox); Schnitzlein, et al., 1988, (fowlpox, quailpox); entomopox (Lytvyn, et al., 1992.

Poxvirus vectors are used extensively as expression vehicles for genes of interest in eukaryotic cells. Their ease of cloning and propagation in a variety of host cells has led, in particular, to the widespread use of poxvirus vectors for expression of foreign protein and as delivery vehicles for vaccine antigens.

Vaccinia Viral Vectors

The vector of the present invention may be a vaccinia virus vector such as MVA or NYVAC. Most preferred is the vaccinia strain modified virus ankara (MVA) or a strain derived therefrom. Alternatives to vaccinia vectors include avipox vectors such as fowlpox or canarypox known as ALVAC and strains derived therefrom which can infect and express recombinant proteins in human cells but are unable to replicate.

Cells

The invention also provides genetically engineered cells which comprise and stably express the CAR of the invention.

The antigen-specific targeting domains may be capable of specifically binding, in an MHC unrestricted manner, an antigen which is not normally bound by a T-cell receptor in that manner. In one embodiment, the antigen-specific targeting regions comprise target-specific antibodies or functional equivalents or fragments or derivatives thereof. The antigen-specific antibody may be the Fab fragment of the antibody or the single chain variable fragment (scFv) of the antibody.

Genetically engineered cells which may comprise and express the CARs of the invention include, but are not limited to, T-cells, naive T cells, stem cell memory T cells, central memory T cells, effector memory T cells, natural killer cells, hematopoietic stem cells and/or cells capable of giving rise to therapeutically relevant progeny. In an embodiment, the genetically engineered cells are autologous cells. By way of example, individual T-cells of the invention may be CD4+/CD8−, CD4−/CD8+, CD4−/CD8− or CD4+/CD8+. The T-cells may be a mixed population of CD4+/CD8− and CD4−/CD8+ cells or a population of a single clone.

Genetically modified cells may be produced by stably transfecting cells with DNA encoding the CAR of the invention.

Various methods produce stable transfectants which express the CARs of the invention. In one embodiment, a method of stably transfecting and re-directing cells is by electroporation using naked DNA. By using naked DNA, the time required to produce redirected cells may be significantly reduced. Additional methods to genetically engineer cells using naked DNA encoding the CAR of the invention include but are not limited to chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). The transfected cells demonstrating presence of a single integrated un-rearranged vector and expression of the CAR may be expanded ex vivo. In one embodiment, the cells selected for ex vivo expansion are CD8+ and demonstrate the capacity to specifically recognize and lyse antigen-specific target cells.

Viral transduction methods may also be used to generate redirected cells which express the CAR of the invention.

Stimulation of the T-cells by an antigen under proper conditions results in proliferation (expansion) of the cells and/or production of IL-2. The cells comprising the CAR of the invention will expand in number in response to the binding of one or more antigens to the antigen-specific targeting regions of the CAR. The invention also provides a method of making and expanding cells expressing a CAR. The method may comprise transfecting or transducing the cells with the vector expressing the CAR after stimulating the cells with: 1) polyclonal stimuli such as cell-free scaffolds, preferably optimally-sized beads, cointaining at least an activating polipeptide, preferably an antibody, specific for CD3 and an activating polipeptide, preferably an antibody, specific for CD28; 2) tumor cells expressing the target antigen; 3) natural artificial antigen presenting cells, and culturing them with cytokines including IL-2, IL-7, IL-15, IL-21 alone or in combination.

Therapeutic Methods and Pharmaceutical Compositions

There are provided herein methods for treating a disease associated with the antigen targeted by the CAR of the invention in a subject in need thereof. The method comprises administering an effective amount of the CAR, polynucleotide or vector encoding the CAR, or a cell expressing said CAR so as to treat the disease associated with the antigen in the subject.

There is also provided a pharmaceutical composition comprising a CAR of the invention. The CAR of the invention in the composition may be any one or more of a polynucleotide encoding the CAR, a vector encoding the CAR, a protein comprising the CAR or genetically modified cells comprising the CAR.

A pharmaceutical composition is a composition that comprises or consists of a therapeutically effective amount of a pharmaceutically active agent. It preferably includes a pharmaceutically acceptable carrier, diluent or excipient (including combinations thereof). Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s) or solubilising agent(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

EXAMPLES

Example 1

Methods

Generation of LNGFR-spaced CD44v6-CAR.28z Constructs

The sequences of the LNGFR-based spacers were derived from the extracellular portion of the low-affinity nerve growth factor receptor (LNGFR), excluding the signal peptide (P08138, TNR16_HUMAN). The wild-type long (NWL) design contains both the four TNFR cysteine-rich domains and the serine/threonine-rich stalk. The wild-type short (NWS) design comprises only the four TNFR cysteine-rich domains. The mutated long (NML) design contains the four TNFR cysteine-rich domains, the serine/threonine-rich stalk and includes a specific modification in the fourth domain to avoid binding to NGF (Yan et al, *J Biol Chem*, 1991, Jun. 25;266(18):12099-104). The mutated short (NMS) design contains only the four TNFR cysteine-rich domains including the specific modification in the fourth domain. The spacers were synthesized by GENEART, flanked by specific restriction sites (BamH1 and PflMI) to allow the cloning into our original CD44v6−specific, second-generation CAR construct (FIG. 9A; SEQ ID NO: 15) in place of the IgG1 CH2CH3 spacer. All the constructs have been codon-optimized for expression in humans. All the constructs were expressed into SFG-RV backbones (a splicing MoMLV-based retroviral vector commonly used (Riviere et al, *PNAS,* 1995, Jul. 18;92(15):6733-7)).

Spacer LNGFR wild-type long (NWL):

Protein sequence (SEQ ID NO: 1)
KE<u>ACPTGLYTHSGECCKACNLGEGVAQPCGANQTVC</u>PCLDSVTFSDVV SATEPCKPCTECVGLQSMSAPCVEADDAVC<u>R</u>CAYGYYQDETTGRCEACR VCEAGSGLVFSCQDKQNTVCE *ECPDGTYSDEANHVDPCLPCTVCEDTER QLRECTRWADAECEEIPGRWITRSTPPEGSDSTAPSTQEPEAPPEQDLI ASTVAGVVTTVMGSSQPVVTRGTTDN*.

Nucleotide sequence (SEQ ID NO: 2):
<u>AAAGAGGCCTGCCCCACCGGCCTGTACACCCACAGCGGAGAGTGCTGCA</u>

<u>AGGCCTGCAACCTGGGAGAGGGCGTGGCCCAGCCTTGCGGCGCCAATCA</u>

<u>GACCGTGTGCGAGCCCTGCCTGGACAGCGTGACCTTCAGCGACGTGGTG</u>

<u>TCCGCCACCGAGCCCTGCAAGCCTTGCACCGAGTGTGTGGGCCTGCAGA</u>

GCATGAGCGCCCCTGCGTGGAAGCCGACGACGCCGTGTGT<u>AGATGCGC</u>

CTACGGCTACTACCAGGACGAGACAACCGGCAGATGCGAGGCCTGTAGA

GTGTGCGAGGCCGGCAGCGGCCTGGTGTTCAGTTGTCAAGACAAGCAGA

ATACCGTGTGTGAAGAGTGCCCCGACGGCACCTACAGCGACGAGGCCAA

CCACGTGGACCCCTGCCTGCCCTGCACTGTGTGCGAGGACACCGAGCGG

CAGCTGCGCGAGTGCACAAGATGGGCCGACGCCGAGTGCGAAGAG*ATCC CCGGCAGATGGATCACCAGAAGCACCCCCCCTGAGGGCAGCGACAGCAC CGCCCCTAGCACCCAGGAACCTGAGGCCCCTCCCGAGCAGGACCTGATC GCCTCTACAGTGGCCGGCGTGGTGACAACCGTGATGGGCAGCTCTCAGC CCGTGGTGACACGGGGCACCACCGACAAT*.

Spacer LNGFR wild-type short (NWS):

Protein sequence (SEQ ID NO: 3):
KE<u>ACPTGLYTHSGECCKACNLGEGVAQPCGANQTVC</u>PCLDSVTFSDVV SATEPCKPCTECVGLQSMSAPCVEADDAVC<u>R</u>CAYGYYQDETTGRCEACR VCEAGSGLVFSCQDKQNTVCE *ECPDGTYSDEANHVDPCLPCTVCEDTER QLRECTRWADAECEE*

Nucleotide sequence (SEQ ID NO: 4):
<u>AAAGAGGCCTGCCCCACCGGCCTGTACACCCACAGCGGAGAGTGCTGCA</u>

<u>AGGCCTGCAACCTGGGAGAGGGCGTGGCCCAGCCTTGCGGCGCCAATCA</u>

<u>GACCGTGTGCGAGCCCTGCCTGGACAGCGTGACCTTCAGCGACGTGGTG</u>

<u>TCCGCCACCGAGCCCTGCAAGCCTTGCACCGAGTGTGTGGGCCTGCAGA</u>

GCATGAGCGCCCCTGCGTGGAAGCCGACGACGCCGTGTGT<u>AGATGCGC</u>

CTACGGCTACTACCAGGACGAGACAACCGGCAGATGCGAGGCCTGTAGA

GTGTGCGAGGCCGGCAGCGGCCTGGTGTTCAGTTGTCAGGACAAGCAGA

ACACCGTGTGTGAAGAGTGCCCCGACGGCACCTACAGCGACGAGGCCAA

CCACGTGGACCCCTGCCTGCCCTGCACTGTGTGCGAGGACACCGAGCGG

CAGCTGCGCGAGTGCACAAGATGGGCCGACGCCGAGTGCGAGGAA.

Spacer LNGFR mutated long (NML):

Protein sequence (SEQ ID NO: 5):
KE<u>ACPTGLYTHSGECCKACNLGEGVAQPCGANQTVC</u>PCLDSVTFSDVV SATEPCKPCTECVGLQSMSAPCVEADDAVC<u>R</u>CAYGYYQDETTGRCEACR VCEAGSGLVFSCQDKQNTVCE *ECPDGTYSDEAARAADAECEEIPGRWIT RSTPPEGSDSTAPSTQEPEAPPEQDLIASTVAGVVTTVMGSSQPVVTRG TTDN*.

Nucleotide sequence (SEQ ID NO: 6):
<u>AAAGAGGCCTGCCCCACCGGCCTGTACACCCACAGCGGAGAGTGCTGCA</u>

<u>AGGCCTGCAACCTGGGAGAGGGCGTGGCCCAGCCTTGCGGCGCCAATCA</u>

<u>GACCGTGTGCGAGCCCTGCCTGGACAGCGTGACCTTCAGCGACGTGGTG</u>

<u>TCCGCCACCGAGCCCTGCAAGCCTTGCACCGAGTGTGTGGGCCTGCAGA</u>

GCATGAGCGCCCCTGCGTGGAAGCCGACGACGCCGTGTGT<u>AGATGCGC</u>

CTACGGCTACTACCAGGACGAGACAACCGGCAGATGCGAGGCCTGTAGA

GTGTGCGAGGCCGGCAGCGGCCTGGTGTTCAGTTGTCAAGACAAGCAGA

ATACCGTGTGTGAAGAGTGCCCCGACGGCACCTACAGCGACGAAGCCGC

*CAGAGCCGCCGACGCCGAGTGCGAAGAGATCCCCGGCAGATGGATCACC AGAAGCACCCCCCCTGAGGGCAGCGACAGCACCGCCCCTAGCACCCAGG AACCTGAGGCCCCTCCCGAGCAGGACCTGATCGCCTCTACAGTGGCCGG CGTGGTGACAACCGTGATGGGCAGCTCTCAGCCCGTGGTGACACGGGGC ACCACCGACAAT*.

Spacer LNGFR mutated short (NMS):

Protein sequence (SEQ ID NO: 7):
KE<u>ACPTGLYTHSGECCKACNLGEGVAQPCGANQTVC</u>PCLDSVTFSDVV SATEPCKPCTECVGLQSMSAPCVEADDAVC<u>R</u>CAYGYYQDETTGRCEACR VCEAGSGLVFSCQDKQNTVCE *ECPDGTYSDEAARAADAECEE*.

Nucleotide sequence (SEQ ID NO: 8):
<u>AAAGAGGCCTGCCCCACCGGCCTGTACACCCACAGCGGAGAGTGCTGCA</u>

<u>AGGCCTGCAACCTGGGAGAGGGCGTGGCCCAGCCTTGCGGCGCCAATCA</u>

<u>GACCGTGTGCGAGCCCTGCCTGGACAGCGTGACCTTCAGCGACGTGGTG</u>

<u>TCCGCCACCGAGCCCTGCAAGCCTTGCACCGAGTGTGTGGGCCTGCAGA</u>

GCATGAGCGCCCCTGCGTGGAAGCCGACGACGCCGTGTGT<u>AGATGCGC</u>

CTACGGCTACTACCAGGACGAGACAACCGGCAGATGCGAGGCCTGTAGA

GTGTGCGAGGCCGGCAGCGGCCTGGTGTTCAGTTGTCAGGACAAGCAGA

ACACCGTGTGTGAAGAGTGCCCCGACGGCACCTACAGCGACGAGGCCGC

*CCGGGCCGCCGACGCCGAGTGCGAGGAA*.

Legend:
Underlined: TNFR cysteine-rich domain number 1.
Bold: TNFR cysteine-rich domain number 2.
Bold and underlined: TNFR cysteine-rich domain number 3.
Italics: TNFR cysteine-rich domain number 4.
Italics and underlined: Serine/Threonine rich stalk Transduction and Culture Conditions.

T cells were activated with cell-sized CD3/CD28-beads (ClinExVivo, Invitrogen) plus IL-7/IL-15 (5 ng/ml, Pepro-tech) and RV-transduced by two rounds of spinoculation at day 2 and 3 after stimulation. At day 6, beads were removed and T cells cultured in RPMI 1640 (Gibco-BrI) 10% FBS (BioWhittaker) in the presence of IL-7 and IL-15. Surface expression of CH2CH3-spaced, CD44v6-specific CAR constructs (CHW and CHM) was detected with mAbs specific for the IgG1 CH2CH3 spacer (Jackson Laboratories), while surface expression of LNGFR-spaced CD44v6-specific CAR constructs (NWL, NWS, NML and NMS) was analysed using LNGFR-specific mAbs from BD Bioscience (Clone: C40-14579) or from Miltenyi (Clone: ME20.4). Between day 9 and day 15 from activation, CH2CH3-spaced CD44v6-CAR.28z T cells were FACS-sorted using the polyclonal IgG1 CH2CH3-specific mAbs, while LNGFR-spaced CD44v6-CAR.28z T cells were stained with the PE-conjugated, LNGFR-specific mAb C40-14579 and sorted with columns using anti-PE paramagnetic beads (Miltenyi). Post-sorting T-cell expansion has been expressed as fold increase: T-cell number at day x/T-cell number after sorting.

In Vitro Assays to Analyze Specific Recognition.

In co-culture assays, CAR-sorted T cells were cultured with target cells at different E:T ratios. After 4 days, surviving cells were counted and analysed by FACS. T cells transduced with an irrelevant CAR (CD19) were always used as control. Elimination index was calculated as follows: 1—(number of residual target cells in presence of CD44v6.CAR28z+ T cells)/(number of residual target cells in presence of CTR.CAR28z+ T cells). In CFSE-diluting assays, CAR-sorted T cells were loaded with CFSE and stimulated with irradiated (10,000 rad) tumor cells at the E:S ratio of 1:5 or with biologically active concentrations of NGF. After 6 days, T-cell proliferation was measured by FACS by analyzing the percentage of cells that have diluted the CFSE dye.

Xenograft Models of Antitumor Efficacy

Experimental protocols were approved by the Institutional Animal Care and Use Committee (IACUC). For the minimal-residual dsease model, NSG mice (Jackson) were infused i.v. with $1,5 \times 10^6$ THP1 leukemia cells/mouse. Three days after, mice were treated i.v with $5 \times 10^6$ sorted LNGFR-spaced CD44v6-CAR.28z T cells, CH2CH3-spaced CD44v6-CAR.28z T cells or T cells carrying an irrelevant CAR (CD19). T-cell engraftment was monitored weekly by bleeding and FACS analysis. After 7 weeks, mice were sacrificed and their liver analyzed by histopathology and FACS for the presence of THP-1 cells. For the well-established disease model, NSG mice were infused i.v. with $2 \times 10^6$ MM1.S myeloma cells/mouse. Five weeks after, mice were treated i.v with $5 \times 10^6$ sorted LNGFR-spaced CD44v6-CAR.28z T cells, CH2CH3-spaced CD44v6-CAR.28z T cells or T cells carrying an irrelevant CAR (CD19). T-cell engraftment and myeloma progression were monitored weekly by bleeding and FACS analysis (myeloma cells will be discerned from T cells according to the different human CD45/CD3 phenotype). When circulating MM1.S cells exceeded the 30 cells/µl and/or mice manifested clear signs of tumor-related suffering (paralysis or >10% weight loss), mice were euthanized.

Flow Cytometry.

For FACS analysis, we used FITC-, PE-, PerCP-, PE-Cy7-, APC-, APC-Cy7 and Pacific Blue—conjugated antibodies directed to human CD44v6, CD4 (e-Bioscience), CD123, CD19, CD14, CD3, CD8, CD45RA, CD62L, CXCR4, CD127, CD33, CD38, CD45, LNGFR, mouse CD45, 7AAD (BD Biosciences) and IgG1 CH2CH3 (Jackson laboratories). Cells ($2 \times 10^5$) were incubated with antibodies for 15 minutes at 4° C. and washed with PBS 1% FBS. Samples were run through a FACS Canto II flow cytometer (BD Biosciences), and data were analysed with the Flow Jo software (Tree star Inc). Relative Fluorescence Intensity (RFI) was calculated as follows: mean fluorescence intensity of the sample/mean fluorescence intensity of the corresponding isotype control.

Example 2

Generation of LNGFR-spaced CD44v6-CAR.28z Constructs

Figure 1B:
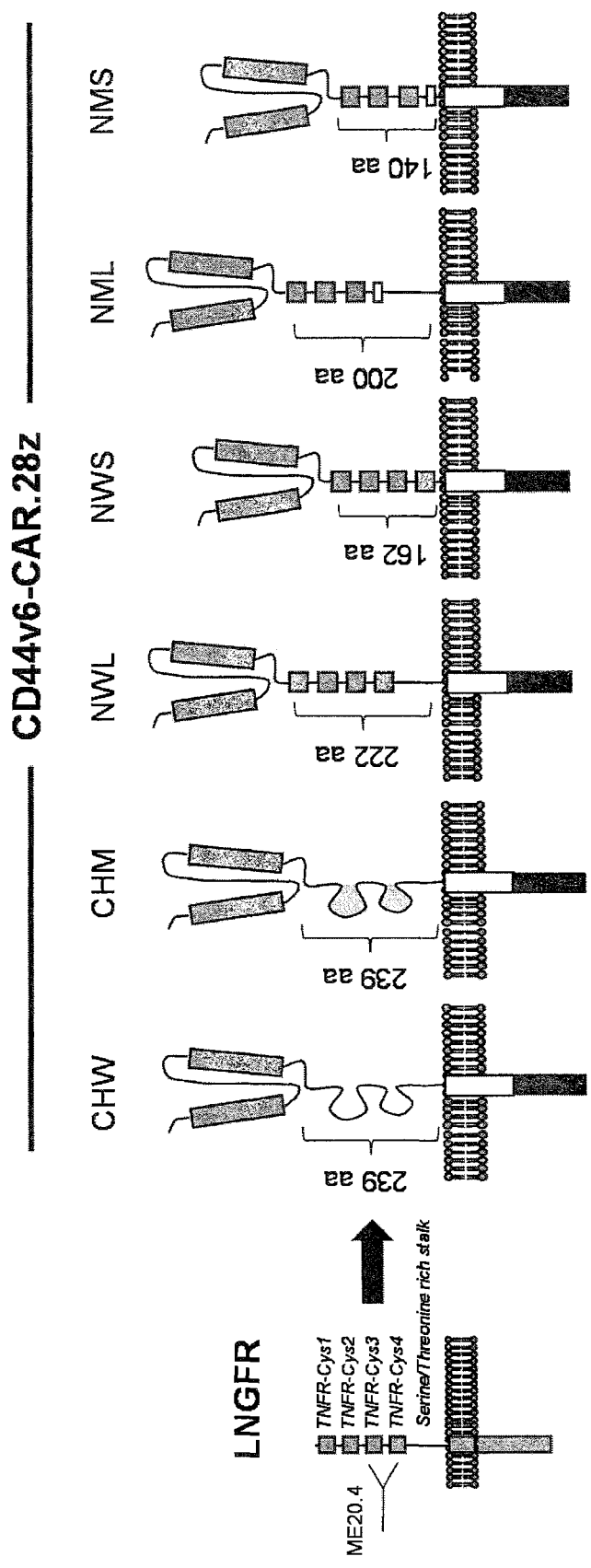

We recently constructed a CD44v6-specific CAR based on the CD3ζ chain combined with a CD28 endo-costimulatory domain (Casucci e al, *Blood* 2013, Nov. 14;122(20): 3461-72). In the extracellular spacer region of this CAR, an IgG1 CH2CH3 spacer was inserted for better targeting of the CD44v6 antigen and for allowing the selection and in vivo tracking of transduced T cells. A serious drawback of CH2CH3-spaced CARs is however their interaction with Fcγ receptors (FcγRs) (Hombach et al, *Gene Ther* 2000, June;7(12):1067-75), potentially leading to non-specific targeting of cells expressing these receptors (e.g. monocytes/macrophages) and/or the in vivo clearance of transduced T cells (FIG. 1A). To circumvent this problem, we substituted the original CH2CH3 spacer with different extracellular domains from the low-affinity nerve growth factor receptor (LNGFR). A truncated version of the LNGFR lacking intracellular signalling components has already been used in the clinic for gene marking of T cells (Bonini et al, *Nat Med*, 2003, April;9(4):367-9; Ciceri et al, *Lancet Oncol*, 2009, May;10(5):489-500). The extracellular portion of the LNGFR is composed of 4 TNFR cysteine-rich regions and a serine/threonine-rich stalk (FIG. 1B). First of all, we generated two CD44v6-CAR.28z constructs: one spaced with the entire extracellular portion of the LNGFR (LNGFR wild type long or NWL) and the other with only the 4 TNFR cysteine-rich regions (LNGFR wild-type short or NWS). To exclude the possibility of antigen-independent activation of LNGFR-spaced construct via the natural ligand NGF, we generated two additional CD44v6-CAR.28z constructs carrying a specific deletion of the fourth TNFR cysteine-rich domain, which is known to abrogate NGF signaling (Yan et al, *J Biol Chem*, 1991, Jun. 25;266(18):12099-104), creating a LNGFR-mutated long isoform or NML and a LNGFR-mutated short isoform or NMS, respectively. As a control, we also generated a CD44v6-CAR.28z construct including a mutated version of the original CH2CH3 spacer (CHM), which is unable to recognize the FcγRI (Hombach et al, *Gene Ther* 2000, June;7(12):1067-75). Remarkably, both the FcγRII and the FcγRIII can use residues besides this common set, suggesting that this mutation does not completely abrogate the binding (Shields et al, *J Biol Chem*, 2001, Mar. 2;276(9):6591-604. Armour et al, *Mol Immunol*, 2003, December;40(9):585-93).

Example 3

Figure 2A:
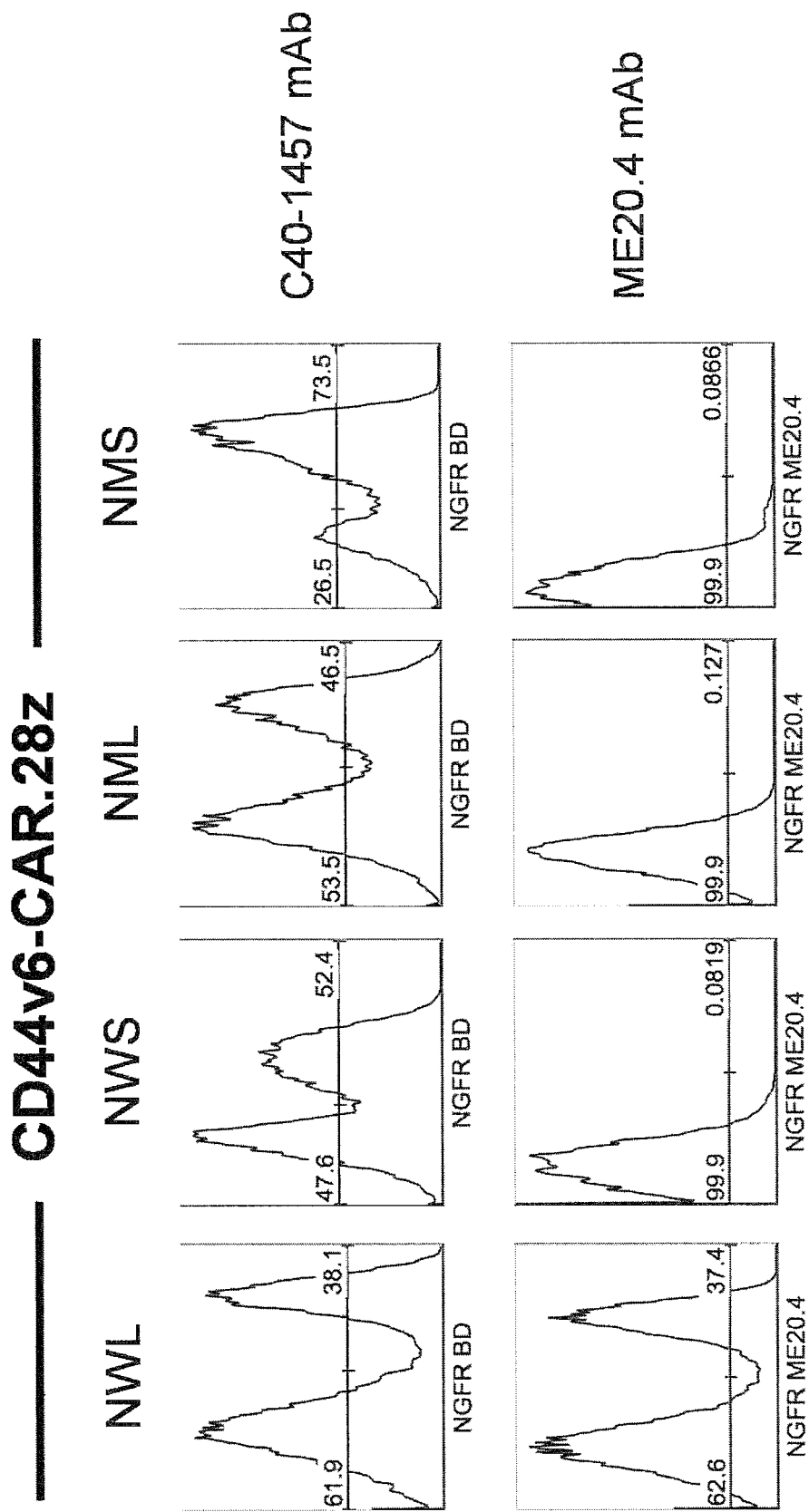
FIG. 2. LNGFR-spaced CD44v6–CAR.28z T cells can be sorted with anti-LNGFR mAbs, efficiently expand in vitro and maintain an early-differentiated phenotype. T cells were activated with CD3/CD28-beads, transduced with retroviral vectors (RVs) encoding for the different LNGFR-spaced CD44v6.CAR28z and cultured with IL-7/IL-15. A. CAR identification on the T-cell surface using the LNGFR-specific mAb C40-1457 (upper plots). CAR identification on the T-cell surface using the LNGFR-specific mAb ME20.4 (lower plots) B. Left: T cells expressing the different LNGFR-spaced CD44v6–CAR.28z after sorting with the C40-1457 mAb and anti-PE beads. Right: expansion kinetics of sorted CH2CH3-spaced and LNGFR-spaced CD44v6–CAR.28z T cells expressed as fold increase. C. Functional differentiation phenotype of the different LNGFR-spaced CD44v6–CAR.28z 15 days after activation. CD45RA+/CD62L+ memory stem T cells, CD45RA−/CD62L+ central memory T cells, CD45RA−/CD62L− effector memory T cells, CD45RA+/CD62L− effector memory T cells RA. Plots and graph are representative of n=4 independent experiments.
Figure 2B:
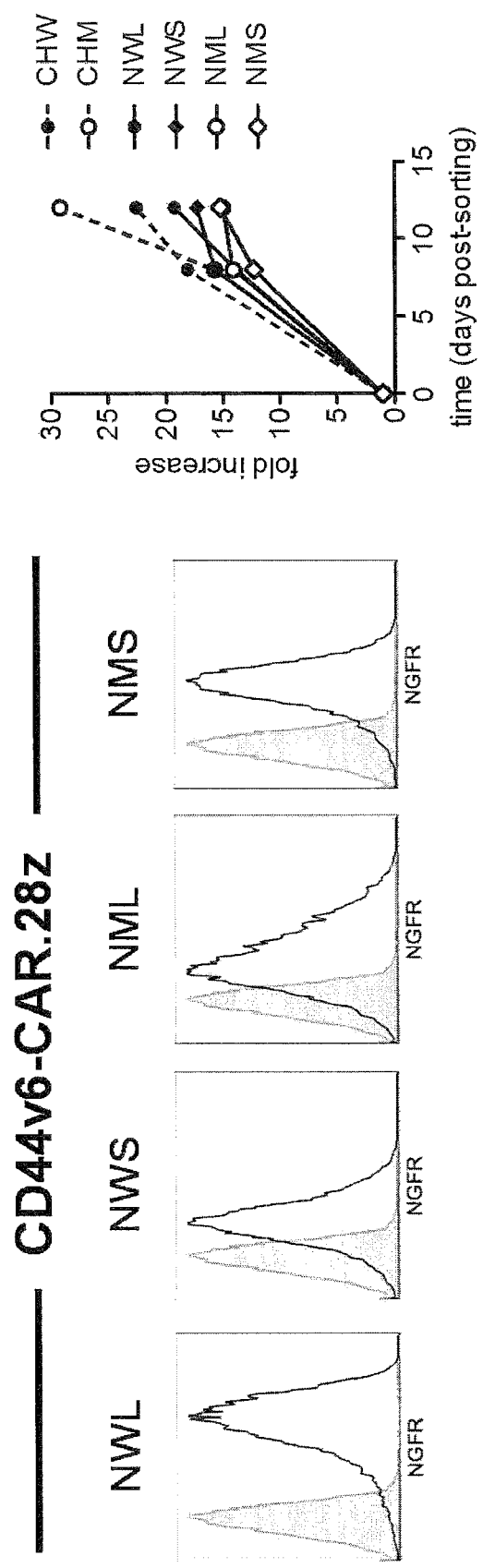
Figure 2C:
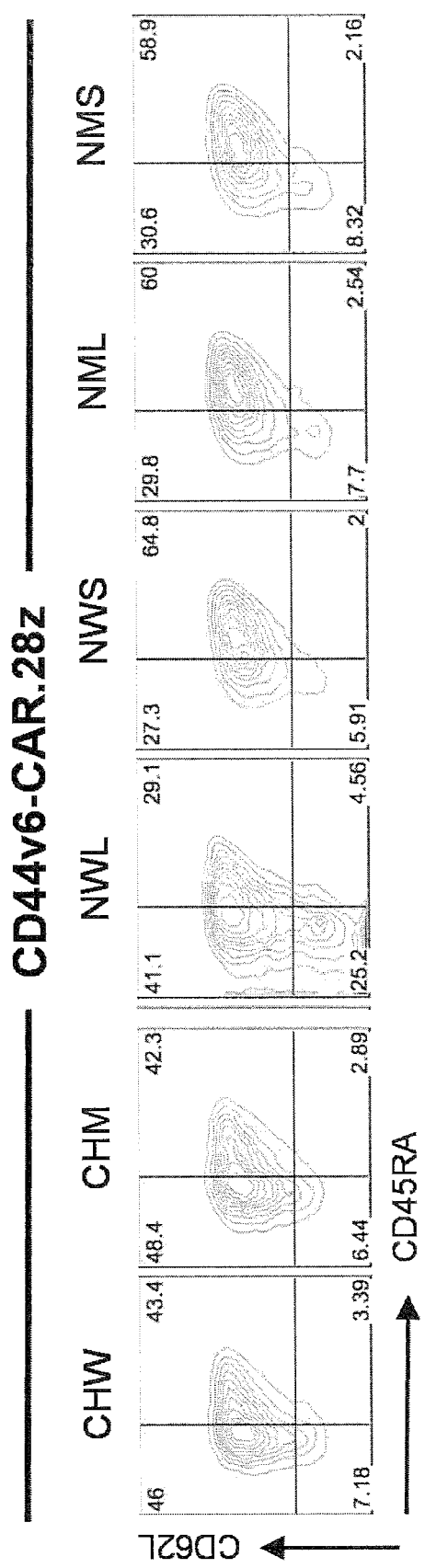

The LNGFR-spaced CD44v6-CAR.28z Constructs Can be Used to Select and Track Transduced T Cells The different LNGFR-spaced CD44v6-CAR.28z constructs were cloned into retroviral vectors (RV) for transducing primary T cells. For transduction, T cells were activated with CD3/CD28-beads plus IL-7/IL-15, according to a protocol that better preserves their functional phenotype (Kaneko et al, Blood, 2009, Jan. 29;113(5):1006-15. Bondanza et al, *Blood* 2011, Jun. 16;117(24):6469-78. Cieri et al, *Blood,* 2013, Jan. 24;121(4):573-84). After transduction, all constructs could be identified on the T-cell surface using the anti-LNGFR mAb C40-1457 (FIG. 2A), indicating that they were correctly processed, mounted on the cell membrane and, most importantly, recognized by anti-NGFR mAbs. As a consequence, the different LNGFR-spaced CD44v6-CAR.28z T cells could be sorted with immunomagnetic beads (FIG. 2B). At a closer look, we found that only the NWL-spaced isoform bound another anti-LNGFR mAb, ME20.4, suggesting that conformational changes dictated by LNGFR spacers of different lengths may control the accessibility of the ME20.4 epitope. Importantly, the expansion kinetics of the different LNGFR-spaced cells was similar to that of CH2CH3-spaced CD44v6-CAR.28z T cells (FIG. 2B), ruling out a potential proliferative advantage induced by extracellular LNGFR sequences mounted on a CAR. At the end of the culture the resulting population was enriched for early-differentiated T cells (FIG. 2C), indicating no interference with the functional differentiation path of bead-activated T cells in the presence of IL-7/IL-15.

Example 4

Figure 3A:
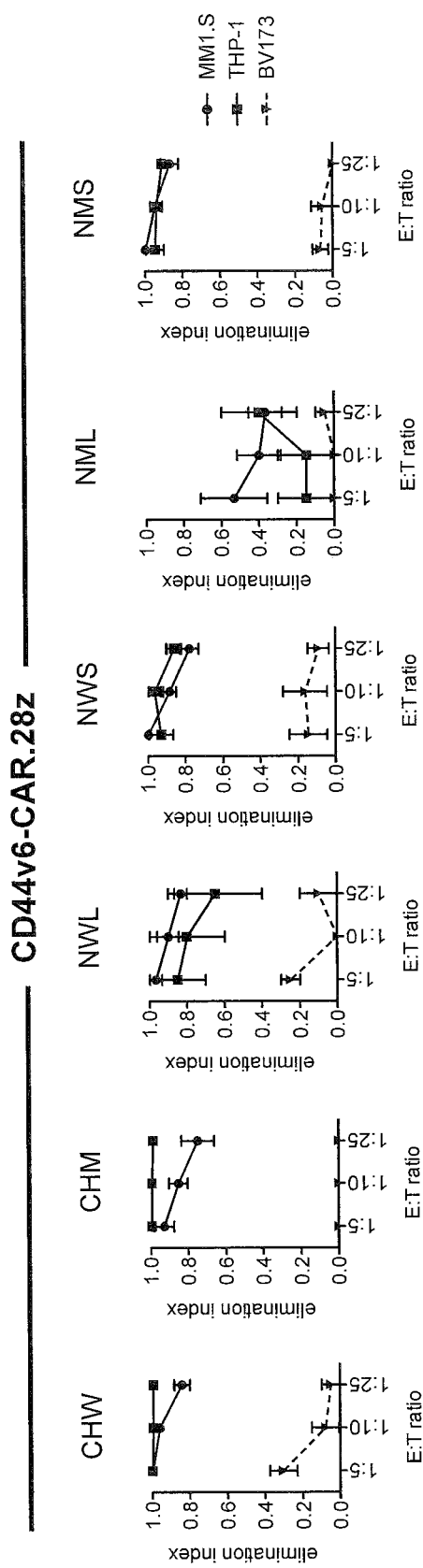
FIG. 3. LNGFR-spaced CD44v6–CAR.28z T cells specifically recognize CD44v6+ve tumor cells in vitro. A. After sorting, the different LNGFR-spaced CD44v6–CAR.28z T cells (NWL, NWS, NML, NMS), CH2CH3-spaced CD44v6–CAR T cells (CHW, CHM) and T cells carrying an irrelevant CAR were cultured with CD44v6+ve MM1.S myeloma cells, CD44v6+ve THP-1 leukemia cells or CD44v6−ve BV-173 lymphoblastoid cells at different E: T ratios. After 4 days, residual tumor cells were counted and analyzed by FACS. The elimination index (see Example Methods) by CD44v6–CAR.28z T cells at different E:T ratio is shown. B. CD44v6–CAR.28z T cells were loaded with the CFSE dye and stimulated with irradiated tumor cell lines at the E:T ratio 1:5. After 6 days, the proliferation of T cells was analyzed by FACS expressed as CFSE-diluting cells. Graphs and plots are representative of n=4 independent experiments.
Figure 3B:
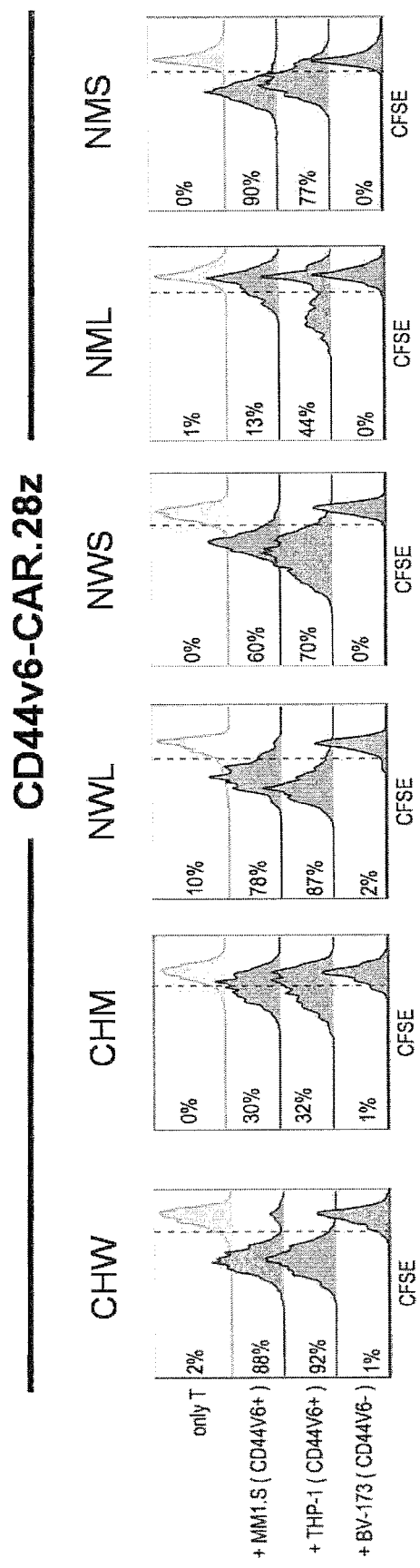

LNGFR-spaced CD44v6-CAR.28z T Cells Retain CD44v6-Specific Recognition, while Losing Non-specific Recognition Mediated by the Interaction with FcγRs To verify the preservation of CD44v6-specific recognition after substituting the original CH2CH3 spacer with LNGFR spacers, LNGFR-spaced CD44v6-CAR.28z T cells were tested in co-culture experiments with CD44v6-expressing tumor cells. Similarly to the CH2CH3-spaced, LNGFR-spaced CD44v6-CAR.28z T cells efficiently eliminated CD44v6+ve (MM1S and THP-1 cell lines), but not CD44v6-ve (BV173 cell lines) tumor cells (FIG. 3A). Moreover, CD44v6-specific recognition was associated with vigorous T-cell expansion (FIG. 3B), suggesting the full preservation of their therapeutic potential of LNGFR-spaced CD44v6-CAR.28z T cells. Therefore, LNGFR-spaced CARs according to the present invention result to be effective against tumor models expressing the specific antigen they are targeted to.

Figure 4:
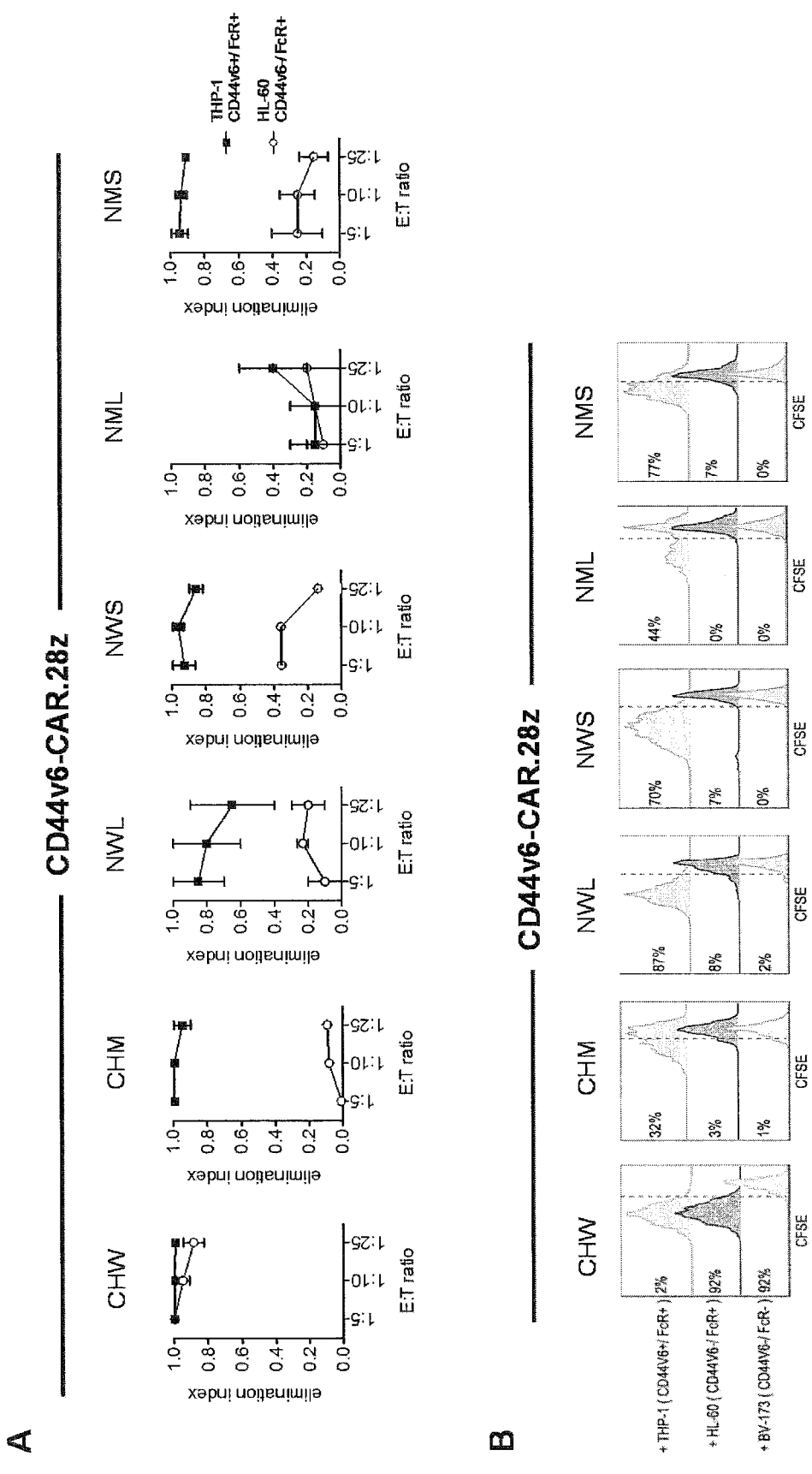
FIG. 4. LNGFR-spaced CD44v6–CAR.28z T cells lack FcRg-mediated recognition. A. After sorting, the different LNGFR-spaced CD44v6–CAR.28z T cells (NWL, NWS, NML, NMS), CH2CH3-spaced CD44v6–CAR T cells (CHW, CHM) and T cells carrying an irrelevant CAR from n=4 healthy donors were cultured with CD44v6+ve/FcRg+ve THP-1 leukemia cells or CD44v6−ve/FcRg+ve HL-60 leukemia cells at different E: T ratios. After 4 days, residual tumor cells were counted and analyzed by FACS. The elimination index (see Example Methods) by CD44v6–CAR.28z T cells at different E:T ratios is shown. B. CD44v6–CAR.28z T cells were loaded with the CFSE dye and stimulated with irradiated THP1, HL60 or CD44v6−ve/FcRg−ve BV-173 lymphoblastoid cells. After 6 days, the proliferation of T cells was analyzed by FACS and expressed as CFSE-diluting cells. Graph and plots are representative of n=4 independent experiments.

To demonstrate lack of non-specific recognition mediated by the interaction with FcRγ, LNGFR-spaced CD44v6-CAR.28z T-cells were co-cultured with CD44v6+ve/FcγRs+ve THP1 leukemia cells or with CD44v6-ve/FcγRs+ve HL-60 leukemia cells. In this system, while the CH2CH3-spaced CD44v6-CAR.28z T cells eliminated both CD44v6+ve THP1 and CD44v6-ve HL-60 cells, LNGFR-spaced CD44v6-CAR.28z CAR T cells specifically eliminated CD44v6+ve THP-1, but not CD44v6-ve HL-60 cells (FIG. 4A). Correspondingly, LNGFR-spaced CD44v6-CAR.28z CAR T cells proliferated in response to CD44v6+ve THP-1, but not to CD44v6-ve HL-60 cells (FIG. 4B). In both systems, the behaviour of the LNGFR-spaced cells was superimposable to that of mutated CH2CH3-spaced CD44v6-CAR.28z CAR T cells, demonstrating abrogation of FcγR-mediated effects.

Therefore, because of the absence of the constant immunoglobulin IgG1 hinge-CH2-CH3 Fc domain as spacer, CARs containing a LNGFR-derived spacer according to the present invention do not bind to IgG Fc gamma receptors thus avoiding activation of unwanted and potentially toxic off-target immune response. Accordingly, LNGFR-spaced CARs are safer than those containing IgG hinge-CH2-CH3.

Figure 5A:
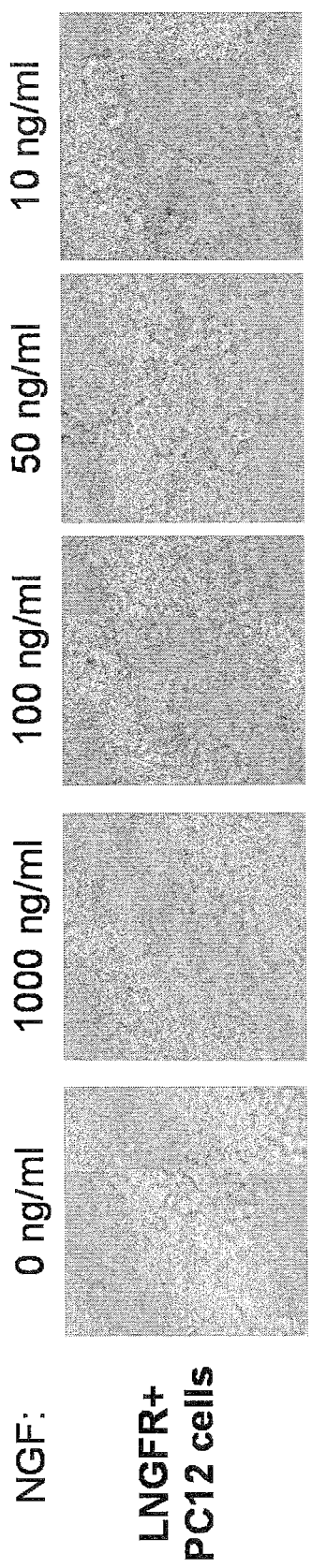
FIG. 5. LNGFR-spaced CD44v6–CAR.28z are not stimulated via soluble NGF. A. After 24 hrs exposure to human recombinant NGF at different concentrations, LNGFR+ve PC-12 neuronal cells were analyzed for dendrite formation by optic microscopy. B. After sorting, the different LNGFR-spaced CD44v6–CAR.28z T cells (NWL, NWS, NML, NMS) and CH2CH3-spaced CD44v6–CAR.28z T cells (CHW, CHM) were loaded with the CFSE dye and exposed to different NGF concentrations. After 4 days, the proliferation of T cells was analyzed by FACS and expressed as CFSE-diluting cells. CFSE dilution after co-culture with CD44v6+ve MM1.S myeloma cells or CD44v6−ve BV-173 lymphoblastoid cells is shown for comparison. Picture and plots are representative of n=2 independent experiments. Graphs depict mean±SD from the two experiments.
Figure 5B:
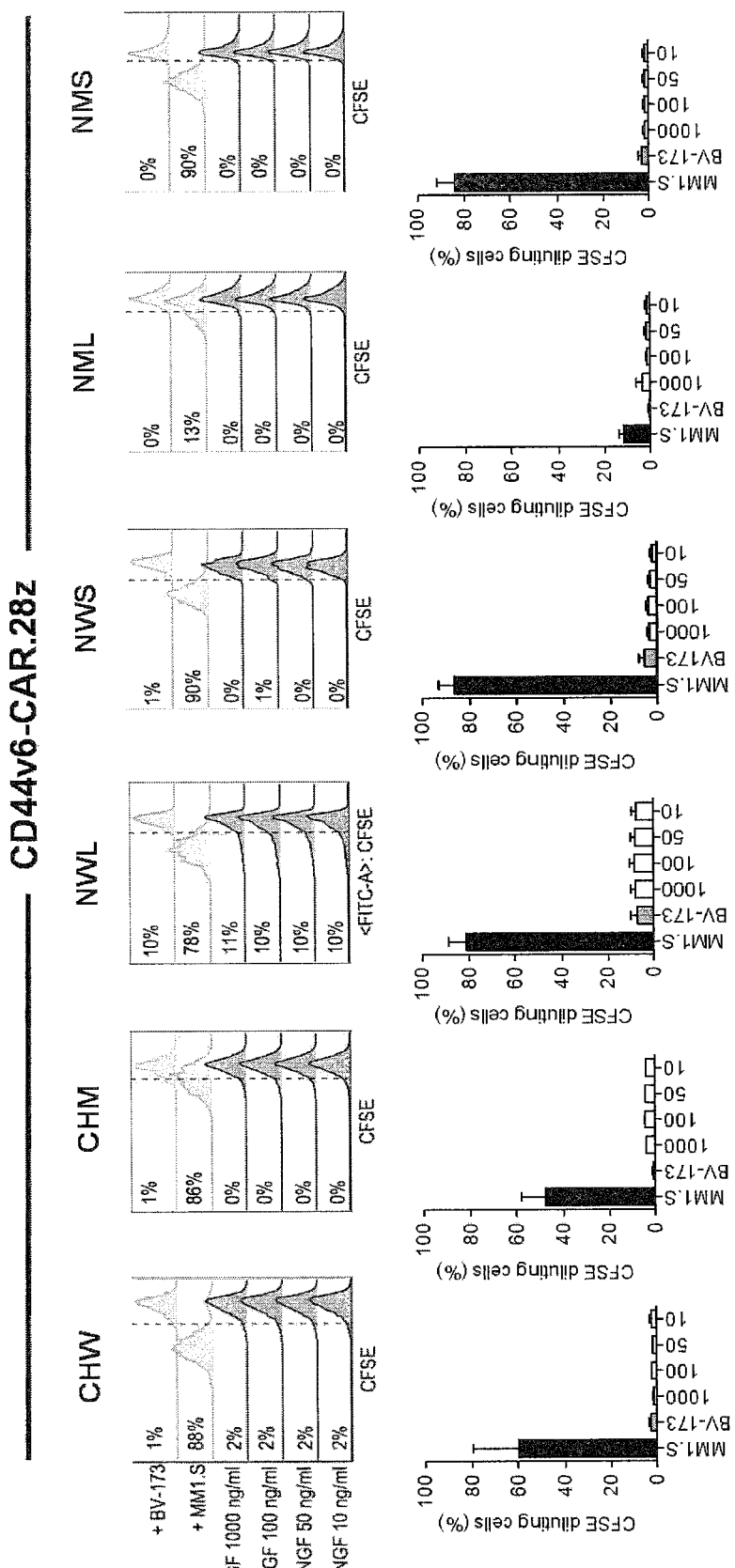

Finally, to rule out antigen-independent stimulation via soluble NGF, LNGFR-spaced CD44v6-CAR28.z T cells were cultured in vitro with NGF. Even at supra-physiological NGF concentrations, known to force the differentiation of the LNGFR-expressing neuronal cell line PC12 (FIG. 5A), the LNGFR-spaced CD44v6-CAR.28z CAR T cells were not induced to proliferate (FIG. 5B), indicating the absence of signaling via soluble NGF.

Example 5

Figure 6A:
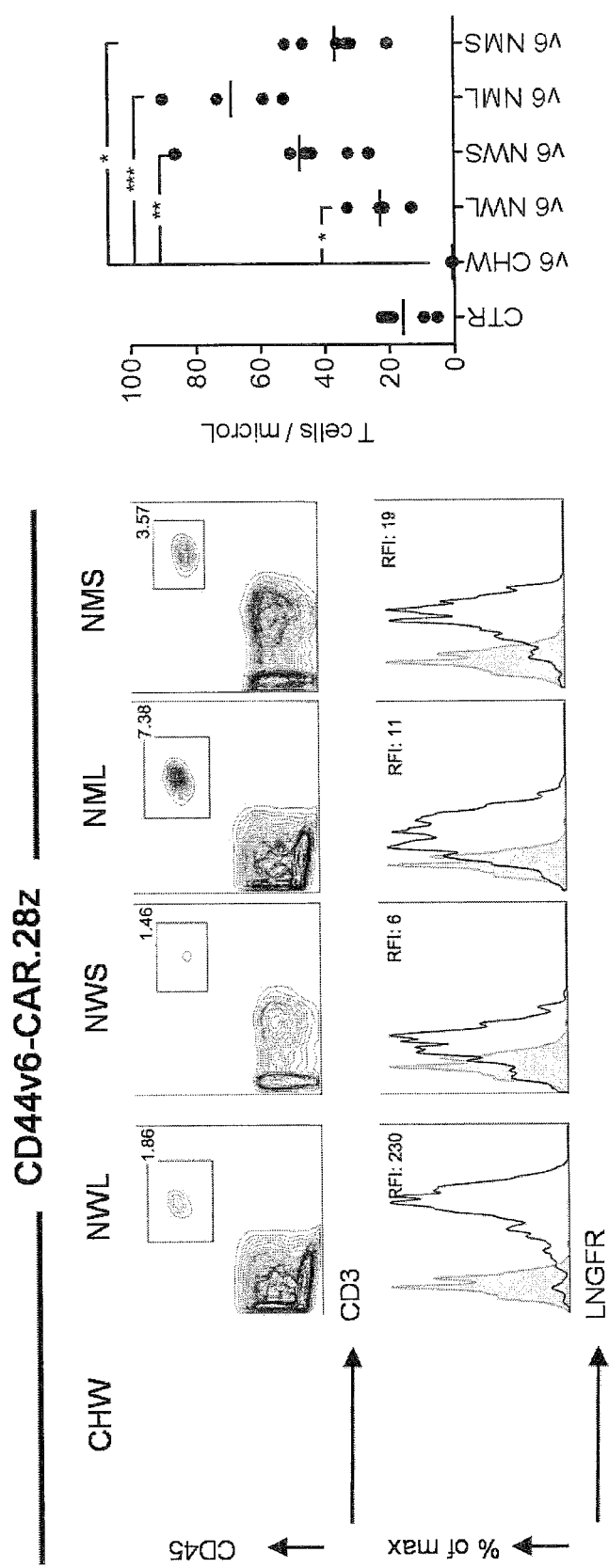
FIG. 6. LNGFR-spaced CD44v6–CAR.28z T cells better expand, persist and mediate superior antileukemia effects in a minimal-residual disease model. NSG mice were infused with CD44v6+ve THP-1 leukemia cells and, after 3 days, treated with the different LNGFR-spaced CD44v6–CAR.28z T cells (NWL, NWS, NML, NMS), CH2CH3-spaced CD44v6–CAR T cells (CHVV) or with T cells expressing an irrelevant CAR (CTR), all sorted to >95% purity. A. Representative plots (left) and all-inclusive graph (right) showing circulating CD44v6–CAR.28z T cells from each mouse three days after infusion. The differently spaced CD44v6–CAR.28z were tracked by FACS after staining with an anti-IgG polyclonal antibody (CTR and CHVV) or the LNGFR-specific mAb, C40-1457 mAb. B. Kinetics of CD44v6–CAR28z T-cell expansion and persistence over time. C. THP1-infiltrated liver weight of treated mice at sacrifice (7 weeks). Dashed zone depicts the range of normal liver weight from age/sex-matched normal NSG mice. Results from a one-way ANOVA test are shown when statistically significant (*P<0.05, P<0.01, *P<0.001).
Figure 7:
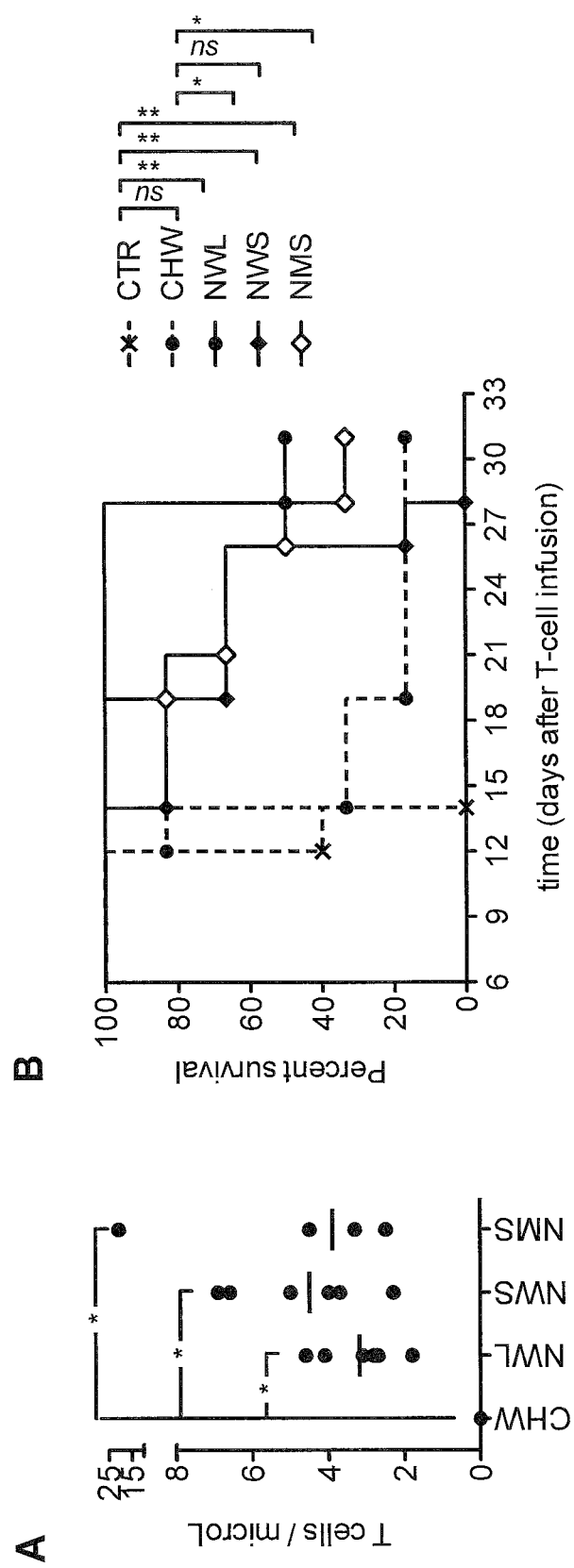
FIG. 7. LNGFR-spaced CD44v6–CAR.28z T cells better expand, persist and mediate superior antimyeloma effects in a well-established disease model. NSG mice were infused with CD44v6+ve MM1.S cells and, after 5 weeks, treated with different LNGFR-spaced CD44v6–CAR.28z T cells (NWL, NWS, NMS), CH2CH3-spaced CD44v6–CAR.28z T cells (CHVV) or with T cells expressing an irrelevant CAR (CTR), all sorted to >95% purity. A. All-inclusive graph (right) showing circulating CD44v6–CAR.28z T cells from each mouse three days after infusion. The differently spaced CD44v6–CAR.28.z were tracked by FACS after staining with an anti-IgG polyclonal antibody (CTR and CHVV) or the LNGFR-specific mAb C40-1457 mAb. B. Kaplan-Meyer survival curves of treated mice. Results from a Log-Rank test comparing the different conditions are shown (ns: non-significant, *P<0.05, ***P<0.001).

LNGFR-spaced CD44v6-CAR.28z T Cells Better Persist in Vivo and Mediate Superior Antitumor Effects After demonstrating effective and specific recognition in vitro, LNGFR-spaced CD44v6-CAR.28z T cells were challenged for antitumor activity in vivo, first in a minimal-residual disease and then in a well-established disease (WED) model. In the first model, NSG mice were infused with THP-1 leukemia cells and after three days treated with CH2CH3-spaced or the different LNGFR-spaced CD44v6-CAR.28z T cells. The different LNGFR-spaced CD44v6-CAR.28z T cells better expanded (FIG. 6A) and persisted (FIG. 6B) than CH2CH3-spaced CD44v6-CAR.28z T cells. Accordingly, LNGFR-spaced CD44v6-CAR.28z T cells appear to mediate superior antitumor effects, as demonstrated by better normalization of THP1-infiltrated liver weight compared to mice infused with CH2CH3-spaced CD44v6-CAR.28z T cells (FIG. 6C). In the second well-established disease model, NSG mice were infused with CD44v6-expressing MM1.S myeloma cells, and after 5 weeks, when the tumor had already colonized the bone marrow, treated with CH2CH3-spaced or the different LNGFR-spaced CD44v6-CAR.28z T cells. CD44v6-CAR.28z T cells carrying the NML isoform were not included. In this more stringent model, while CH2CH3-spaced CD44v6-CAR.28z T cells barely engrafted and did not mediate any significant antitumor effect, the different LNGFR-spaced CD44v6-CAR.28z T cells expanded (FIG. 7A), persisted and resulted in striking antitumor activity (FIG. 7B).

The ability of LNGFR-spaced CD44v6-CAR.28z T cells mediate superior antitumor activity was further confirmed by the use of a well-established myeloma model with CD44v6+MM1.S cells expressing a secreted luciferase. The presence of this luciferase allows to monitor day-by-day the amount of circulating MM1.S tumor cells in mice treated with the CH2CH3-spaced (v6 CHVV) or with NMS LNGFR-spaced (v6 NMS) CD44v6-CAR.28z T cells. In this challenging model, while CH2CH3-spaced CD44v6-CAR.28z T cells showed the same antitumor activity of the unrelated CAR T cells (CTR), the NMS-spaced CD44v6-CAR.28z T cells are able to keep under control the number of circulating tumor cells up to 21 days (FIG. 7BIS A) and to significantly prolong overall survival (FIG. 7BIS B).

Example 6

Methods

Generation of LNGFR-spaced CD19-CAR.28z and CEA-CAR.28z Constructs

Figure 22:
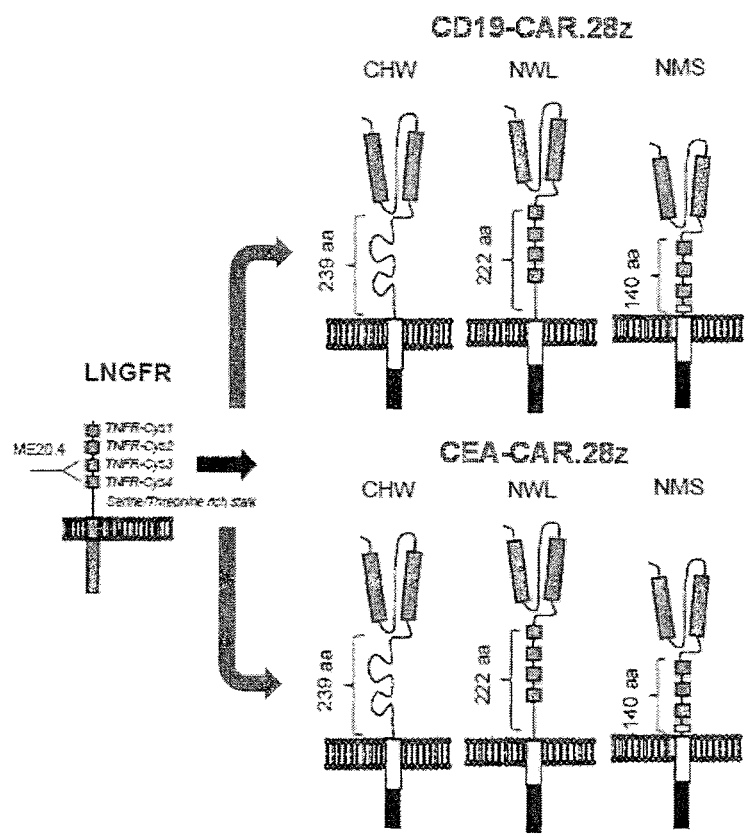
FIG. 22. Generation of different LNGFR-spaced CARs. Structure of the extracellular portion of the low-affinity nerve growth factor receptor (LNGFR) and of the different CAR constructs targeting CD19 and CEA, which have been generated. The CD19/CEA-CAR.28z carrying the wild-type IgG1 CH2CH3 spacer (CH2CH3) are also included. NWL: CD19/CEA-CAR.28z carrying the LNGFR wild-type long spacer (including the 4 TNFR-Cys domains and the stalk). NMS: CD19/CEA-CAR.28z carrying the LNGFR mutated short spacer (including the 4 TNFR-Cys domains with a deletion in the fourth domain). Curly brackets indicate the spacer length expressed in amino acids. Grey: scFv.

A strategy similar to that described in the example 1, was used to generate CD19-specific and CEA-specific CAR constructs (FIG. 22). The following constructs have been generated:

CD19-CAR.28z: carrying a CD19 specific targeting domain, CD3ζ chain combined with a CD28 endo-costimulatory domain and the wild-type IgG1 CH2CH3 spacer (CH2CH3) NWL: CD19-CAR.28z carrying the LNGFR wild-type long spacer (including the 4 TNFR-Cys domains and the stalk)

NMS: CD19-CAR.28z carrying the LNGFR mutated short spacer (including the 4 TNFR-Cys domains with a deletion in the fourth domain)

CEA-CAR.28z: carrying a CEA specific targeting domain, CD3ζ chain combined with a CD28 endo-costimulatory domain and the wild-type IgG1 CH2CH3 spacer (CH2CH3)

NWL: CEA-CAR.28z carrying the LNGFR wild-type long spacer (including the 4 TNFR-Cys domains and the stalk)

NMS: CEA-CAR.28z carrying the LNGFR mutated short spacer (including the 4 TNFR-Cys domains with a deletion in the fourth domain)

Transduction and Culture Conditions.

T cells were activated with cell-sized CD3/CD28-beads (ClinExVivo, Invitrogen) plus IL-7/IL-15 (5 ng/ml, Peprotech) and RV-transduced by two rounds of spinoculation at day 2 and 3 after stimulation. At day 6, beads were removed and T cells cultured in RPMI 1640 (Gibco-BrI) 10% FBS (BioWhittaker) in the presence of IL-7 and IL-15. Surface expression of CH2CH3-spaced, CD19 and CEA-specific CAR constructs (CHVV) was detected with mAbs specific for the IgG1 CH2CH3 spacer (Jackson Laboratories), while surface expression of LNGFR-spaced CAR constructs (NWL and NMS) was analysed using LNGFR-specific mAbs from BD Bioscience (Clone: C40-14579). Between day 9 and day 15 from activation, CH2CH3-spaced CAR.28z T cells were FACS-sorted using the polyclonal IgG1 CH2CH3-specific mAbs, while LNGFR-spaced CAR.28z T cells were stained with the PE-conjugated, LNGFR-specific mAb C40-14579 and sorted with columns using anti-PE paramagnetic beads (Miltenyi).

In vitro Assays to Analyze Specific Recognition.

In co-culture assays, CAR-sorted T cells were cultured with target cells at a 1:10 E:T ratio. After 4 days, surviving cells were counted and analysed by FACS. Elimination index was calculated as follows: 1—(number of residual target cells in presence of CD44v6–4GS2.CAR28z+T cells, CD19.CAR28z+T cells and CEA.CAR28z+T cells)/(number of residual target cells in presence of CTR.CAR28z+T cells). Supernatant of the co-cultures were harvested after 24 hour of incubation and analyzed for cytokine production (IFNy, IL-2 and TNFα) with the CBA assay (BD Biolegend).

Xenograft Models of Antitumor Efficacy

For the minimal-residual disease model, NSG mice (Jackson) were infused i.v. with $1,5 \times 10^6$ ALL-CM leukemia cells/mouse. Three days after, mice were treated i.v with $5 \times 10^6$ sorted LNGFR-spaced (NWL, NMS) CD19-CAR.28z or CD44v6–4GS2.CAR.28z T cells. T-cell engraftment was monitored weekly by bleeding and FACS analysis. After 7 weeks, mice were sacrificed and their bone marrow (BM) analyzed by FACS for the presence of ALL-CM cells with an anti-hCD45 and an anti-hCD19 mAb.

Example 7

Figure 23:
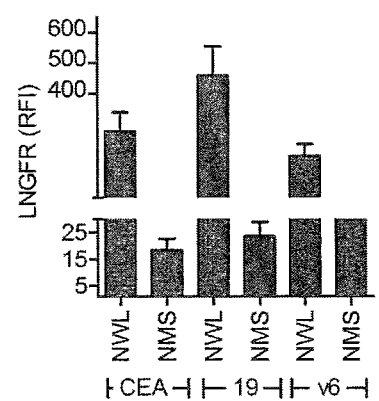
FIG. 23. LNGFR-spaced CD19/CEA-CAR.28z T cells can be stained by the anti-LNGFR mAb. T cells were activated with CD3/CD28-beads, transduced with retroviral vectors (RVs) encoding for the different LNGFR-spaced CD19/CEA.CAR28z, cultured with IL-7/IL-15 and selected with the C40-1457 mAb and anti-PE beads. As positive control, CD44v6–4GS2.CAR28z T cells were produced in the same conditions. CAR identification on the T-cell surface using the LNGFR-specific mAb C40-1457 is shown.

The LNGFR-spaced-CAR.28z Constructs Can be Used to Select and Track Transduced T Cells The different LNGFR-spaced CAR.28z constructs were cloned into retroviral vectors (RV) for transducing primary T cells. For transduction, T cells were activated with CD3/CD28-beads plus IL-7/IL-15, according to a protocol that better preserves their functional phenotype (Kaneko et al, *Blood*, 2009, Jan. 29;113(5):1006-15. Bondanza et al, *Blood* 2011, Jun. 16;117(24):6469-78. Cieri et al, *Blood*, 2013, Jan. 24;121(4):573-84). After transduction, T cells could be sorted with immunomagnetic beads (FIG. 23) indicating that, as shown with CARs targeted to CD44v6 antigen, the LNGFR-derived spacers were correctly processed and mounted on the cell membrane, also in the context of two other CARs specific for the CD19 and the CEA antigens.

Example 8

Figure 24:
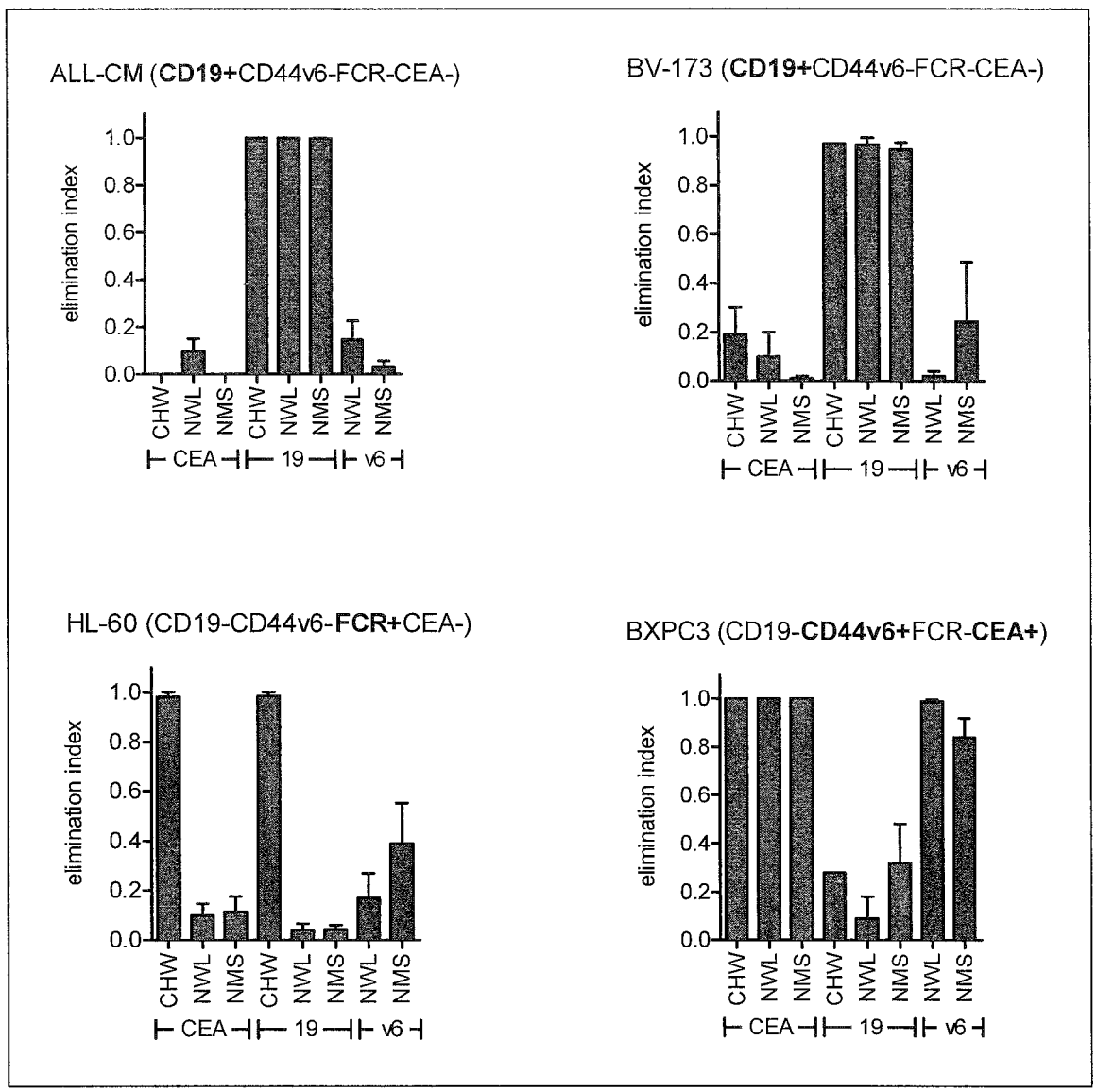
FIG. 24. LNGFR-spaced CD19/CEA-CAR.28z T cells specifically recognize antigen-expressing tumor cells in vitro. A. After sorting, the different LNGFR-spaced CD19/CEA/CD44v6–4GS2-CAR.28z T cells (NWL, NMS), and the CH2CH3-spaced CD19/CEA-CAR T cells (CHVV), were cultured with ALL-CM and HL60 leukemia cells, BV-173 lymphoblastoid cells and BXPC3 carcinoma cells at a 1:10 E:T ratio. After 4 days, residual tumor cells were counted and analyzed by FACS. The elimination index (see Example Methods) by the different CAR.28z T cells is shown. B. Supernatants of the co-cultures described in A, were harvested after 24 hours and analyzed for cytokine production with the CBA assay (Biolegend). Release of IFNy, IL-2, and TNFα upon recognition of target cells is shown.
Figure 24:
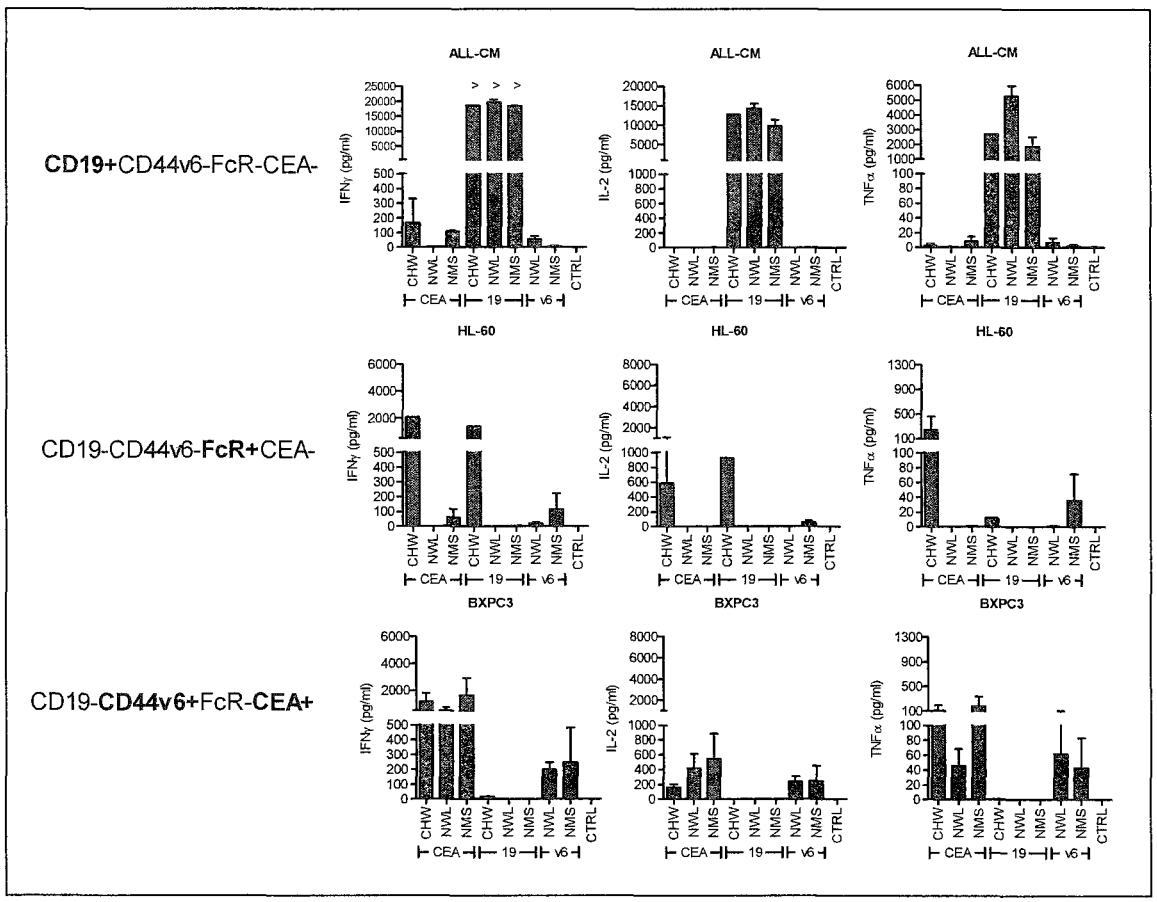

LNGFR-spaced CD19-CAR.28z T Cells, CEA-CAR.28z T and CD44v6–4GS2.CAR.28z T Cells Retain Antigen-specific Recognition, While Losing Non-specific Recognition Mediated by the Interaction with FcγRs To verify the preservation of CD19 and CEA-specific recognition after substituting the original CH2CH3 spacer with LNGFR spacers, LNGFR-spaced CD19-CAR.28z and CEA-CAR.28z T cells were tested in co-culture experiments with antigen-expressing tumor cells. Similarly to the CH2CH3-spaced, LNGFR-spaced CD19-CAR.28z, CEA-CAR.28z T cells and CD44v6–4GS2.CAR.28z T cells efficiently eliminated CD19+, CEA+ and CD44v6+tumor cells respectively, sparing antigen negative tumor cells (FIG. 24A). In particular, LNGFR-spaced CD19-CAR.28z CAR T cells specifically eliminated CD19+ALL-CM and BV-173 cells, but not CD19-HL-60 and BXPC3 cells (FIG. 24A). Similarly, LNGFR-spaced CEA-CAR.28z T cells specifically eliminated CEA+BXPC3 cells, but not CEA–HL-60, ALL-CM and BV-173 cells (FIG. 24 A) and CD44v6–4GS2.CAR.28z T cells specifically eliminated CD44v6+ BXPC3 cells, but not CD44v6–ALL-CM, BV173 and HL-60 cells (FIG. 24 A). Comparable results were obtained when antigen-specific cytokine release (IFNy, 1L2 and TNFα) was evaluated (FIG. 24 B).

CARs Containing LNGFR as Spacer According to the Present Invention, Result to Retain Specificity and Antitumor Effect with Different Antigen Specific Targeting Domains.

To demonstrate lack of non-specific recognition mediated by the interaction with FcRγ, LNGFR-spaced CD19-CAR.28z T-cells, CEA-CAR.28z T-cells and CD44v6–4GS2.CAR.28z T cells were co-cultured with FcγRs+, CD19-CEA–HL-60 cells. In this system, only the CH2CH3-spaced CD19-CAR.28z and CEA–CAR.28z T cells are able to eliminate the HL-60 target cells, thus confirming that the use of LNGFR-based spacer avoid activation of unwanted innate immune response.

Example 12

LNGFR-spaced CD19-CAR.28z T Cells Mediate Antitumor Effects in Vivo

Figure 25:
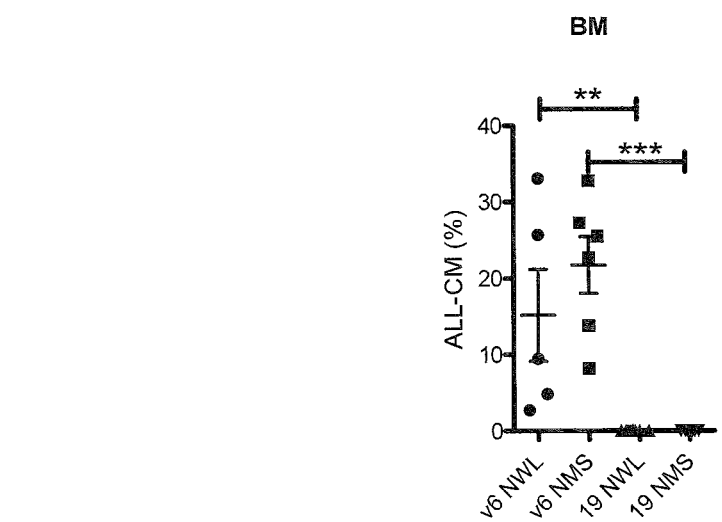
FIG. 25. LNGFR-spaced CD19-CAR.28z T cells mediate antileukemia effects. NSG mice were infused with CD19+ ALL-CM leukemia cells and, after 3 days, treated with the different LNGFR-spaced CD19-CAR.28z T cells (19 NWL and 19 NMS). T cells expressing the unrelated CD44v6–4GS2-CAR.28z (v6 NWL and v6 NMS), are infused as control. All CAR T cells were sorted to >95% purity before infusion. The plot shows the presence of ALL-CM tumor cells in the bone marrow (BM) of each mouse at the sacrifice. The tumor cells were tracked by FACS after staining with an anti-hCD45 and an anti-hCD19 mAb. Results from a T test are shown when statistically significant (*P<0.05, P<0.01, *P<0.001).

After demonstrating effective and specific recognition in vitro, LNGFR-spaced CD19-CAR.28z T cells were challenged for antitumor activity in vivo, in a minimal-residual disease model. NSG mice were infused with ALL-CM leukemia cells and after three days treated with the different LNGFR-spaced (NWL and NMS) CD19-CAR.28z T cells. In this case, LNGFR-spaced (NWL and NMS) CD44v6–4GS2.CAR.28z T cells were used as negative control since the ALL-CM leukemia cells do not express the CD44v6 antigen (FIG. 25). Both LNGFR-spaced CD19-CAR.28z T cells appear to mediate antitumor effects, as demonstrated by lower concentration of ALL-CM cells infiltrating the bone marrow, compared to mice infused with CD44v6–CAR.28z T cells (FIG. 25).

All publications mentioned in the above specification are herein incorporated by reference. Various modifications and variations of the described CARS, polynucleotides, vectors, cells and compositions of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A chimeric antigen receptor (CAR) comprising:
   (i) an antigen-specific targeting domain which targets an antigen selected from the group consisting of isoform 6 of CD44 (CD44v6), CD19, and CEA;
   (ii) an extracellular spacer which comprises at least part of the extracellular domain of human low affinity nerve growth factor receptor (LNGFR), wherein said at least part of the LNGFR is suitable for facilitating immunoselection and identification of cells transduced with said CAR, wherein the extracellular spacer comprises the first three TNFR-Cys domains of LNGFR;
   (iii) a transmembrane domain; and
   (iv) an intracellular signaling domain.

2. A CAR according to claim 1, wherein the spacer lacks the intracellular domain of LNGFR.

3. A CAR according to claim 1, wherein spacer comprises all four TNFR-Cys domains of LNGFR.

4. A CAR according to claim 1, wherein the spacer comprises the fourth TNFR-Cys domain (TNFR-Cys 4) but wherein the following amino acid sequence is removed from said domain: NHVDPCLPCTVCEDTERQLRECTRW (SEQ ID NO: 13) and replaced with the following amino acid sequence: ARA.

5. A CAR according to claim 1, wherein the spacer comprises the serine/threonine-rich stalk of LNGFR.

6. A CAR according to claim 1, wherein the spacer lacks the serine/threonine-rich stalk of LNGFR.

7. A CAR according to claim 1, wherein said spacer comprises the entire extracellular domain of LNGFR.

8. A CAR according to claim 1, wherein the spacer comprises the extracellular domain of LNGFR with the exception of the serine/threonine-rich stalk of said domain.

9. A CAR according to claim 1, wherein the spacer comprises the sequence selected from the group consisting of SEQ ID NO: 1, SEQ ID NO: 3, SEQ ID NO: 5 and SEQ ID NO: 7.

10. A CAR according to claim 1, wherein the spacer consists of a sequence selected from the group consisting of SEQ ID NO: 1, SEQ ID NO: 3, SEQ ID NO: 5 and SEQ ID NO: 7.

11. A CAR according to claim 1, wherein the antigen-specific targeting domain comprises an antibody or fragment thereof.

12. A CAR according to claim 11, wherein the antigen-specific targeting domain is a single chain variable fragment.

13. A CAR according to claim 1, wherein the tumour antigen is isoform 6 of CD44 (CD44v6).

14. A CAR according to claim 1, wherein the transmembrane domain comprises any one or more of a transmembrane domain of a zeta chain of a T cell receptor complex, CD28, CD8a, and combinations thereof.

15. A chimeric antigen receptor (CAR) according to claim 1, further comprising at least one costimulatory domain, wherein the at least one costimulatory domain comprises a costimulatory domain from any one or more of CD28, CD137 (4-1BB), CD134 (OX40), DaplO, CD27, CD2, CD5, ICAM-1, LFA-1, Lck, TNFR-I, TNFR-II, Fas, CD30, CD40, and combinations thereof.

16. A CAR according to claim 15, wherein the intracellular signaling domain comprises an intracellular signaling domain of one or more of a human CD3 zeta chain, FcγRIII, FcεRI, a cytoplasmic tail of a Fc receptor, an immunoreceptor tyrosine-based activation motif (ITAM) bearing cytoplasmic receptors, and combinations thereof.

17. A CAR according to claim 15, wherein the antigen-specific targeting domain targets CD44v6, the transmembrane domain comprises a transmembrane domain of CD28, the intracellular signaling domain comprises an intracellular signaling domain of human CD3 zeta chain, and the costimulatory domain comprises a CD28 costimulatory domain.

18. A chimeric antigen receptor (CAR) comprising:
   (i) an antigen-specific targeting means for targeting a tumour antigen selected from the group consisting of CD44v6, CD19, CEA, and combinations thereof;

(ii) an extracellular spacer which comprises at least part of the extracellular domain of human low affinity nerve growth factor receptor (LNGFR), wherein said at least part of the LNGFR is suitable for facilitating immunoselection and identification of cells transduced with said CAR, wherein the extracellular spacer comprises the first three TNFR-Cys domains of LNGFR;

(iii) a transmembrane domain; and (iv) an intracellular signalling domain.

19. The CAR according to claim 18, further comprising at least one costimulatory domain, wherein the at least one costimulatory domain comprises a costimulatory domain from any one or more of CD28, CD137 (4-1 BB), CD134 (OX40), DapIO, CD27, CD2, CD5, ICAM-1, LFA-1, Lck, TNFR-I, TNFR-II, Fas, CD30, CD40, and combinations thereof.

* * * * *

SEQUENCE LISTING

```
<160> NUMBER OF SEQ ID NOS: 40

<210> SEQ ID NO 1
<211> LENGTH: 222
<212> TYPE: PRT
<213> ORGANISM: Artificial Sequence
<220> FEATURE:
<223> OTHER INFORMATION: Spacer LNGFR wild-type long (NWL)

<400> SEQUENCE: 1

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
        195                 200                 205

Gly Ser Ser Gln Pro Val Val Thr Arg Gly Thr Thr Asp Asn
    210                 215                 220

<210> SEQ ID NO 2
<211> LENGTH: 666
```

<212> TYPE: DNA
<213> ORGANISM: Artificial Sequence
<220> FEATURE:
<223> OTHER INFORMATION: Spacer LNGFR wild-type long (NWL)

<400> SEQUENCE: 2

```
aaagaggcct gccccaccgg cctgtacacc cacagcggag agtgctgcaa ggcctgcaac     60
ctgggagagg gcgtggccca gccttgcggc gccaatcaga ccgtgtgcga gccctgcctg    120
gacagcgtga ccttcagcga cgtggtgtcc gccaccgagc cctgcaagcc ttgcaccgag    180
tgtgtgggcc tgcagagcat gagcgccccc tgcgtggaag ccgacgacgc cgtgtgtaga    240
tgcgcctacg gctactacca ggacgagaca accggcagat gcgaggcctg tagagtgtgc    300
gaggccggca gcggcctggt gttcagttgt caagacaagc agaataccgt gtgtgaagag    360
tgccccgacg gcacctacag cgacgaggcc aaccacgtgg acccctgcct gccctgcact    420
gtgtgcgagg acaccgagcg gcagctgcgc gagtgcacaa gatgggccga cgccgagtgc    480
gaagagatcc ccggcagatg gatcaccaga agcaccccc  ctgagggcag cgacagcacc    540
gcccctagca cccaggaacc tgaggcccct cccgagcagg acctgatcgc ctctacagtg    600
gccggcgtgg tgacaaccgt gatgggcagc tctcagcccg tggtgacacg gggcaccacc    660
gacaat                                                               666
```

<210> SEQ ID NO 3
<211> LENGTH: 162
<212> TYPE: PRT
<213> ORGANISM: Artificial Sequence
<220> FEATURE:
<223> OTHER INFORMATION: Spacer LNGFR wild-type short (NWS)

<400> SEQUENCE: 3

```
Lys Glu Ala Cys Pro Thr Gly Leu Tyr Thr His Ser Gly Glu Cys Cys
 1               5                  10                  15
Lys Ala Cys Asn Leu Gly Glu Gly Val Ala Gln Pro Cys Gly Ala Asn
            20                  25                  30
Gln Thr Val Cys Glu Pro Cys Leu Asp Ser Val Thr Phe Ser Asp Val
        35                  40                  45
Val Ser Ala Thr Glu Pro Cys Lys Pro Cys Thr Glu Cys Val Gly Leu
    50                  55                  60
Gln Ser Met Ser Ala Pro Cys Val Glu Ala Asp Asp Ala Val Cys Arg
65                  70                  75                  80
Cys Ala Tyr Gly Tyr Tyr Gln Asp Glu Thr Thr Gly Arg Cys Glu Ala
                85                  90                  95
Cys Arg Val Cys Glu Ala Gly Ser Gly Leu Val Phe Ser Cys Gln Asp
            100                 105                 110
Lys Gln Asn Thr Val Cys Glu Cys Pro Asp Gly Thr Tyr Ser Asp
        115                 120                 125
Glu Ala Asn His Val Asp Pro Cys Leu Pro Cys Thr Val Cys Glu Asp
    130                 135                 140
Thr Glu Arg Gln Leu Arg Glu Cys Thr Arg Trp Ala Asp Ala Glu Cys
145                 150                 155                 160
Glu Glu
```

<210> SEQ ID NO 4
<211> LENGTH: 486
<212> TYPE: DNA
<213> ORGANISM: Artificial Sequence
<220> FEATURE:

<223> OTHER INFORMATION: Spacer LNGFR wild-type short (NWS)

<400> SEQUENCE: 4

```
aaagaggcct gccccaccgg cctgtacacc cacagcggag agtgctgcaa ggcctgcaac      60
ctgggagagg gcgtggccca gccttgcggc gccaatcaga ccgtgtgcga gccctgcctg     120
gacagcgtga ccttcagcga cgtggtgtcc gccaccgagc cctgcaagcc ttgcaccgag     180
tgtgtgggcc tgcagagcat gagcgccccc tgcgtggaag ccgacgacgc cgtgtgtaga     240
tgcgcctacg gctactacca ggacgagaca accggcagat gcgaggcctg tagagtgtgc     300
gaggccggca gcggcctggt gttcagttgt caggacaagc agaacaccgt gtgtgaagag     360
tgccccgacg gcacctacag cgacgaggcc aaccacgtgg acccctgcct gccctgcact     420
gtgtgcgagg acaccgagcg gcagctgcgc gagtgcacaa gatgggccga cgccgagtgc     480
gaggaa                                                                486
```

<210> SEQ ID NO 5
<211> LENGTH: 200
<212> TYPE: PRT
<213> ORGANISM: Artificial Sequence
<220> FEATURE:
<223> OTHER INFORMATION: Spacer LNGFR mutated long (NML)

<400> SEQUENCE: 5

```
Lys Glu Ala Cys Pro Thr Gly Leu Tyr Thr His Ser Gly Glu Cys Cys
1               5                   10                  15
Lys Ala Cys Asn Leu Gly Glu Gly Val Ala Gln Pro Cys Gly Ala Asn
            20                  25                  30
Gln Thr Val Cys Glu Pro Cys Leu Asp Ser Val Thr Phe Ser Asp Val
        35                  40                  45
Val Ser Ala Thr Glu Pro Cys Lys Pro Cys Thr Glu Cys Val Gly Leu
    50                  55                  60
Gln Ser Met Ser Ala Pro Cys Val Glu Ala Asp Asp Ala Val Cys Arg
65                  70                  75                  80
Cys Ala Tyr Gly Tyr Tyr Gln Asp Glu Thr Thr Gly Arg Cys Glu Ala
                85                  90                  95
Cys Arg Val Cys Glu Ala Gly Ser Gly Leu Val Phe Ser Cys Gln Asp
            100                 105                 110
Lys Gln Asn Thr Val Cys Glu Glu Cys Pro Asp Gly Thr Tyr Ser Asp
        115                 120                 125
Glu Ala Ala Arg Ala Ala Asp Ala Glu Cys Glu Glu Ile Pro Gly Arg
    130                 135                 140
Trp Ile Thr Arg Ser Thr Pro Pro Glu Gly Ser Asp Ser Thr Ala Pro
145                 150                 155                 160
Ser Thr Gln Glu Pro Glu Ala Pro Pro Glu Gln Asp Leu Ile Ala Ser
                165                 170                 175
Thr Val Ala Gly Val Val Thr Thr Val Met Gly Ser Ser Gln Pro Val
            180                 185                 190
Val Thr Arg Gly Thr Thr Asp Asn
        195                 200
```

<210> SEQ ID NO 6
<211> LENGTH: 600
<212> TYPE: DNA
<213> ORGANISM: Artificial Sequence
<220> FEATURE:
<223> OTHER INFORMATION: Spacer LNGFR mutated long (NML)

```
<400> SEQUENCE: 6
aaagaggcct gccccaccgg cctgtacacc cacagcggag agtgctgcaa ggcctgcaac      60
ctgggagagg gcgtggccca gccttgcggc gccaatcaga ccgtgtgcga gccctgcctg     120
gacagcgtga ccttcagcga cgtggtgtcc gccaccgagc cctgcaagcc ttgcaccgag     180
tgtgtgggcc tgcagagcat gagcgccccc tgcgtggaag ccgacgacgc cgtgtgtaga     240
tgcgcctacg gctactacca ggacgagaca accggcagat gcgaggcctg tagagtgtgc     300
gaggccggca gcggcctggt gttcagttgt caagacaagc agaataccgt gtgtgaagag     360
tgccccgacg gcacctacag cgacgaagcc gccagagccg ccgacgccga gtgcgaagag     420
atccccggca gatggatcac cagaagcacc cccctgagg gcagcgacag caccgcccct     480
agcacccagg aacctgaggc ccctcccgag caggacctga tcgcctctac agtggccggc     540
gtggtgacaa ccgtgatggg cagctctcag cccgtggtga cacggggcac caccgacaat     600

<210> SEQ ID NO 7
<211> LENGTH: 140
<212> TYPE: PRT
<213> ORGANISM: Artificial Sequence
<220> FEATURE:
<223> OTHER INFORMATION: Spacer LNGFR mutated short (NMS)

<400> SEQUENCE: 7

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

Glu Ala Ala Arg Ala Ala Asp Ala Glu Cys Glu Glu
    130                 135                 140

<210> SEQ ID NO 8
<211> LENGTH: 420
<212> TYPE: DNA
<213> ORGANISM: Artificial Sequence
<220> FEATURE:
<223> OTHER INFORMATION: Spacer LNGFR mutated short (NMS)

<400> SEQUENCE: 8
aaagaggcct gccccaccgg cctgtacacc cacagcggag agtgctgcaa ggcctgcaac      60
ctgggagagg gcgtggccca gccttgcggc gccaatcaga ccgtgtgcga gccctgcctg     120
gacagcgtga ccttcagcga cgtggtgtcc gccaccgagc cctgcaagcc ttgcaccgag     180
tgtgtgggcc tgcagagcat gagcgccccc tgcgtggaag ccgacgacgc cgtgtgtaga     240
tgcgcctacg gctactacca ggacgagaca accggcagat gcgaggcctg tagagtgtgc     300
```

```
gaggccggca gcggcctggt gttcagttgt caggacaagc agaacaccgt gtgtgaagag    360
tgccccgacg gcacctacag cgacgaggcc gcccgggccg ccgacgccga gtgcgaggaa    420
```

<210> SEQ ID NO 9
<211> LENGTH: 34
<212> TYPE: PRT
<213> ORGANISM: Homo sapiens

<400> SEQUENCE: 9

```
Ala Cys Pro Thr Gly Leu Tyr Thr His Ser Gly Glu Cys Cys Lys Ala
1               5                   10                  15

Cys Asn Leu Gly Glu Gly Val Ala Gln Pro Cys Gly Ala Asn Gln Thr
            20                  25                  30

Val Cys
```

<210> SEQ ID NO 10
<211> LENGTH: 42
<212> TYPE: PRT
<213> ORGANISM: Homo sapiens

<400> SEQUENCE: 10

```
Pro Cys Leu Asp Ser Val Thr Phe Ser Asp Val Val Ser Ala Thr Glu
1               5                   10                  15

Pro Cys Lys Pro Cys Thr Glu Cys Val Gly Leu Gln Ser Met Ser Ala
            20                  25                  30

Pro Cys Val Glu Ala Asp Asp Ala Val Cys
            35                  40
```

<210> SEQ ID NO 11
<211> LENGTH: 39
<212> TYPE: PRT
<213> ORGANISM: Homo sapiens

<400> SEQUENCE: 11

```
Arg Cys Ala Tyr Gly Tyr Tyr Gln Asp Glu Thr Thr Gly Arg Cys Glu
1               5                   10                  15

Ala Cys Arg Val Cys Glu Ala Gly Ser Gly Leu Val Phe Ser Cys Gln
            20                  25                  30

Asp Lys Gln Asn Thr Val Cys
            35
```

<210> SEQ ID NO 12
<211> LENGTH: 41
<212> TYPE: PRT
<213> ORGANISM: Homo sapiens

<400> SEQUENCE: 12

```
Glu Cys Pro Asp Gly Thr Tyr Ser Asp Glu Ala Asn His Val Asp Pro
1               5                   10                  15

Cys Leu Pro Cys Thr Val Cys Glu Asp Thr Glu Arg Gln Leu Arg Glu
            20                  25                  30

Cys Thr Arg Trp Ala Asp Ala Glu Cys
            35                  40
```

<210> SEQ ID NO 13
<211> LENGTH: 25
<212> TYPE: PRT
<213> ORGANISM: Homo sapiens

<400> SEQUENCE: 13

```
Asn His Val Asp Pro Cys Leu Pro Cys Thr Val Cys Glu Asp Thr Glu
1               5                   10                  15

Arg Gln Leu Arg Glu Cys Thr Arg Trp
            20              25
```

<210> SEQ ID NO 14
<211> LENGTH: 427
<212> TYPE: PRT
<213> ORGANISM: Homo sapiens

<400> SEQUENCE: 14

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
            115                 120                 125

Glu Ala Gly Ser Gly Leu Val Phe Ser Cys Gln Asp Lys Gln Asn Thr
130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
            195                 200                 205

Ala Pro Ser Thr Gln Glu Pro Glu Ala Pro Pro Glu Gln Asp Leu Ile
210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
            275                 280                 285

Pro Val Asn Gln Thr Pro Pro Pro Glu Gly Glu Lys Leu His Ser Asp
290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350
```

Gly Ser Ala Gly Asp Thr Trp Arg His Leu Ala Gly Glu Leu Gly Tyr
            355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425

<210> SEQ ID NO 15
<211> LENGTH: 2046
<212> TYPE: DNA
<213> ORGANISM: Artificial Sequence
<220> FEATURE:
<223> OTHER INFORMATION: CD44v6-specific second-generation CAR construct
      sequence, CD44v6-CAR.28z

<400> SEQUENCE: 15

| | | | | | | |
|---|---|---|---|---|---|---|
| atggaagccc | ctgcccagct | gctgttcctg | ctgctgctgt | ggctgcccga | caccaccggc | 60 |
| gagatcgtgc | tgacacagag | ccccgccacc | ctgtctctga | gccctggcga | gagagccacc | 120 |
| ctgagctgta | gcgccagcag | cagcatcaac | tacatctact | ggctgcagca | gaagcccggc | 180 |
| caggccccca | gaatcctgat | ctacctgacc | agcaacctgg | ccagcggcgt | gcccgccaga | 240 |
| ttttctggca | gcggcagcgg | caccgacttc | accctgacca | tcagcagcct | ggaacccgag | 300 |
| gacttcgccg | tgtactactg | cctgcagtgg | tccagcaacc | ccctgacctt | cggcggaggc | 360 |
| accaaggtgg | aaatcaagcg | gggtggtggt | ggttctggtg | gtggtggttc | tggcggcggc | 420 |
| ggctccggtg | gtggtggatc | tgaggtgcag | ctggtggaaa | gcggcggagg | cctggtcaag | 480 |
| cctggcggca | gcctgagact | gagctgtgcc | gccagcggct | tcaccttcag | cagctacgac | 540 |
| atgagctggg | tccgacaggc | tccaggcaag | ggactggaat | gggtgtccac | catcagcagc | 600 |
| ggcggcagct | acacctacta | cctggacagc | atcaagggcc | ggttcaccat | cagccgggac | 660 |
| aacgccaaga | acagcctgta | cctgcagatg | aacagcctgc | gggccgagga | caccgccgtc | 720 |
| tactactgtg | cccggcaggg | cctcgactac | tggggcagag | gcaccctggt | caccgtgtcc | 780 |
| agcggggatc | ccgccagcc | caaatctcct | gacaaaactc | acacatgccc | accgtgccca | 840 |
| gcacctgaac | tcctgggggg | accgtcagtc | ttcctcttcc | ccccaaaacc | caaggacacc | 900 |
| ctcatgatct | cccggacccc | tgaggtcaca | tgcgtggtgg | tggacgtgag | ccacgaagac | 960 |
| cctgaggtca | agttcaactg | gtacgtggac | ggcgtggagg | tgcataatgc | caagacaaag | 1020 |
| ccgcgggagg | agcagtacaa | cagcacgtac | cgtgtggtca | gcgtcctcac | cgtcctgcac | 1080 |
| caggactggc | tgaatggcaa | ggagtacaag | tgcaaggtct | ccaacaaagc | cctcccagcc | 1140 |
| cccatcgaga | aaaccatctc | caaagccaaa | gggcagcccc | gagaaccaca | ggtgtacacc | 1200 |
| ctgcccccat | cccgggatga | gctgaccaag | aaccaggtca | gcctgacctg | cctggtcaaa | 1260 |
| ggcttctatc | ccagcgacat | cgccgtggag | tgggagagca | atgggcaacc | ggagaacaac | 1320 |
| tacaagacca | cgcctcccgt | gctggactcc | gacggctcct | tcttcctcta | cagcaagctc | 1380 |
| accgtggaca | agagcaggtg | gcagcagggg | aacgtcttct | catgctccgt | gatgcatgag | 1440 |
| gctctgcaca | accactacac | gcagaagagc | ctctccctgt | ctccgggtaa | aaagatccc | 1500 |
| aaatttggg | tgctggtggt | ggttggtgga | gtcctggctt | gctatagctt | gctagtaaca | 1560 |

-continued

```
gtggccttta ttattttctg ggtgaggagt aagaggagca ggctcctgca cagtgactac    1620
atgaacatga ctccccgccg ccccgggccc acccgcaagc attaccagcc ctatgcccca    1680
ccacgcgact tcgcagccta tcgctccaga gtgaagttca gcaggagcgc agacgccccc    1740
gcgtaccagc agggccagaa ccagctctat aacgagctca atctaggacg aagagaggag    1800
tacgatgttt tggacaagag acgtggccgg gaccctgaga tggggggaaa gccgagaagg    1860
aagaaccctc aggaaggcct gtacaatgaa ctgcagaaag ataagatggc ggaggcctac    1920
agtgagattg ggatgaaagg cgagcgccgg agggcaagg ggcacgatgg cctttaccag    1980
ggtctcagta cagccaccaa ggacacctac gacgcccttc acatgcaggc cctgccccct    2040
cgctaa                                                              2046
```

<210> SEQ ID NO 16
<211> LENGTH: 681
<212> TYPE: PRT
<213> ORGANISM: Artificial Sequence
<220> FEATURE:
<223> OTHER INFORMATION: CD44v6-CAR.28z protein

<400> SEQUENCE: 16

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110

Asn Pro Leu Thr Phe Gly Gly Gly Thr Lys Val Glu Ile Lys Arg Gly
        115                 120                 125

Gly Gly Gly Ser Gly Gly Gly Ser Gly Gly Gly Ser Gly Gly
    130                 135                 140

Gly Gly Ser Glu Val Gln Leu Val Glu Ser Gly Gly Gly Leu Val Lys
145                 150                 155                 160

Pro Gly Gly Ser Leu Arg Leu Ser Cys Ala Ala Ser Gly Phe Thr Phe
                165                 170                 175

Ser Ser Tyr Asp Met Ser Trp Val Arg Gln Ala Pro Gly Lys Gly Leu
            180                 185                 190

Glu Trp Val Ser Thr Ile Ser Ser Gly Gly Ser Tyr Thr Tyr Tyr Leu
        195                 200                 205

Asp Ser Ile Lys Gly Arg Phe Thr Ile Ser Arg Asp Asn Ala Lys Asn
    210                 215                 220

Ser Leu Tyr Leu Gln Met Asn Ser Leu Arg Ala Glu Asp Thr Ala Val
225                 230                 235                 240

Tyr Tyr Cys Ala Arg Gln Gly Leu Asp Tyr Trp Gly Arg Gly Thr Leu
                245                 250                 255

Val Thr Val Ser Ser Gly Asp Pro Ala Glu Pro Lys Ser Pro Asp Lys
            260                 265                 270
```

```
Thr His Thr Cys Pro Pro Cys Pro Ala Pro Glu Leu Leu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
                340                 345                 350

Val Ser Val Leu Thr Val Leu His Gln Asp Trp Leu Asn Gly Lys Glu
    355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
                420                 425                 430

Ser Asn Gly Gln Pro Glu Asn Asn Tyr Lys Thr Thr Pro Pro Val Leu
    435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Lys Asp Pro Lys Phe Trp Val Leu Val Val Val Gly Gly Val Leu
                500                 505                 510

Ala Cys Tyr Ser Leu Leu Val Thr Val Ala Phe Ile Ile Phe Trp Val
    515                 520                 525

Arg Ser Lys Arg Ser Arg Leu Leu His Ser Asp Tyr Met Asn Met Thr
530                 535                 540

Pro Arg Arg Pro Gly Pro Thr Arg Lys His Tyr Gln Pro Tyr Ala Pro
545                 550                 555                 560

Pro Arg Asp Phe Ala Ala Tyr Arg Ser Arg Val Lys Phe Ser Arg Ser
                565                 570                 575

Ala Asp Ala Pro Ala Tyr Gln Gln Gly Gln Asn Gln Leu Tyr Asn Glu
                580                 585                 590

Leu Asn Leu Gly Arg Arg Glu Glu Tyr Asp Val Leu Asp Lys Arg Arg
    595                 600                 605

Gly Arg Asp Pro Glu Met Gly Gly Lys Pro Arg Arg Lys Asn Pro Gln
610                 615                 620

Glu Gly Leu Tyr Asn Glu Leu Gln Lys Asp Lys Met Ala Glu Ala Tyr
625                 630                 635                 640

Ser Glu Ile Gly Met Lys Gly Glu Arg Arg Arg Gly Lys Gly His Asp
                645                 650                 655

Gly Leu Tyr Gln Gly Leu Ser Thr Ala Thr Lys Asp Thr Tyr Asp Ala
                660                 665                 670

Leu His Met Gln Ala Leu Pro Pro Arg
    675                 680
```

<210> SEQ ID NO 17
<211> LENGTH: 261
<212> TYPE: PRT
<213> ORGANISM: Artificial Sequence
<220> FEATURE:
<223> OTHER INFORMATION: CD44v6-specific single-chain fragment

<400> SEQUENCE: 17

```
Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Ser Ala Ser Ser
            35                  40                  45

Ile Asn Tyr Ile Tyr Trp Leu Gln Gln Lys Pro Gly Gln Ala Pro Arg
50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
                100                 105                 110

Asn Pro Leu Thr Phe Gly Gly Gly Thr Lys Val Glu Ile Lys Arg Gly
            115                 120                 125

Gly Gly Gly Ser Gly Gly Gly Gly Ser Gly Gly Gly Gly Ser Gly Gly
130                 135                 140

Gly Gly Ser Glu Val Gln Leu Val Glu Ser Gly Gly Gly Leu Val Lys
145                 150                 155                 160

Pro Gly Gly Ser Leu Arg Leu Ser Cys Ala Ala Ser Gly Phe Thr Phe
                165                 170                 175

Ser Ser Tyr Asp Met Ser Trp Val Arg Gln Ala Pro Gly Lys Gly Leu
                180                 185                 190

Glu Trp Val Ser Thr Ile Ser Ser Gly Gly Ser Tyr Thr Tyr Tyr Leu
            195                 200                 205

Asp Ser Ile Lys Gly Arg Phe Thr Ile Ser Arg Asp Asn Ala Lys Asn
210                 215                 220

Ser Leu Tyr Leu Gln Met Asn Ser Leu Arg Ala Glu Asp Thr Ala Val
225                 230                 235                 240

Tyr Tyr Cys Ala Arg Gln Gly Leu Asp Tyr Trp Gly Arg Gly Thr Leu
                245                 250                 255

Val Thr Val Ser Ser
            260
```

<210> SEQ ID NO 18
<211> LENGTH: 68
<212> TYPE: PRT
<213> ORGANISM: Homo sapiens

<400> SEQUENCE: 18

```
Phe Trp Val Leu Val Val Gly Gly Val Leu Ala Cys Tyr Ser Leu
1               5                   10                  15

Leu Val Thr Val Ala Phe Ile Ile Phe Trp Val Arg Ser Lys Arg Ser
                20                  25                  30

Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
50                  55                  60
```

Ala Tyr Arg Ser
65

<210> SEQ ID NO 19
<211> LENGTH: 222
<212> TYPE: PRT
<213> ORGANISM: Homo sapiens

<400> SEQUENCE: 19

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
        195                 200                 205

Gly Ser Ser Gln Pro Val Val Thr Arg Gly Thr Thr Asp Asn
    210                 215                 220

<210> SEQ ID NO 20
<211> LENGTH: 113
<212> TYPE: PRT
<213> ORGANISM: Homo sapiens

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 21
<211> LENGTH: 669
<212> TYPE: PRT
<213> ORGANISM: Artificial Sequence
<220> FEATURE:
<223> OTHER INFORMATION: CD44v6-CAR28z with spacer LNGFR wild-type long
      (NWL)

<400> SEQUENCE: 21

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110

Asn Pro Leu Thr Phe Gly Gly Gly Thr Lys Val Glu Ile Lys Arg Gly
        115                 120                 125

Gly Gly Gly Ser Gly Gly Gly Ser Gly Gly Gly Ser Gly Gly
    130                 135                 140

Gly Gly Ser Glu Val Gln Leu Val Glu Ser Gly Gly Gly Leu Val Lys
145                 150                 155                 160

Pro Gly Gly Ser Leu Arg Leu Ser Cys Ala Ala Ser Gly Phe Thr Phe
                165                 170                 175

Ser Ser Tyr Asp Met Ser Trp Val Arg Gln Ala Pro Gly Lys Gly Leu
            180                 185                 190

Glu Trp Val Ser Thr Ile Ser Ser Gly Gly Ser Tyr Thr Tyr Tyr Leu
        195                 200                 205

Asp Ser Ile Lys Gly Arg Phe Thr Ile Ser Arg Asp Asn Ala Lys Asn
    210                 215                 220

Ser Leu Tyr Leu Gln Met Asn Ser Leu Arg Ala Glu Asp Thr Ala Val
225                 230                 235                 240

Tyr Tyr Cys Ala Arg Gln Gly Leu Asp Tyr Trp Gly Arg Gly Thr Leu
                245                 250                 255

Val Thr Val Ser Ser Gly Asp Pro Lys Glu Ala Cys Pro Thr Gly Leu
            260                 265                 270

Tyr Thr His Ser Gly Glu Cys Cys Lys Ala Cys Asn Leu Gly Glu Gly
        275                 280                 285

Val Ala Gln Pro Cys Gly Ala Asn Gln Thr Val Cys Glu Pro Cys Leu
    290                 295                 300

Asp Ser Val Thr Phe Ser Asp Val Val Ser Ala Thr Glu Pro Cys Lys
305                 310                 315                 320

Pro Cys Thr Glu Cys Val Gly Leu Gln Ser Met Ser Ala Pro Cys Val
                325                 330                 335

```
Glu Ala Asp Asp Ala Val Cys Arg Cys Ala Tyr Gly Tyr Tyr Gln Asp
            340                 345                 350

Glu Thr Thr Gly Arg Cys Glu Ala Cys Arg Val Cys Glu Ala Gly Ser
            355                 360                 365

Gly Leu Val Phe Ser Cys Gln Asp Lys Gln Asn Thr Val Cys Glu Glu
    370                 375                 380

Cys Pro Asp Gly Thr Tyr Ser Asp Glu Ala Asn His Val Asp Pro Cys
385                 390                 395                 400

Leu Pro Cys Thr Val Cys Glu Asp Thr Glu Arg Gln Leu Arg Glu Cys
            405                 410                 415

Thr Arg Trp Ala Asp Ala Glu Cys Glu Glu Ile Pro Gly Arg Trp Ile
            420                 425                 430

Thr Arg Ser Thr Pro Pro Glu Gly Ser Asp Ser Thr Ala Pro Ser Thr
            435                 440                 445

Gln Glu Pro Glu Ala Pro Pro Glu Gln Asp Leu Ile Ala Ser Thr Val
        450                 455                 460

Ala Gly Val Val Thr Thr Val Met Gly Ser Ser Gln Pro Val Val Thr
465                 470                 475                 480

Arg Gly Thr Thr Asp Asn Pro Lys Phe Trp Val Leu Val Val Val Gly
            485                 490                 495

Gly Val Leu Ala Cys Tyr Ser Leu Leu Val Thr Val Ala Phe Ile Ile
            500                 505                 510

Phe Trp Val Arg Ser Lys Arg Ser Arg Leu Leu His Ser Asp Tyr Met
        515                 520                 525

Asn Met Thr Pro Arg Arg Pro Gly Pro Thr Arg Lys His Tyr Gln Pro
        530                 535                 540

Tyr Ala Pro Pro Arg Asp Phe Ala Ala Tyr Arg Ser Arg Val Lys Phe
545                 550                 555                 560

Ser Arg Ser Ala Asp Ala Pro Ala Tyr Gln Gln Gly Gln Asn Gln Leu
            565                 570                 575

Tyr Asn Glu Leu Asn Leu Gly Arg Arg Glu Glu Tyr Asp Val Leu Asp
        580                 585                 590

Lys Arg Arg Gly Arg Asp Pro Glu Met Gly Gly Lys Pro Gln Arg Arg
        595                 600                 605

Lys Asn Pro Gln Glu Gly Leu Tyr Asn Glu Leu Gln Lys Asp Lys Met
    610                 615                 620

Ala Glu Ala Tyr Ser Glu Ile Gly Met Lys Gly Glu Arg Arg Arg Gly
625                 630                 635                 640

Lys Gly His Asp Gly Leu Tyr Gln Gly Leu Ser Thr Ala Thr Lys Asp
            645                 650                 655

Thr Tyr Asp Ala Leu His Met Gln Ala Leu Pro Pro Arg
            660                 665

<210> SEQ ID NO 22
<211> LENGTH: 609
<212> TYPE: PRT
<213> ORGANISM: Artificial Sequence
<220> FEATURE:
<223> OTHER INFORMATION: CD44v6-CAR28z with spacer LNGFR wild-type short
      (NWS)

<400> SEQUENCE: 22

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
```

```
                  20                  25                  30
Leu Ser Pro Gly Glu Arg Ala Thr Leu Ser Cys Ser Ala Ser Ser Ser
             35                  40                  45
Ile Asn Tyr Ile Tyr Trp Leu Gln Gln Lys Pro Gly Gln Ala Pro Arg
         50                  55                  60
Ile Leu Ile Tyr Leu Thr Ser Asn Leu Ala Ser Gly Val Pro Ala Arg
 65                  70                  75                  80
Phe Ser Gly Ser Gly Ser Gly Thr Asp Phe Thr Leu Thr Ile Ser Ser
                 85                  90                  95
Leu Glu Pro Glu Asp Phe Ala Val Tyr Tyr Cys Leu Gln Trp Ser Ser
             100                 105                 110
Asn Pro Leu Thr Phe Gly Gly Gly Thr Lys Val Glu Ile Lys Arg Gly
         115                 120                 125
Gly Gly Gly Ser Gly Gly Gly Ser Gly Gly Gly Ser Gly Gly
130                 135                 140
Gly Gly Ser Glu Val Gln Leu Val Glu Ser Gly Gly Leu Val Lys
145                 150                 155                 160
Pro Gly Gly Ser Leu Arg Leu Ser Cys Ala Ala Ser Gly Phe Thr Phe
                 165                 170                 175
Ser Ser Tyr Asp Met Ser Trp Val Arg Gln Ala Pro Gly Lys Gly Leu
             180                 185                 190
Glu Trp Val Ser Thr Ile Ser Ser Gly Gly Ser Tyr Thr Tyr Tyr Leu
         195                 200                 205
Asp Ser Ile Lys Gly Arg Phe Thr Ile Ser Arg Asp Asn Ala Lys Asn
     210                 215                 220
Ser Leu Tyr Leu Gln Met Asn Ser Leu Arg Ala Glu Asp Thr Ala Val
225                 230                 235                 240
Tyr Tyr Cys Ala Arg Gln Gly Leu Asp Tyr Trp Gly Arg Gly Thr Leu
                 245                 250                 255
Val Thr Val Ser Ser Gly Asp Pro Lys Glu Ala Cys Pro Thr Gly Leu
             260                 265                 270
Tyr Thr His Ser Gly Glu Cys Cys Lys Ala Cys Asn Leu Gly Glu Gly
         275                 280                 285
Val Ala Gln Pro Cys Gly Ala Asn Gln Thr Val Cys Glu Pro Cys Leu
     290                 295                 300
Asp Ser Val Thr Phe Ser Asp Val Val Ser Ala Thr Glu Pro Cys Lys
305                 310                 315                 320
Pro Cys Thr Glu Cys Val Gly Leu Gln Ser Met Ser Ala Pro Cys Val
                 325                 330                 335
Glu Ala Asp Asp Ala Val Cys Arg Cys Ala Tyr Gly Tyr Tyr Gln Asp
             340                 345                 350
Glu Thr Thr Gly Arg Cys Glu Ala Cys Arg Val Cys Glu Ala Gly Ser
         355                 360                 365
Gly Leu Val Phe Ser Cys Gln Asp Lys Gln Asn Thr Val Cys Glu Glu
     370                 375                 380
Cys Pro Asp Gly Thr Tyr Ser Asp Glu Ala Asn His Val Asp Pro Cys
385                 390                 395                 400
Leu Pro Cys Thr Val Cys Glu Asp Thr Glu Arg Gln Leu Arg Glu Cys
                 405                 410                 415
Thr Arg Trp Ala Asp Ala Glu Cys Glu Glu Pro Lys Phe Trp Val Leu
             420                 425                 430
Val Val Val Gly Gly Val Leu Ala Cys Tyr Ser Leu Leu Val Thr Val
         435                 440                 445
```

```
Ala Phe Ile Ile Phe Trp Val Arg Ser Lys Arg Ser Arg Leu Leu His
    450                 455                 460

Ser Asp Tyr Met Asn Met Thr Pro Arg Arg Pro Gly Pro Thr Arg Lys
465                 470                 475                 480

His Tyr Gln Pro Tyr Ala Pro Pro Arg Asp Phe Ala Ala Tyr Arg Ser
                485                 490                 495

Arg Val Lys Phe Ser Arg Ser Ala Asp Ala Pro Ala Tyr Gln Gln Gly
            500                 505                 510

Gln Asn Gln Leu Tyr Asn Glu Leu Asn Leu Gly Arg Arg Glu Glu Tyr
        515                 520                 525

Asp Val Leu Asp Lys Arg Arg Gly Arg Asp Pro Glu Met Gly Gly Lys
    530                 535                 540

Pro Gln Arg Arg Lys Asn Pro Gln Glu Gly Leu Tyr Asn Glu Leu Gln
545                 550                 555                 560

Lys Asp Lys Met Ala Glu Ala Tyr Ser Glu Ile Gly Met Lys Gly Glu
                565                 570                 575

Arg Arg Arg Gly Lys Gly His Asp Gly Leu Tyr Gln Gly Leu Ser Thr
            580                 585                 590

Ala Thr Lys Asp Thr Tyr Asp Ala Leu His Met Gln Ala Leu Pro Pro
        595                 600                 605

Arg

<210> SEQ ID NO 23
<211> LENGTH: 647
<212> TYPE: PRT
<213> ORGANISM: Artificial Sequence
<220> FEATURE:
<223> OTHER INFORMATION: CD44v6-CAR28z with spacer LNGFR mutated long
      (NML)

<400> SEQUENCE: 23

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110

Asn Pro Leu Thr Phe Gly Gly Gly Thr Lys Val Glu Ile Lys Arg Gly
        115                 120                 125

Gly Gly Gly Ser Gly Gly Gly Gly Ser Gly Gly Gly Gly Ser Gly Gly
    130                 135                 140

Gly Gly Ser Glu Val Gln Leu Val Glu Ser Gly Gly Gly Leu Val Lys
145                 150                 155                 160

Pro Gly Gly Ser Leu Arg Leu Ser Cys Ala Ala Ser Gly Phe Thr Phe
                165                 170                 175

Ser Ser Tyr Asp Met Ser Trp Val Arg Gln Ala Pro Gly Lys Gly Leu
            180                 185                 190
```

-continued

Glu Trp Val Ser Thr Ile Ser Ser Gly Gly Ser Tyr Thr Tyr Tyr Leu
            195                 200                 205

Asp Ser Ile Lys Gly Arg Phe Thr Ile Ser Arg Asp Asn Ala Lys Asn
    210                 215                 220

Ser Leu Tyr Leu Gln Met Asn Ser Leu Arg Ala Glu Asp Thr Ala Val
225                 230                 235                 240

Tyr Tyr Cys Ala Arg Gln Gly Leu Asp Tyr Trp Gly Arg Gly Thr Leu
                245                 250                 255

Val Thr Val Ser Ser Gly Asp Pro Lys Glu Ala Cys Pro Thr Gly Leu
            260                 265                 270

Tyr Thr His Ser Gly Glu Cys Cys Lys Ala Cys Asn Leu Gly Glu Gly
            275                 280                 285

Val Ala Gln Pro Cys Gly Ala Asn Gln Thr Val Cys Glu Pro Cys Leu
            290                 295                 300

Asp Ser Val Thr Phe Ser Asp Val Val Ser Ala Thr Glu Pro Cys Lys
305                 310                 315                 320

Pro Cys Thr Glu Cys Val Gly Leu Gln Ser Met Ser Ala Pro Cys Val
                325                 330                 335

Glu Ala Asp Asp Ala Val Cys Arg Cys Ala Tyr Gly Tyr Tyr Gln Asp
            340                 345                 350

Glu Thr Thr Gly Arg Cys Glu Ala Cys Arg Val Cys Glu Ala Gly Ser
            355                 360                 365

Gly Leu Val Phe Ser Cys Gln Asp Lys Gln Asn Thr Val Cys Glu Glu
            370                 375                 380

Cys Pro Asp Gly Thr Tyr Ser Asp Glu Ala Arg Ala Ala Asp Ala
385                 390                 395                 400

Glu Cys Glu Glu Ile Pro Gly Arg Trp Ile Thr Arg Ser Thr Pro Pro
                405                 410                 415

Glu Gly Ser Asp Ser Thr Ala Pro Ser Thr Gln Glu Pro Glu Ala Pro
            420                 425                 430

Pro Glu Gln Asp Leu Ile Ala Ser Thr Val Ala Gly Val Val Thr Thr
        435                 440                 445

Val Met Gly Ser Ser Gln Pro Val Val Thr Arg Gly Thr Thr Asp Asn
    450                 455                 460

Pro Lys Phe Trp Val Leu Val Val Val Gly Gly Val Leu Ala Cys Tyr
465                 470                 475                 480

Ser Leu Leu Val Thr Val Ala Phe Ile Ile Phe Trp Val Arg Ser Lys
                485                 490                 495

Arg Ser Arg Leu Leu His Ser Asp Tyr Met Asn Met Thr Pro Arg Arg
            500                 505                 510

Pro Gly Pro Thr Arg Lys His Tyr Gln Pro Tyr Ala Pro Pro Arg Asp
            515                 520                 525

Phe Ala Ala Tyr Arg Ser Arg Val Lys Phe Ser Arg Ser Ala Asp Ala
        530                 535                 540

Pro Ala Tyr Gln Gln Gly Gln Asn Gln Leu Tyr Asn Glu Leu Asn Leu
545                 550                 555                 560

Gly Arg Arg Glu Glu Tyr Asp Val Leu Asp Lys Arg Gly Arg Asp
                565                 570                 575

Pro Glu Met Gly Gly Lys Pro Gln Arg Arg Lys Asn Pro Gln Glu Gly
            580                 585                 590

Leu Tyr Asn Glu Leu Gln Lys Asp Lys Met Ala Glu Ala Tyr Ser Glu
        595                 600                 605

```
Ile Gly Met Lys Gly Glu Arg Arg Gly Lys Gly His Asp Gly Leu
    610                 615                 620
Tyr Gln Gly Leu Ser Thr Ala Thr Lys Asp Thr Tyr Asp Ala Leu His
625                 630                 635                 640
Met Gln Ala Leu Pro Pro Arg
                645

<210> SEQ ID NO 24
<211> LENGTH: 587
<212> TYPE: PRT
<213> ORGANISM: Artificial Sequence
<220> FEATURE:
<223> OTHER INFORMATION: CD44v6-CAR28z with spacer LNGFR mutated short
      (NMS)

<400> SEQUENCE: 24

Met Glu Ala Pro Ala Gln Leu Leu Phe Leu Leu Leu Leu Trp Leu Pro
1               5                   10                  15
Asp Thr Thr Gly Glu Ile Val Leu Thr Gln Ser Pro Ala Thr Leu Ser
            20                  25                  30
Leu Ser Pro Gly Glu Arg Ala Thr Leu Ser Cys Ser Ala Ser Ser Ser
        35                  40                  45
Ile Asn Tyr Ile Tyr Trp Leu Gln Gln Lys Pro Gly Gln Ala Pro Arg
    50                  55                  60
Ile Leu Ile Tyr Leu Thr Ser Asn Leu Ala Ser Gly Val Pro Ala Arg
65                  70                  75                  80
Phe Ser Gly Ser Gly Ser Gly Thr Asp Phe Thr Leu Thr Ile Ser Ser
                85                  90                  95
Leu Glu Pro Glu Asp Phe Ala Val Tyr Tyr Cys Leu Gln Trp Ser Ser
            100                 105                 110
Asn Pro Leu Thr Phe Gly Gly Gly Thr Lys Val Glu Ile Lys Arg Gly
        115                 120                 125
Gly Gly Gly Ser Gly Gly Gly Gly Ser Gly Gly Gly Gly Ser Gly Gly
    130                 135                 140
Gly Gly Ser Glu Val Gln Leu Val Glu Ser Gly Gly Gly Leu Val Lys
145                 150                 155                 160
Pro Gly Gly Ser Leu Arg Leu Ser Cys Ala Ala Ser Gly Phe Thr Phe
                165                 170                 175
Ser Ser Tyr Asp Met Ser Trp Val Arg Gln Ala Pro Gly Lys Gly Leu
            180                 185                 190
Glu Trp Val Ser Thr Ile Ser Ser Gly Gly Ser Tyr Thr Tyr Tyr Leu
        195                 200                 205
Asp Ser Ile Lys Gly Arg Phe Thr Ile Ser Arg Asp Asn Ala Lys Asn
    210                 215                 220
Ser Leu Tyr Leu Gln Met Asn Ser Leu Arg Ala Glu Asp Thr Ala Val
225                 230                 235                 240
Tyr Tyr Cys Ala Arg Gln Gly Leu Asp Tyr Trp Gly Arg Gly Thr Leu
                245                 250                 255
Val Thr Val Ser Ser Gly Asp Pro Lys Glu Ala Cys Pro Thr Gly Leu
            260                 265                 270
Tyr Thr His Ser Gly Glu Cys Cys Lys Ala Cys Asn Leu Gly Glu Gly
        275                 280                 285
Val Ala Gln Pro Cys Gly Ala Asn Gln Thr Val Cys Glu Pro Cys Leu
    290                 295                 300
Asp Ser Val Thr Phe Ser Asp Val Val Ser Ala Thr Glu Pro Cys Lys
305                 310                 315                 320
```

```
Pro Cys Thr Glu Cys Val Gly Leu Gln Ser Met Ser Ala Pro Cys Val
            325                 330                 335

Glu Ala Asp Ala Val Cys Arg Cys Ala Tyr Gly Tyr Tyr Gln Asp
            340                 345                 350

Glu Thr Thr Gly Arg Cys Glu Ala Cys Arg Val Cys Glu Ala Gly Ser
            355                 360                 365

Gly Leu Val Phe Ser Cys Gln Asp Lys Gln Asn Thr Val Cys Glu Glu
            370                 375                 380

Cys Pro Asp Gly Thr Tyr Ser Asp Glu Ala Ala Arg Ala Ala Asp Ala
385                 390                 395                 400

Glu Cys Glu Glu Pro Lys Phe Trp Val Leu Val Val Val Gly Gly Val
                405                 410                 415

Leu Ala Cys Tyr Ser Leu Leu Val Thr Val Ala Phe Ile Ile Phe Trp
                420                 425                 430

Val Arg Ser Lys Arg Ser Arg Leu Leu His Ser Asp Tyr Met Asn Met
                435                 440                 445

Thr Pro Arg Arg Pro Gly Pro Thr Arg Lys His Tyr Gln Pro Tyr Ala
            450                 455                 460

Pro Pro Arg Asp Phe Ala Ala Tyr Arg Ser Arg Val Lys Phe Ser Arg
465                 470                 475                 480

Ser Ala Asp Ala Pro Ala Tyr Gln Gln Gly Gln Asn Gln Leu Tyr Asn
                485                 490                 495

Glu Leu Asn Leu Gly Arg Arg Glu Glu Tyr Asp Val Leu Asp Lys Arg
                500                 505                 510

Arg Gly Arg Asp Pro Glu Met Gly Gly Lys Pro Gln Arg Lys Asn
            515                 520                 525

Pro Gln Glu Gly Leu Tyr Asn Glu Leu Gln Lys Asp Lys Met Ala Glu
            530                 535                 540

Ala Tyr Ser Glu Ile Gly Met Lys Gly Glu Arg Arg Arg Gly Lys Gly
545                 550                 555                 560

His Asp Gly Leu Tyr Gln Gly Leu Ser Thr Ala Thr Lys Asp Thr Tyr
                565                 570                 575

Asp Ala Leu His Met Gln Ala Leu Pro Pro Arg
            580                 585

<210> SEQ ID NO 25
<211> LENGTH: 668
<212> TYPE: PRT
<213> ORGANISM: Artificial Sequence
<220> FEATURE:
<223> OTHER INFORMATION: CD44v6-CAR28z with spacer LNGFR wild-type long
      (NWL)

<400> SEQUENCE: 25

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
```

```
                    85                  90                  95
Leu Glu Pro Glu Asp Phe Ala Val Tyr Tyr Cys Leu Gln Trp Ser Ser
                100                 105                 110

Asn Pro Leu Thr Phe Gly Gly Gly Thr Lys Val Glu Ile Lys Arg Gly
                115                 120                 125

Gly Gly Gly Ser Gly Gly Gly Gly Ser Gly Gly Gly Ser Gly Gly
            130                 135                 140

Gly Gly Ser Glu Val Gln Leu Val Glu Ser Gly Gly Leu Val Lys
145                 150                 155                 160

Pro Gly Gly Ser Leu Arg Leu Ser Cys Ala Ala Ser Gly Phe Thr Phe
                165                 170                 175

Ser Ser Tyr Asp Met Ser Trp Val Arg Gln Ala Pro Gly Lys Gly Leu
                180                 185                 190

Glu Trp Val Ser Thr Ile Ser Ser Gly Gly Ser Tyr Thr Tyr Tyr Leu
                195                 200                 205

Asp Ser Ile Lys Gly Arg Phe Thr Ile Ser Arg Asp Asn Ala Lys Asn
                210                 215                 220

Ser Leu Tyr Leu Gln Met Asn Ser Leu Arg Ala Glu Asp Thr Ala Val
225                 230                 235                 240

Tyr Tyr Cys Ala Arg Gln Gly Leu Asp Tyr Trp Gly Arg Gly Thr Leu
                245                 250                 255

Val Thr Val Ser Ser Gly Asp Pro Lys Glu Ala Cys Pro Thr Gly Leu
                260                 265                 270

Tyr Thr His Ser Gly Glu Cys Cys Lys Ala Cys Asn Leu Gly Glu Gly
                275                 280                 285

Val Ala Gln Pro Cys Gly Ala Asn Gln Thr Val Cys Glu Pro Cys Leu
                290                 295                 300

Asp Ser Val Thr Phe Ser Asp Val Val Ser Ala Thr Glu Pro Cys Lys
305                 310                 315                 320

Pro Cys Thr Glu Cys Val Gly Leu Gln Ser Met Ser Ala Pro Cys Val
                325                 330                 335

Glu Ala Asp Asp Ala Val Cys Arg Cys Ala Tyr Gly Tyr Tyr Gln Asp
                340                 345                 350

Glu Thr Thr Gly Arg Cys Glu Ala Cys Arg Val Cys Glu Ala Gly Ser
                355                 360                 365

Gly Leu Val Phe Ser Cys Gln Asp Lys Gln Asn Thr Val Cys Glu Glu
                370                 375                 380

Cys Pro Asp Gly Thr Tyr Ser Asp Glu Ala Asn His Val Asp Pro Cys
385                 390                 395                 400

Leu Pro Cys Thr Val Cys Glu Asp Thr Glu Arg Gln Leu Arg Glu Cys
                405                 410                 415

Thr Arg Trp Ala Asp Ala Glu Cys Glu Glu Ile Pro Gly Arg Trp Ile
                420                 425                 430

Thr Arg Ser Thr Pro Pro Glu Gly Ser Asp Ser Thr Ala Pro Ser Thr
                435                 440                 445

Gln Glu Pro Glu Ala Pro Pro Glu Gln Asp Leu Ile Ala Ser Thr Val
                450                 455                 460

Ala Gly Val Val Thr Thr Val Met Gly Ser Ser Gln Pro Val Val Thr
465                 470                 475                 480

Arg Gly Thr Thr Asp Asn Pro Lys Phe Trp Val Leu Val Val Val Gly
                485                 490                 495

Gly Val Leu Ala Cys Tyr Ser Leu Leu Val Thr Val Ala Phe Ile Ile
                500                 505                 510
```

```
Phe Trp Val Arg Ser Lys Arg Ser Arg Leu Leu His Ser Asp Tyr Met
            515                 520                 525
Asn Met Thr Pro Arg Arg Pro Gly Pro Thr Arg Lys His Tyr Gln Pro
530                 535                 540
Tyr Ala Pro Pro Arg Asp Phe Ala Ala Tyr Arg Ser Arg Val Lys Phe
545                 550                 555                 560
Ser Arg Ser Ala Asp Ala Pro Ala Tyr Gln Gln Gly Gln Asn Gln Leu
                565                 570                 575
Tyr Asn Glu Leu Asn Leu Gly Arg Arg Glu Glu Tyr Asp Val Leu Asp
            580                 585                 590
Lys Arg Arg Gly Arg Asp Pro Glu Met Gly Gly Lys Pro Arg Arg Lys
        595                 600                 605
Asn Pro Gln Glu Gly Leu Tyr Asn Glu Leu Gln Lys Asp Lys Met Ala
    610                 615                 620
Glu Ala Tyr Ser Glu Ile Gly Met Lys Gly Glu Arg Arg Arg Gly Lys
625                 630                 635                 640
Gly His Asp Gly Leu Tyr Gln Gly Leu Ser Thr Ala Thr Lys Asp Thr
                645                 650                 655
Tyr Asp Ala Leu His Met Gln Ala Leu Pro Pro Arg
            660                 665

<210> SEQ ID NO 26
<211> LENGTH: 608
<212> TYPE: PRT
<213> ORGANISM: Artificial Sequence
<220> FEATURE:
<223> OTHER INFORMATION: CD44v6-CAR28z with spacer LNGFR wild-type short
      (NWS)

<400> SEQUENCE: 26

Met Glu Ala Pro Ala Gln Leu Leu Phe Leu Leu Leu Leu Trp Leu Pro
1               5                   10                  15
Asp Thr Thr Gly Glu Ile Val Leu Thr Gln Ser Pro Ala Thr Leu Ser
            20                  25                  30
Leu Ser Pro Gly Glu Arg Ala Thr Leu Ser Cys Ser Ala Ser Ser Ser
        35                  40                  45
Ile Asn Tyr Ile Tyr Trp Leu Gln Gln Lys Pro Gly Gln Ala Pro Arg
    50                  55                  60
Ile Leu Ile Tyr Leu Thr Ser Asn Leu Ala Ser Gly Val Pro Ala Arg
65                  70                  75                  80
Phe Ser Gly Ser Gly Ser Gly Thr Asp Phe Thr Leu Thr Ile Ser Ser
                85                  90                  95
Leu Glu Pro Glu Asp Phe Ala Val Tyr Tyr Cys Leu Gln Trp Ser Ser
            100                 105                 110
Asn Pro Leu Thr Phe Gly Gly Gly Thr Lys Val Glu Ile Lys Arg Gly
        115                 120                 125
Gly Gly Gly Ser Gly Gly Gly Gly Ser Gly Gly Gly Gly Ser Gly Gly
    130                 135                 140
Gly Gly Ser Glu Val Gln Leu Val Glu Ser Gly Gly Gly Leu Val Lys
145                 150                 155                 160
Pro Gly Gly Ser Leu Arg Leu Ser Cys Ala Ala Ser Gly Phe Thr Phe
                165                 170                 175
Ser Ser Tyr Asp Met Ser Trp Val Arg Gln Ala Pro Gly Lys Gly Leu
            180                 185                 190
Glu Trp Val Ser Thr Ile Ser Ser Gly Gly Ser Tyr Thr Tyr Tyr Leu
```

```
                195                 200                 205
Asp Ser Ile Lys Gly Arg Phe Thr Ile Ser Arg Asp Asn Ala Lys Asn
210                 215                 220

Ser Leu Tyr Leu Gln Met Asn Ser Leu Arg Ala Glu Asp Thr Ala Val
225                 230                 235                 240

Tyr Tyr Cys Ala Arg Gln Gly Leu Asp Tyr Trp Gly Arg Gly Thr Leu
                245                 250                 255

Val Thr Val Ser Ser Gly Asp Pro Lys Glu Ala Cys Pro Thr Gly Leu
                260                 265                 270

Tyr Thr His Ser Gly Glu Cys Cys Lys Ala Cys Asn Leu Gly Glu Gly
                275                 280                 285

Val Ala Gln Pro Cys Gly Ala Asn Gln Thr Val Cys Glu Pro Cys Leu
                290                 295                 300

Asp Ser Val Thr Phe Ser Asp Val Val Ser Ala Thr Glu Pro Cys Lys
305                 310                 315                 320

Pro Cys Thr Glu Cys Val Gly Leu Gln Ser Met Ser Ala Pro Cys Val
                325                 330                 335

Glu Ala Asp Asp Ala Val Cys Arg Cys Ala Tyr Gly Tyr Tyr Gln Asp
                340                 345                 350

Glu Thr Thr Gly Arg Cys Glu Ala Cys Arg Val Cys Glu Ala Gly Ser
                355                 360                 365

Gly Leu Val Phe Ser Cys Gln Asp Lys Gln Asn Thr Val Cys Glu Glu
370                 375                 380

Cys Pro Asp Gly Thr Tyr Ser Asp Glu Ala Asn His Val Asp Pro Cys
385                 390                 395                 400

Leu Pro Cys Thr Val Cys Glu Asp Thr Glu Arg Gln Leu Arg Glu Cys
                405                 410                 415

Thr Arg Trp Ala Asp Ala Glu Cys Glu Glu Pro Lys Phe Trp Val Leu
                420                 425                 430

Val Val Val Gly Gly Val Leu Ala Cys Tyr Ser Leu Leu Val Thr Val
                435                 440                 445

Ala Phe Ile Ile Phe Trp Val Arg Ser Lys Arg Ser Arg Leu Leu His
450                 455                 460

Ser Asp Tyr Met Asn Met Thr Pro Arg Arg Pro Gly Pro Thr Arg Lys
465                 470                 475                 480

His Tyr Gln Pro Tyr Ala Pro Pro Arg Asp Phe Ala Ala Tyr Arg Ser
                485                 490                 495

Arg Val Lys Phe Ser Arg Ser Ala Asp Ala Pro Ala Tyr Gln Gln Gly
                500                 505                 510

Gln Asn Gln Leu Tyr Asn Glu Leu Asn Leu Gly Arg Arg Glu Glu Tyr
                515                 520                 525

Asp Val Leu Asp Lys Arg Arg Gly Arg Asp Pro Glu Met Gly Gly Lys
                530                 535                 540

Pro Arg Arg Lys Asn Pro Gln Glu Gly Leu Tyr Asn Glu Leu Gln Lys
545                 550                 555                 560

Asp Lys Met Ala Glu Ala Tyr Ser Glu Ile Gly Met Lys Gly Glu Arg
                565                 570                 575

Arg Arg Gly Lys Gly His Asp Gly Leu Tyr Gln Gly Leu Ser Thr Ala
                580                 585                 590

Thr Lys Asp Thr Tyr Asp Ala Leu His Met Gln Ala Leu Pro Pro Arg
                595                 600                 605
```

<210> SEQ ID NO 27

<211> LENGTH: 646
<212> TYPE: PRT
<213> ORGANISM: Artificial Sequence
<220> FEATURE:
<223> OTHER INFORMATION: CD44v6-CAR28z with spacer LNGFR mutated long (NWL)

<400> SEQUENCE: 27

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110

Asn Pro Leu Thr Phe Gly Gly Gly Thr Lys Val Glu Ile Lys Arg Gly
        115                 120                 125

Gly Gly Gly Ser Gly Gly Gly Gly Ser Gly Gly Gly Ser Gly Gly
130                 135                 140

Gly Gly Ser Glu Val Gln Leu Val Glu Ser Gly Gly Gly Leu Val Lys
145                 150                 155                 160

Pro Gly Gly Ser Leu Arg Leu Ser Cys Ala Ala Ser Gly Phe Thr Phe
                165                 170                 175

Ser Ser Tyr Asp Met Ser Trp Val Arg Gln Ala Pro Gly Lys Gly Leu
            180                 185                 190

Glu Trp Val Ser Thr Ile Ser Ser Gly Gly Ser Tyr Thr Tyr Tyr Leu
        195                 200                 205

Asp Ser Ile Lys Gly Arg Phe Thr Ile Ser Arg Asp Asn Ala Lys Asn
210                 215                 220

Ser Leu Tyr Leu Gln Met Asn Ser Leu Arg Ala Glu Asp Thr Ala Val
225                 230                 235                 240

Tyr Tyr Cys Ala Arg Gln Gly Leu Asp Tyr Trp Gly Arg Gly Thr Leu
                245                 250                 255

Val Thr Val Ser Ser Gly Asp Pro Lys Glu Ala Cys Pro Thr Gly Leu
            260                 265                 270

Tyr Thr His Ser Gly Glu Cys Cys Lys Ala Cys Asn Leu Gly Glu Gly
        275                 280                 285

Val Ala Gln Pro Cys Gly Ala Asn Gln Thr Val Cys Glu Pro Cys Leu
290                 295                 300

Asp Ser Val Thr Phe Ser Asp Val Val Ser Ala Thr Glu Pro Cys Lys
305                 310                 315                 320

Pro Cys Thr Glu Cys Val Gly Leu Gln Ser Met Ser Ala Pro Cys Val
                325                 330                 335

Glu Ala Asp Asp Ala Val Cys Arg Cys Ala Tyr Gly Tyr Tyr Gln Asp
            340                 345                 350

Glu Thr Thr Gly Arg Cys Glu Ala Cys Arg Val Cys Glu Ala Gly Ser
        355                 360                 365

Gly Leu Val Phe Ser Cys Gln Asp Lys Gln Asn Thr Val Cys Glu Glu
```

```
                    370                 375                 380
Cys Pro Asp Gly Thr Tyr Ser Asp Glu Ala Ala Arg Ala Ala Asp Ala
385                 390                 395                 400

Glu Cys Glu Glu Ile Pro Gly Arg Trp Ile Thr Arg Ser Thr Pro Pro
                405                 410                 415

Glu Gly Ser Asp Ser Thr Ala Pro Ser Thr Gln Glu Pro Glu Ala Pro
            420                 425                 430

Pro Glu Gln Asp Leu Ile Ala Ser Thr Val Ala Gly Val Val Thr Thr
        435                 440                 445

Val Met Gly Ser Ser Gln Pro Val Val Thr Arg Gly Thr Thr Asp Asn
    450                 455                 460

Pro Lys Phe Trp Val Leu Val Val Gly Gly Val Leu Ala Cys Tyr
465                 470                 475                 480

Ser Leu Leu Val Thr Val Ala Phe Ile Ile Phe Trp Val Arg Ser Lys
                485                 490                 495

Arg Ser Arg Leu Leu His Ser Asp Tyr Met Asn Met Thr Pro Arg Arg
            500                 505                 510

Pro Gly Pro Thr Arg Lys His Tyr Gln Pro Tyr Ala Pro Pro Arg Asp
        515                 520                 525

Phe Ala Ala Tyr Arg Ser Arg Val Lys Phe Ser Arg Ser Ala Asp Ala
    530                 535                 540

Pro Ala Tyr Gln Gln Gly Gln Asn Gln Leu Tyr Asn Glu Leu Asn Leu
545                 550                 555                 560

Gly Arg Arg Glu Glu Tyr Asp Val Leu Asp Lys Arg Gly Arg Asp
                565                 570                 575

Pro Glu Met Gly Gly Lys Pro Arg Arg Lys Asn Pro Gln Glu Gly Leu
            580                 585                 590

Tyr Asn Glu Leu Gln Lys Asp Lys Met Ala Glu Ala Tyr Ser Glu Ile
        595                 600                 605

Gly Met Lys Gly Glu Arg Arg Arg Gly Lys Gly His Asp Gly Leu Tyr
    610                 615                 620

Gln Gly Leu Ser Thr Ala Thr Lys Asp Thr Tyr Asp Ala Leu His Met
625                 630                 635                 640

Gln Ala Leu Pro Pro Arg
                645

<210> SEQ ID NO 28
<211> LENGTH: 586
<212> TYPE: PRT
<213> ORGANISM: Artificial Sequence
<220> FEATURE:
<223> OTHER INFORMATION: CD44v6-CAR28z with spacer LNGFR mutated short
      (NWL)

<400> SEQUENCE: 28

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80
```

```
Phe Ser Gly Ser Gly Ser Gly Thr Asp Phe Thr Leu Thr Ile Ser Ser
                85                  90                  95
Leu Glu Pro Glu Asp Phe Ala Val Tyr Tyr Cys Leu Gln Trp Ser Ser
            100                 105                 110
Asn Pro Leu Thr Phe Gly Gly Gly Thr Lys Val Glu Ile Lys Arg Gly
        115                 120                 125
Gly Gly Gly Ser Gly Gly Gly Gly Ser Gly Gly Gly Gly Ser Gly Gly
    130                 135                 140
Gly Gly Ser Glu Val Gln Leu Val Glu Ser Gly Gly Gly Leu Val Lys
145                 150                 155                 160
Pro Gly Gly Ser Leu Arg Leu Ser Cys Ala Ala Ser Gly Phe Thr Phe
                165                 170                 175
Ser Ser Tyr Asp Met Ser Trp Val Arg Gln Ala Pro Gly Lys Gly Leu
            180                 185                 190
Glu Trp Val Ser Thr Ile Ser Ser Gly Gly Ser Tyr Thr Tyr Tyr Leu
        195                 200                 205
Asp Ser Ile Lys Gly Arg Phe Thr Ile Ser Arg Asp Asn Ala Lys Asn
    210                 215                 220
Ser Leu Tyr Leu Gln Met Asn Ser Leu Arg Ala Glu Asp Thr Ala Val
225                 230                 235                 240
Tyr Tyr Cys Ala Arg Gln Gly Leu Asp Tyr Trp Gly Arg Gly Thr Leu
                245                 250                 255
Val Thr Val Ser Ser Gly Asp Pro Lys Glu Ala Cys Pro Thr Gly Leu
            260                 265                 270
Tyr Thr His Ser Gly Glu Cys Cys Lys Ala Cys Asn Leu Gly Glu Gly
        275                 280                 285
Val Ala Gln Pro Cys Gly Ala Asn Gln Thr Val Cys Glu Pro Cys Leu
    290                 295                 300
Asp Ser Val Thr Phe Ser Asp Val Val Ser Ala Thr Glu Pro Cys Lys
305                 310                 315                 320
Pro Cys Thr Glu Cys Val Gly Leu Gln Ser Met Ser Ala Pro Cys Val
                325                 330                 335
Glu Ala Asp Asp Ala Val Cys Arg Cys Ala Tyr Gly Tyr Tyr Gln Asp
            340                 345                 350
Glu Thr Thr Gly Arg Cys Glu Ala Cys Arg Val Cys Glu Ala Gly Ser
        355                 360                 365
Gly Leu Val Phe Ser Cys Gln Asp Lys Gln Asn Thr Val Cys Glu Glu
    370                 375                 380
Cys Pro Asp Gly Thr Tyr Ser Asp Glu Ala Ala Arg Ala Ala Asp Ala
385                 390                 395                 400
Glu Cys Glu Glu Pro Lys Phe Trp Val Leu Val Val Val Gly Gly Val
                405                 410                 415
Leu Ala Cys Tyr Ser Leu Leu Val Thr Val Ala Phe Ile Ile Phe Trp
            420                 425                 430
Val Arg Ser Lys Arg Ser Arg Leu Leu His Ser Asp Tyr Met Asn Met
        435                 440                 445
Thr Pro Arg Arg Pro Gly Pro Thr Arg Lys His Tyr Gln Pro Tyr Ala
    450                 455                 460
Pro Pro Arg Asp Phe Ala Ala Tyr Arg Ser Arg Val Lys Phe Ser Arg
465                 470                 475                 480
Ser Ala Asp Ala Pro Ala Tyr Gln Gln Gly Gln Asn Gln Leu Tyr Asn
                485                 490                 495
Glu Leu Asn Leu Gly Arg Arg Glu Glu Tyr Asp Val Leu Asp Lys Arg
```

```
                500             505              510
Arg Gly Arg Asp Pro Glu Met Gly Gly Lys Pro Arg Lys Asn Pro
            515                 520             525

Gln Glu Gly Leu Tyr Asn Glu Leu Gln Lys Asp Lys Met Ala Glu Ala
            530                 535             540

Tyr Ser Glu Ile Gly Met Lys Gly Glu Arg Arg Arg Gly Lys Gly His
545             550             555                 560

Asp Gly Leu Tyr Gln Gly Leu Ser Thr Ala Thr Lys Asp Thr Tyr Asp
                565             570                 575

Ala Leu His Met Gln Ala Leu Pro Pro Arg
            580                 585

<210> SEQ ID NO 29
<211> LENGTH: 27
<212> TYPE: PRT
<213> ORGANISM: Homo sapiens

<400> SEQUENCE: 29

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 30
<211> LENGTH: 41
<212> TYPE: PRT
<213> ORGANISM: Homo sapiens

<400> SEQUENCE: 30

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 31
<211> LENGTH: 251
<212> TYPE: PRT
<213> ORGANISM: Artificial Sequence
<220> FEATURE:
<223> OTHER INFORMATION: CD44v6-4GS2, CD44v6-specific single chain
      fragment

<400> SEQUENCE: 31

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
            35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110
```

Asn Pro Leu Thr Phe Gly Gly Gly Thr Lys Val Glu Ile Lys Arg Gly
            115                 120                 125

Gly Gly Gly Ser Gly Gly Gly Ser Glu Val Gln Leu Val Glu Ser
        130                 135                 140

Gly Gly Gly Leu Val Lys Pro Gly Gly Ser Leu Arg Leu Ser Cys Ala
145                 150                 155                 160

Ala Ser Gly Phe Thr Phe Ser Ser Tyr Asp Met Ser Trp Val Arg Gln
                165                 170                 175

Ala Pro Gly Lys Gly Leu Glu Trp Val Ser Thr Ile Ser Ser Gly Gly
            180                 185                 190

Ser Tyr Thr Tyr Tyr Leu Asp Ser Ile Lys Gly Arg Phe Thr Ile Ser
        195                 200                 205

Arg Asp Asn Ala Lys Asn Ser Leu Tyr Leu Gln Met Asn Ser Leu Arg
    210                 215                 220

Ala Glu Asp Thr Ala Val Tyr Tyr Cys Ala Arg Gln Gly Leu Asp Tyr
225                 230                 235                 240

Trp Gly Arg Gly Thr Leu Val Thr Val Ser Ser
                245                 250

<210> SEQ ID NO 32
<211> LENGTH: 658
<212> TYPE: PRT
<213> ORGANISM: Artificial Sequence
<220> FEATURE:
<223> OTHER INFORMATION: CD44v6-4GS2-CAR28z with spacer LNGFR wild-type
      long (NWL)

<400> SEQUENCE: 32

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110

Asn Pro Leu Thr Phe Gly Gly Gly Thr Lys Val Glu Ile Lys Arg Gly
            115                 120                 125

Gly Gly Gly Ser Gly Gly Gly Ser Glu Val Gln Leu Val Glu Ser
        130                 135                 140

Gly Gly Gly Leu Val Lys Pro Gly Gly Ser Leu Arg Leu Ser Cys Ala
145                 150                 155                 160

Ala Ser Gly Phe Thr Phe Ser Ser Tyr Asp Met Ser Trp Val Arg Gln
                165                 170                 175

Ala Pro Gly Lys Gly Leu Glu Trp Val Ser Thr Ile Ser Ser Gly Gly
            180                 185                 190

Ser Tyr Thr Tyr Tyr Leu Asp Ser Ile Lys Gly Arg Phe Thr Ile Ser
        195                 200                 205

Arg Asp Asn Ala Lys Asn Ser Leu Tyr Leu Gln Met Asn Ser Leu Arg

```
                  210                 215                 220
Ala Glu Asp Thr Ala Val Tyr Tyr Cys Ala Arg Gln Gly Leu Asp Tyr
225                 230                 235                 240

Trp Gly Arg Gly Thr Leu Val Thr Val Ser Ser Gly Asp Pro Lys Glu
                245                 250                 255

Ala Cys Pro Thr Gly Leu Tyr Thr His Ser Gly Glu Cys Cys Lys Ala
                260                 265                 270

Cys Asn Leu Gly Glu Gly Val Ala Gln Pro Cys Gly Ala Asn Gln Thr
            275                 280                 285

Val Cys Glu Pro Cys Leu Asp Ser Val Thr Phe Ser Asp Val Val Ser
            290                 295                 300

Ala Thr Glu Pro Cys Lys Pro Cys Thr Glu Cys Val Gly Leu Gln Ser
305                 310                 315                 320

Met Ser Ala Pro Cys Val Glu Ala Asp Asp Ala Val Cys Arg Cys Ala
                325                 330                 335

Tyr Gly Tyr Tyr Gln Asp Glu Thr Thr Gly Arg Cys Glu Ala Cys Arg
                340                 345                 350

Val Cys Glu Ala Gly Ser Gly Leu Val Phe Ser Cys Gln Asp Lys Gln
            355                 360                 365

Asn Thr Val Cys Glu Glu Cys Pro Asp Gly Thr Tyr Ser Asp Glu Ala
370                 375                 380

Asn His Val Asp Pro Cys Leu Pro Cys Thr Val Cys Glu Asp Thr Glu
385                 390                 395                 400

Arg Gln Leu Arg Glu Cys Thr Arg Trp Ala Asp Ala Glu Cys Glu Glu
                405                 410                 415

Ile Pro Gly Arg Trp Ile Thr Arg Ser Thr Pro Pro Glu Gly Ser Asp
                420                 425                 430

Ser Thr Ala Pro Ser Thr Gln Glu Pro Glu Ala Pro Pro Glu Gln Asp
            435                 440                 445

Leu Ile Ala Ser Thr Val Ala Gly Val Val Thr Thr Val Met Gly Ser
            450                 455                 460

Ser Gln Pro Val Val Thr Arg Gly Thr Thr Asp Asn Pro Lys Phe Trp
465                 470                 475                 480

Val Leu Val Val Val Gly Gly Val Leu Ala Cys Tyr Ser Leu Leu Val
                485                 490                 495

Thr Val Ala Phe Ile Ile Phe Trp Val Arg Ser Lys Arg Ser Arg Leu
                500                 505                 510

Leu His Ser Asp Tyr Met Asn Met Thr Pro Arg Arg Pro Gly Pro Thr
            515                 520                 525

Arg Lys His Tyr Gln Pro Tyr Ala Pro Pro Arg Asp Phe Ala Ala Tyr
            530                 535                 540

Arg Ser Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
                565                 570                 575

Glu Tyr Asp Val Leu Asp Lys Arg Arg Gly Arg Asp Pro Glu Met Gly
                580                 585                 590

Gly Lys Pro Arg Arg Lys Asn Pro Gln Glu Gly Leu Tyr Asn Glu Leu
            595                 600                 605

Gln Lys Asp Lys Met Ala Glu Ala Tyr Ser Glu Ile Gly Met Lys Gly
            610                 615                 620

Glu Arg Arg Arg Gly Lys Gly His Asp Gly Leu Tyr Gln Gly Leu Ser
625                 630                 635                 640
```

```
Thr Ala Thr Lys Asp Thr Tyr Asp Ala Leu His Met Gln Ala Leu Pro
                645                 650                 655
Pro Arg

<210> SEQ ID NO 33
<211> LENGTH: 598
<212> TYPE: PRT
<213> ORGANISM: Artificial Sequence
<220> FEATURE:
<223> OTHER INFORMATION: CD44v6-4GS2-CAR28z with spacer LNGFR wild-type
      short (NWS)

<400> SEQUENCE: 33

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110

Asn Pro Leu Thr Phe Gly Gly Gly Thr Lys Val Glu Ile Lys Arg Gly
        115                 120                 125

Gly Gly Gly Ser Gly Gly Gly Gly Ser Glu Val Gln Leu Val Glu Ser
    130                 135                 140

Gly Gly Gly Leu Val Lys Pro Gly Gly Ser Leu Arg Leu Ser Cys Ala
145                 150                 155                 160

Ala Ser Gly Phe Thr Phe Ser Ser Tyr Asp Met Ser Trp Val Arg Gln
                165                 170                 175

Ala Pro Gly Lys Gly Leu Glu Trp Val Ser Thr Ile Ser Ser Gly Gly
            180                 185                 190

Ser Tyr Thr Tyr Tyr Leu Asp Ser Ile Lys Gly Arg Phe Thr Ile Ser
        195                 200                 205

Arg Asp Asn Ala Lys Asn Ser Leu Tyr Leu Gln Met Asn Ser Leu Arg
    210                 215                 220

Ala Glu Asp Thr Ala Val Tyr Tyr Cys Ala Arg Gln Gly Leu Asp Tyr
225                 230                 235                 240

Trp Gly Arg Gly Thr Leu Val Thr Val Ser Ser Gly Asp Pro Lys Glu
                245                 250                 255

Ala Cys Pro Thr Gly Leu Tyr Thr His Ser Gly Glu Cys Cys Lys Ala
            260                 265                 270

Cys Asn Leu Gly Glu Gly Val Ala Gln Pro Cys Gly Ala Asn Gln Thr
        275                 280                 285

Val Cys Glu Pro Cys Leu Asp Ser Val Thr Phe Ser Asp Val Val Ser
    290                 295                 300

Ala Thr Glu Pro Cys Lys Pro Cys Thr Glu Cys Val Gly Leu Gln Ser
305                 310                 315                 320

Met Ser Ala Pro Cys Val Glu Ala Asp Asp Ala Val Cys Arg Cys Ala
                325                 330                 335
```

```
Tyr Gly Tyr Tyr Gln Asp Glu Thr Thr Gly Arg Cys Glu Ala Cys Arg
            340                 345                 350

Val Cys Glu Ala Gly Ser Gly Leu Val Phe Ser Cys Gln Asp Lys Gln
            355                 360                 365

Asn Thr Val Cys Glu Cys Pro Asp Gly Thr Tyr Ser Asp Glu Ala
        370                 375                 380

Asn His Val Asp Pro Cys Leu Pro Cys Thr Val Cys Glu Asp Thr Glu
385                 390                 395                 400

Arg Gln Leu Arg Glu Cys Thr Arg Trp Ala Asp Ala Glu Cys Glu Glu
                405                 410                 415

Pro Lys Phe Trp Val Leu Val Val Gly Val Leu Ala Cys Tyr
            420                 425                 430

Ser Leu Leu Val Thr Val Ala Phe Ile Ile Phe Trp Val Arg Ser Lys
            435                 440                 445

Arg Ser Arg Leu Leu His Ser Asp Tyr Met Asn Met Thr Pro Arg Arg
    450                 455                 460

Pro Gly Pro Thr Arg Lys His Tyr Gln Pro Tyr Ala Pro Pro Arg Asp
465                 470                 475                 480

Phe Ala Ala Tyr Arg Ser Arg Val Lys Phe Ser Arg Ser Ala Asp Ala
                485                 490                 495

Pro Ala Tyr Gln Gln Gly Gln Asn Gln Leu Tyr Asn Glu Leu Asn Leu
            500                 505                 510

Gly Arg Arg Glu Glu Tyr Asp Val Leu Asp Lys Arg Arg Gly Arg Asp
            515                 520                 525

Pro Glu Met Gly Gly Lys Pro Arg Arg Lys Asn Pro Gln Glu Gly Leu
            530                 535                 540

Tyr Asn Glu Leu Gln Lys Asp Lys Met Ala Glu Ala Tyr Ser Glu Ile
545                 550                 555                 560

Gly Met Lys Gly Glu Arg Arg Arg Gly Lys Gly His Asp Gly Leu Tyr
                565                 570                 575

Gln Gly Leu Ser Thr Ala Thr Lys Asp Thr Tyr Asp Ala Leu His Met
            580                 585                 590

Gln Ala Leu Pro Pro Arg
            595

<210> SEQ ID NO 34
<211> LENGTH: 636
<212> TYPE: PRT
<213> ORGANISM: Artificial Sequence
<220> FEATURE:
<223> OTHER INFORMATION: CD44v6-4GS2-CAR28z with spacer LNGFR mutated
      long (NML)

<400> SEQUENCE: 34

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
```

```
                        85                  90                  95
Leu Glu Pro Glu Asp Phe Ala Val Tyr Tyr Cys Leu Gln Trp Ser Ser
                100                 105                 110

Asn Pro Leu Thr Phe Gly Gly Gly Thr Lys Val Glu Ile Lys Arg Gly
                115                 120                 125

Gly Gly Gly Ser Gly Gly Gly Ser Glu Val Gln Leu Val Glu Ser
            130                 135                 140

Gly Gly Gly Leu Val Lys Pro Gly Gly Ser Leu Arg Leu Ser Cys Ala
145                 150                 155                 160

Ala Ser Gly Phe Thr Phe Ser Ser Tyr Asp Met Ser Trp Val Arg Gln
                165                 170                 175

Ala Pro Gly Lys Gly Leu Glu Trp Val Ser Thr Ile Ser Ser Gly Gly
                180                 185                 190

Ser Tyr Thr Tyr Tyr Leu Asp Ser Ile Lys Gly Arg Phe Thr Ile Ser
                195                 200                 205

Arg Asp Asn Ala Lys Asn Ser Leu Tyr Leu Gln Met Asn Ser Leu Arg
210                 215                 220

Ala Glu Asp Thr Ala Val Tyr Tyr Cys Ala Arg Gln Gly Leu Asp Tyr
225                 230                 235                 240

Trp Gly Arg Gly Thr Leu Val Thr Val Ser Ser Gly Asp Pro Lys Glu
                245                 250                 255

Ala Cys Pro Thr Gly Leu Tyr Thr His Ser Gly Glu Cys Cys Lys Ala
                260                 265                 270

Cys Asn Leu Gly Glu Gly Val Ala Gln Pro Cys Gly Ala Asn Gln Thr
                275                 280                 285

Val Cys Glu Pro Cys Leu Asp Ser Val Thr Phe Ser Asp Val Val Ser
                290                 295                 300

Ala Thr Glu Pro Cys Lys Pro Cys Thr Glu Cys Val Gly Leu Gln Ser
305                 310                 315                 320

Met Ser Ala Pro Cys Val Glu Ala Asp Asp Ala Val Cys Arg Cys Ala
                325                 330                 335

Tyr Gly Tyr Tyr Gln Asp Glu Thr Thr Gly Arg Cys Glu Ala Cys Arg
                340                 345                 350

Val Cys Glu Ala Gly Ser Gly Leu Val Phe Ser Cys Gln Asp Lys Gln
                355                 360                 365

Asn Thr Val Cys Glu Glu Cys Pro Asp Gly Thr Tyr Ser Asp Glu Ala
                370                 375                 380

Ala Arg Ala Ala Asp Ala Glu Cys Glu Glu Ile Pro Gly Arg Trp Ile
385                 390                 395                 400

Thr Arg Ser Thr Pro Pro Glu Gly Ser Asp Ser Thr Ala Pro Ser Thr
                405                 410                 415

Gln Glu Pro Glu Ala Pro Pro Glu Gln Asp Leu Ile Ala Ser Thr Val
                420                 425                 430

Ala Gly Val Val Thr Thr Val Met Gly Ser Ser Gln Pro Val Val Thr
                435                 440                 445

Arg Gly Thr Thr Asp Asn Pro Lys Phe Trp Val Leu Val Val Val Gly
                450                 455                 460

Gly Val Leu Ala Cys Tyr Ser Leu Leu Val Thr Val Ala Phe Ile Ile
465                 470                 475                 480

Phe Trp Val Arg Ser Lys Arg Ser Arg Leu Leu His Ser Asp Tyr Met
                485                 490                 495

Asn Met Thr Pro Arg Arg Pro Gly Pro Thr Arg Lys His Tyr Gln Pro
                500                 505                 510
```

Tyr Ala Pro Pro Arg Asp Phe Ala Ala Tyr Arg Ser Arg Val Lys Phe
            515                 520                 525

Ser Arg Ser Ala Asp Ala Pro Ala Tyr Gln Gln Gly Gln Asn Gln Leu
        530                 535                 540

Tyr Asn Glu Leu Asn Leu Gly Arg Arg Glu Tyr Asp Val Leu Asp
545                 550                 555                 560

Lys Arg Arg Gly Arg Asp Pro Glu Met Gly Gly Lys Pro Arg Arg Lys
                565                 570                 575

Asn Pro Gln Glu Gly Leu Tyr Asn Glu Leu Gln Lys Asp Lys Met Ala
            580                 585                 590

Glu Ala Tyr Ser Glu Ile Gly Met Lys Gly Glu Arg Arg Arg Gly Lys
            595                 600                 605

Gly His Asp Gly Leu Tyr Gln Gly Leu Ser Thr Ala Thr Lys Asp Thr
        610                 615                 620

Tyr Asp Ala Leu His Met Gln Ala Leu Pro Pro Arg
625                 630                 635

<210> SEQ ID NO 35
<211> LENGTH: 576
<212> TYPE: PRT
<213> ORGANISM: Artificial Sequence
<220> FEATURE:
<223> OTHER INFORMATION: CD44v6-4GS2-CAR28z with spacer LNGFR mutated
      short (NMS)

<400> SEQUENCE: 35

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110

Asn Pro Leu Thr Phe Gly Gly Gly Thr Lys Val Glu Ile Lys Arg Gly
        115                 120                 125

Gly Gly Gly Ser Gly Gly Gly Gly Ser Glu Val Gln Leu Val Glu Ser
    130                 135                 140

Gly Gly Gly Leu Val Lys Pro Gly Gly Ser Leu Arg Leu Ser Cys Ala
145                 150                 155                 160

Ala Ser Gly Phe Thr Phe Ser Ser Tyr Asp Met Ser Trp Val Arg Gln
                165                 170                 175

Ala Pro Gly Lys Gly Leu Glu Trp Val Ser Thr Ile Ser Ser Gly Gly
            180                 185                 190

Ser Tyr Thr Tyr Tyr Leu Asp Ser Ile Lys Gly Arg Phe Thr Ile Ser
        195                 200                 205

Arg Asp Asn Ala Lys Asn Ser Leu Tyr Leu Gln Met Asn Ser Leu Arg
    210                 215                 220

Ala Glu Asp Thr Ala Val Tyr Tyr Cys Ala Arg Gln Gly Leu Asp Tyr

```
            225                 230                 235                 240
Trp Gly Arg Gly Thr Leu Val Thr Val Ser Ser Gly Asp Pro Lys Glu
                245                 250                 255

Ala Cys Pro Thr Gly Leu Tyr Thr His Ser Gly Glu Cys Cys Lys Ala
                260                 265                 270

Cys Asn Leu Gly Glu Gly Val Ala Gln Pro Cys Gly Ala Asn Gln Thr
                275                 280                 285

Val Cys Glu Pro Cys Leu Asp Ser Val Thr Phe Ser Asp Val Val Ser
                290                 295                 300

Ala Thr Glu Pro Cys Lys Pro Cys Thr Glu Cys Val Gly Leu Gln Ser
305                 310                 315                 320

Met Ser Ala Pro Cys Val Glu Ala Asp Asp Ala Val Cys Arg Cys Ala
                325                 330                 335

Tyr Gly Tyr Tyr Gln Asp Glu Thr Thr Gly Arg Cys Glu Ala Cys Arg
                340                 345                 350

Val Cys Glu Ala Gly Ser Gly Leu Val Phe Ser Cys Gln Asp Lys Gln
                355                 360                 365

Asn Thr Val Cys Glu Glu Cys Pro Asp Gly Thr Tyr Ser Asp Glu Ala
                370                 375                 380

Ala Arg Ala Ala Asp Ala Glu Cys Glu Pro Lys Phe Trp Val Leu
385                 390                 395                 400

Val Val Val Gly Gly Val Leu Ala Cys Tyr Ser Leu Leu Val Thr Val
                405                 410                 415

Ala Phe Ile Ile Phe Trp Val Arg Ser Lys Arg Ser Arg Leu Leu His
                420                 425                 430

Ser Asp Tyr Met Asn Met Thr Pro Arg Arg Pro Gly Pro Thr Arg Lys
                435                 440                 445

His Tyr Gln Pro Tyr Ala Pro Pro Arg Asp Phe Ala Ala Tyr Arg Ser
                450                 455                 460

Arg Val Lys Phe Ser Arg Ser Ala Asp Ala Pro Ala Tyr Gln Gln Gly
465                 470                 475                 480

Gln Asn Gln Leu Tyr Asn Glu Leu Asn Leu Gly Arg Arg Glu Glu Tyr
                485                 490                 495

Asp Val Leu Asp Lys Arg Arg Gly Arg Asp Pro Glu Met Gly Gly Lys
                500                 505                 510

Pro Arg Arg Lys Asn Pro Gln Glu Gly Leu Tyr Asn Glu Leu Gln Lys
                515                 520                 525

Asp Lys Met Ala Glu Ala Tyr Ser Glu Ile Gly Met Lys Gly Glu Arg
                530                 535                 540

Arg Arg Gly Lys Gly His Asp Gly Leu Tyr Gln Gly Leu Ser Thr Ala
545                 550                 555                 560

Thr Lys Asp Thr Tyr Asp Ala Leu His Met Gln Ala Leu Pro Pro Arg
                565                 570                 575

<210> SEQ ID NO 36
<211> LENGTH: 10
<212> TYPE: PRT
<213> ORGANISM: Artificial Sequence
<220> FEATURE:
<223> OTHER INFORMATION: Peptide linker

<400> SEQUENCE: 36

Gly Gly Gly Gly Ser Gly Gly Gly Gly Ser
1               5                   10
```

```
<210> SEQ ID NO 37
<211> LENGTH: 8331
<212> TYPE: DNA
<213> ORGANISM: Artificial Sequence
<220> FEATURE:
<223> OTHER INFORMATION: CD44v6-4GS2-CAR.28Z NGFR WILD TYPE LONG (V6
      NWL)

<400> SEQUENCE: 37
aagctttgct cttaggagtt tcctaataca tcccaaactc aaatatataa agcatttgac      60
ttgttctatg ccctaggggg cggggggaag ctaagccagc ttttttttaac atttaaaatg    120 ttaattccat tttaaatgca cagatgtttt tatttcataa gggtttcaat gtgcatgaat    180
gctgcaatat tcctgttacc aaagctagta taaataaaaa tagataaacg tggaaattac    240
ttagagtttc tgtcattaac gtttccttcc tcagttgaca acataaatgc gctgctgagc    300
aagccagttt gcatctgtca ggatcaattt cccattatgc cagtcatatt aattactagt    360
caattagttg attttatttt ttgacatata catgtgaatg aaagacccca cctgtaggtt    420
tggcaagcta gcttaagtaa cgccattttg caaggcatgg aaaaatacat aactgagaat    480
agaaaagttc agatcaaggt caggaacaga tggaacagct gaatatgggc caaacaggat    540
atctgtggta agcagttcct gccccggctc agggccaaga acagatggaa cagctgaata    600
tgggccaaac aggatatctg tggtaagcag ttcctgcccc ggctcagggc caagaacaga    660
tggtccccag atgcggtcca gccctcagca gtttctagag aaccatcaga tgtttccagg    720
gtgccccaag gacctgaaat gaccctgtgc ttatttgaa ctaaccaatc agttcgcttc    780
tcgcttctgt tcgcgcgctt atgctccccg agctcaataa aagagcccac aacccctcac    840
tcggggcgcc agtcctccga ttgactgagt cgcccgggta ccgtgtatc caataaaccc    900 tcttgcagtt gcatccgact tgtggtctcg ctgttccttg ggagggtctc ctctgagtga    960
ttgactaccc gtcagcgggg gtctttcatt tgggggctcg tccgggatcg ggagacccct   1020
gcccagggac caccgaccca ccaccggag gtaagctggc cagcaactta tctgtgtctg   1080
tccgattgtc tagtgtctat gactgatttt atgcgcctgc gtcggtacta gttagctaac   1140
tagctctgta tctggcggac ccgtggtgga actgacgagt tcggaacacc cggccgcaac   1200
cctgggagac gtcccaggga cttcggggc cgttttttgtg gcccgacctg agtcctaaaa   1260
tcccgatcgt ttaggactct tggtgcacc cccttagag gagggatatg tggttctggt   1320
aggagacgag aacctaaaac agttcccgcc tccgtctgaa ttttttgcttt cggtttggga   1380 ccgaagccgc gccgcgcgtc ttgtctgctg cagcatcgtt ctgtgttgtc tctgtctgac   1440
tgtgtttctg tatttgtctg aaaatatggg cccgggctag cctgttacca ctcccttaag   1500
tttgacctta ggtcactgga aagatgtcga gcggatcgct cacaaccagt cggtagatgt   1560
caagaagaga cgttgggtta ccttctgctc tgcagaatgg ccaaccttta acgtcggatg   1620
gccgcgagac ggcacccttta accgagacct catcacccag gttaagatca aggtcttttc   1680
acctggcccg catggacacc cagaccaggt ggggtacatc gtgacctggg aagcttggc   1740 ttttgacccc cctccctggg tcaagccctt tgtacaccct aagcctccgc ctcctcttcc   1800
tccatccgcc ccgtctctcc cccttgaacc tcctcgttcg accccgcctc gatcctccct   1860
ttatccagcc ctcactcctt ctctaggcgc ccccatatgg ccatatgaga tcttatatgg   1920 ggcaccccg ccccttgtaa acttccctga ccctgacatg acaagagtta ctaacagccc   1980
ctctctccaa gctcacttac aggctctcta cttagtccag cacgaagtct ggagacctct   2040
ggcggcagcc taccaagaac aactggaccg accggtggta cctcacccctt accgagtcgg   2100
```

```
cgacacagtg tgggtccgcc gacaccagac taagaaccta gaacctcgct ggaaaggacc    2160
ttacacagtc ctgctgacca ccccaccgc cctcaaagta gacggcatcg cagcttggat    2220
acacgccgcc cacgtgaagg ctgccgaccc cggggtgga ccatcctcta gactgccatg     2280
gaagcccctg cccagctgct gttcctgctg ctgctgtggc tgcccgacac caccggcgag    2340
atcgtgctga cacagagccc cgccaccctg tctctgagcc ctggcgagag agccaccctg    2400
agctgtagcg ccagcagcag catcaactac atctactggc tgcagcagaa gcccggccag    2460
gcccccagaa tcctgatcta cctgaccagc aacctggcca gcggcgtgcc cgccagattt    2520
tctggcagcg gcagcggcac cgacttcacc ctgaccatca gcagcctgga acccgaggac    2580
ttcgccgtgt actactgcct gcagtggtcc agcaaccccc tgaccttcgg cggaggcacc    2640
aaggtggaaa tcaagcgggg tggtggtggt tctggtggtg gtggttctga ggtgcagctg    2700
gtggaaagcg gcggaggcct ggtcaagcct ggcggcagcc tgagactgag ctgtgccgcc    2760
agcggcttca ccttcagcag ctacgacatg agctgggtcc gacaggctcc aggcaaggga    2820
ctggaatggg tgtccaccat cagcagcggc ggcagctaca cctactacct ggacagcatc    2880
aagggccggt tcaccatcag ccgggacaac gccaagaaca ccctgtacct gcagatgaac    2940
agcctgcggg ccgaggacac cgccgtctac tactgtgccc ggcagggcct cgactactgg    3000
ggcagaggca ccctggtcac cgtgtccagc ggggatccca agaggcctg ccccaccggc    3060 ctgtacaccc acagcggaga gtgctgcaag gcctgcaacc tgggagaggg cgtggcccag    3120
ccttgcggcg ccaatcagac cgtgtgcgag ccctgcctgg acagcgtgac cttcagcgac    3180
gtggtgtccg ccaccgagcc ctgcaagcct tgcaccgagt gtgtgggcct gcagagcatg    3240
agcgccccct gcgtggaagc cgacgacgcc gtgtgtagat cgcctacgg ctactaccag    3300 gacgagacaa ccggcagatg cgaggcctgt agagtgtgcg aggccggcag cggcctggtg    3360
ttcagttgtc aagacaagca gaataccgtg tgtgaagagt gccccgacgg cacctacagc    3420
gacgaggcca accacgtgga ccctgcctg ccctgcactg tgtgcgagga caccgagcgg    3480
cagctgcgcg agtgcacaag atgggccgac gccgagtgcg aagagatccc cggcagatgg    3540
atcaccagaa gcaccccccc tgagggcagc gacagcaccg cccctagcac ccaggaacct    3600
gaggcccctc ccgagcagga cctgatcgcc tctacagtgg ccggcgtggt gacaaccgtg    3660
atgggcagct ctcagcccgt ggtgacacgg ggcaccaccg acaatcccaa attttgggtg    3720
ctggtggtgg ttggtggagt cctggcttgc tatagcttgc tagtaacagt ggcctttatt    3780
attttctggg tgaggagtaa gaggagcagg ctcctgcaca gtgactacat gaacatgact    3840
ccccgccgcc ccgggcccac ccgcaagcat taccagccct atgccccacc acgcgacttc    3900
gcagcctatc gctccagagt gaagttcagc aggagcgcag acgcccccgc gtaccagcag    3960
ggccagaacc agctctataa cgagctcaat ctaggacgaa gagaggagta cgatgttttg    4020
gacaagagac gtggccggga ccctgagatg ggggaaagc cgagaaggaa gaaccctcag    4080
gaaggcctgt acaatgaact gcagaaagat aagatggcgg aggcctacag tgagattggg    4140
atgaaaggcg agcgccggag gggcaagggg cacgatggcc tttaccaggg tctcagtaca    4200
gccaccaagg acacctacga cgcccttcac atgcaggccc tgcctcctcg ctaagcatgc    4260
aacctcgatc cggattagtc caatttgtta agacaggat atcagtggtc caggctctag    4320
ttttgactca acaatatcac cagctgaagc ctatagagta cgagccatag ataaaataaa    4380
agattttatt tagtctccag aaaaaggggg gaatgaaaga ccccacctgt aggtttggca    4440
```

```
agctagctta agtaacgcca ttttgcaagg catggaaaaa tacataactg agaatagaga   4500
agttcagatc aaggtcagga acagatggaa cagctgaata tgggccaaac aggatatctg   4560
tggtaagcag ttcctgcccc ggctcagggc caagaacaga tggaacagct gaatatgggc   4620
caaacaggat atctgtggta agcagttcct gccccggctc agggccaaga acagatggtc   4680
cccagatgcg gtccagccct cagcagtttc tagagaacca tcagatgttt ccagggtgcc   4740
ccaaggacct gaaatgaccc tgtgccttat ttgaactaac caatcagttc gcttctcgct   4800
tctgttcgcg cgcttctgct ccccgagctc aataaaagag cccacaaccc ctcactcggg   4860
gcgccagtcc tccgattgac tgagtcgccc gggtacccgt gtatccaata aaccctcttg   4920
cagttgcatc cgacttgtgg tctcgctgtt ccttgggagg gtctcctctg agtgattgac   4980
tacccgtcag cggggggtctt tcacacatgc agcatgtatc aaaattaatt tggttttttt   5040
tcttaagtat ttacattaaa tggccatagt acttaaagtt acattggctt ccttgaaata   5100
aacatggagt attcagaatg tgtcataaat atttctaatt ttaagatagt atctccattg   5160
gctttctact ttttctttta tttttttttg tcctctgtct tccatttgtt gttgttgttg   5220
tttgtttgtt tgtttgttgg ttggttggtt aattttttt taaagatcct acactatagt   5280
tcaagctaga ctattagcta ctctgtaacc cagggtgacc ttgaagtcat gggtagcctg   5340
ctgttttagc cttcccacat ctaagattac aggtatgagc tatcattttt ggtatattga   5400
ttgattgatt gattgatgtg tgtgtgtgtg attgtgtttg tgtgtgtgac tgtgaaaatg   5460
tgtgtatggg tgtgtgtgaa tgtgtgtatg tatgtgtgtg tgtgagtgtg tgtgtgtgtg   5520
tgtgcatgtg tgtgtgtgtg actgtgtcta tgtgtatgac tgtgtgtgtg tgtgtgtgtg   5580
tgtgtgtgtg tgtgtgtgtg tgtgtgttgt gaaaaaatat tctatggtag tgagagccaa   5640
cgctccggct caggtgtcag gttggttttt gagacagagt ctttcactta gcttggaatt   5700
cactggccgt cgttttacaa cgtcgtgact gggaaaaccc tggcgttacc caacttaatc   5760
gccttgcagc acatcccccct ttcgccagct ggcgtaatag cgaagaggcc cgcaccgatc   5820
gcccttccca acagttgcgc agcctgaatg gcgaatggcg cctgatgcgg tattttctcc   5880
ttacgcatct gtgcggtatt tcacaccgca tatggtgcac tctcagtaca atctgctctg   5940
atgccgcata gttaagccag ccccgacacc cgccaacacc cgctgacgcg ccctgacggg   6000
cttgtctgct cccggcatcc gcttacagac aagctgtgac cgtctccggg agctgcatgt   6060
gtcagaggtt ttcaccgtca tcaccgaaac gcgcgatgac gaaagggcct cgtgatacgc   6120
ctatttttat aggttaatgt catgataata atggtttctt agacgtcagg tggcacttttt   6180 cggggaaatg tgcgcggaac ccctatttgt ttatttttct aaatacattc aaatatgtat   6240
ccgctcatga caataaaccc tgataaatg cttcaataat attgaaaaag gaagagtatg   6300
agtattcaac atttccgtgt cgcccttatt cccttttttg cggcattttg ccttcctgtt   6360
tttgctcacc cagaaacgct ggtgaaagta aaagatgctg aagatcagtt gggtgcacga   6420
gtgggttaca tcgaactgga tctcaacagc ggtaagatcc ttgagagttt tcgccccgaa   6480
gaacgttttc caatgatgag cacttttaaa gttctgctat gtggcgcggt attatcccgt   6540
attgacgccg gcaagagcaa actcggtcgc cgcatacact attctcagaa tgacttggtt   6600
gagtactcac cagtcacaga aaagcatctt acggatggca tgacagtaag agaattatgc   6660
agtgctgcca taaccatgag tgataacact gcggccaact tacttctgac aacgatcgga   6720
ggaccgaagg agctaaccgc ttttttgcac aacatggggg atcatgtaac tcgccttgat   6780
cgttgggaac cggagctgaa tgaagccata ccaaacgacg agcgtgacac cacgatgcct   6840
```

```
gtagcaatgg caacaacgtt gcgcaaacta ttaactggcg aactactac tctagcttcc    6900 cggcaacaat taatagactg gatggaggcg gataaagttg caggaccact tctgcgctcg    6960
gcccttccgg ctggctggtt tattgctgat aaatctggag ccggtgagcg tgggtctcgc    7020
ggtatcattg cagcactggg gccagatggt aagcccctcc cgtatcgtagt tatctacacg    7080 acggggagtc aggcaactat ggatgaacga aatagacaga tcgctgagat aggtgcctca    7140
ctgattaagc attggtaact gtcagaccaa gtttactcat atatacttta gattgattta    7200
aaacttcatt tttaatttaa aaggatctag gtgaagatcc ttttttgataa tctcatgacc    7260 aaaatccctt aacgtgagtt ttcgttccac tgagcgtcag accccgtaga aaagatcaaa    7320
ggatcttctt gagatccttt ttttctgcgc gtaatctgct gcttgcaaac aaaaaaacca    7380
ccgctaccag cggtggtttg tttgccggat caagagctac caactctttt tccgaaggta    7440
actggcttca gcagagcgca gataccaaat actgtccttc tagtgtagcc gtagttaggc    7500
caccacttca agaactctgt agcaccgcct acatacctcg ctctgctaat cctgttacca    7560
gtggctgctg ccagtggcga taagtcgtgt cttaccgggt tggactcaag acgatagtta    7620
ccggataagg cgcagcggtc gggctgaacg gggggttcgt gcacacagcc cagcttggag    7680
cgaacgacct acaccgaact gagatacctta cagcgtgagc attgagaaag cgccacgctt    7740
cccgaaggga gaaaggcgga caggtatccg gtaagcggca gggtcggaac aggagagcgc    7800
acgagggagc ttccaggggg aaacgcctgg tatctttata gtcctgtcgg gtttcgccac    7860
ctctgacttg agcgtcgatt tttgtgatgc tcgtcagggg ggcggagcct atggaaaaac    7920
gccagcaacg cggcctttt acggttcctg ccttttgct ggcttttgc tcacatgttc    7980 tttcctgcgt tatcccctga ttctgtggat aaccgtatta ccgcctttga gtgagctgat    8040
accgctcgcc gcagccgaac gaccgagcgc agcgagtcag tgagcgagga agcggaagag    8100
cgcccaatac gcaaaccgcc tctccccgcg cgttggccga ttcattaatg cagctggcac    8160
gacaggtttc ccgactggaa agcgggcagt gagcgcaacg caattaatgt gagttagctc    8220
actcattagg caccccaggc tttacacttt atgcttccgg ctcgtatgtt gtgtggaatt    8280
gtgagcggat aacaatttca cacaggaaac agctatgacc atgattacgc c    8331

<210> SEQ ID NO 38
<211> LENGTH: 8151
<212> TYPE: DNA
<213> ORGANISM: Artificial Sequence
<220> FEATURE:
<223> OTHER INFORMATION: CD44V6-4GS2-CAR.28Z NGFR WILD TYPE SHORT (V6
     NWS)

<400> SEQUENCE: 38
aagctttgct cttaggagtt tcctaataca tcccaaactc aaatatataa agcatttgac       60
ttgttctatg ccctaggggg cgggggggaag ctaagccagc tttttttaac atttaaaatg      120
ttaattccat tttaaatgca cagatgtttt tatttcataa gggtttcaat gtgcatgaat      180
gctgcaatat tcctgttacc aaagctagta taaataaaaa tagataaacg tggaaattac      240
ttagagtttc tgtcattaac gtttccttcc tcagttgaca acataaatgc gctgctgagc      300
aagccagttt gcatctgtca ggatcaattt cccattatgc cagtcatatt aattactagt      360
caattagttg attttatttt ttgacatata catgtgaatg aaagacccca cctgtaggtt      420
tggcaagcta gcttaagtaa cgccattttg caaggcatgg aaaatacat aactgagaat      480 agaaaagttc agatcaaggt caggaacaga tggaacagct gaatatgggc caaacaggat      540
```

```
atctgtggta agcagttcct gccccggctc agggccaaga acagatggaa cagctgaata      600
tgggccaaac aggatatctg tggtaagcag ttcctgcccc ggctcagggc caagaacaga      660
tggtccccag atgcggtcca gccctcagca gtttctagag aaccatcaga tgtttccagg      720
gtgccccaag gacctgaaat gaccctgtgc cttatttgaa ctaaccaatc agttcgcttc      780
tcgcttctgt tcgcgcgctt atgctccccg agctcaataa aagagcccac aaccccctcac     840 tcggggcgcc agtcctccga ttgactgagt cgcccgggta cccgtgtatc caataaaccc      900
tcttgcagtt gcatccgact tgtggtctcg ctgttccttg ggagggtctc ctctgagtga      960
ttgactaccc gtcagcgggg gtctttcatt tgggggctcg tccgggatcg ggagacccct     1020
gcccagggac caccgaccca ccaccgggag gtaagctggc cagcaactta tctgtgtctg     1080
tccgattgtc tagtgtctat gactgatttt atgcgcctgc gtcggtacta gttagctaac     1140
tagctctgta tctggcggac ccgtggtgga actgacgagt tcggaacacc cggccgcaac     1200
cctgggagag tcccaggga cttcggggc cgttttttgtg gcccgacctg agtcctaaaa      1260
tcccgatcgt ttaggactct ttggtgcacc cccttagag gagggatatg tggttctggt      1320
aggagacgag aacctaaaac agttcccgcc tccgtctgaa ttttttgcttt cggtttggga     1380 ccgaagccgc gccgcgcgtc ttgtctgctg cagcatcgtt ctgtgttgtc tctgtctgac     1440
tgtgtttctg tatttgtctg aaaatatggg cccgggctag cctgttacca ctcccttaag     1500 tttgaccta ggtcactgga aagatgtcga gcggatcgct cacaaccagt cggtagatgt      1560
caagaagaga cgttgggtta ccttctgctc tgcagaatgg ccaaccttta acgtcggatg     1620
gccgcgagac ggcacctta accgagacct catcacccag gttaagatca aggtcttttc      1680
acctggcccg catggacacc cagaccaggt ggggtacatc gtgacctggg aagccttggc     1740
ttttgacccc cctccctggg tcaagccctt tgtacaccct aagcctccgc ctcctcttcc     1800
tccatccgcc ccgtctctcc cccttgaacc tcctcgttcg accccgcctc gatcctccct     1860
ttatccagcc ctcactcctt tctaggcgc ccccatatgg ccatatgaga tcttatatgg     1920 ggcaccccg cccccttgtaa acttcccctga ccctgacatg acaagagtta ctaacagccc    1980
ctctctccaa gctcacttac aggctctcta cttagtccag cacgaagtct ggagacctct    2040
ggcggcagcc taccaagaac aactggaccg accggtggta cctcacccctt accgagtcgg    2100 cgacacagtg tgggtccgcc gacaccagac taagaaccta gaacctcgct ggaaaggacc    2160
ttacacagtc ctgctgacca cccccaccgc cctcaaagta gacggcatcg cagcttggat     2220
acacgccgcc cacgtgaagg ctgccgaccc cggggggtgga ccatcctcta gactgccatg    2280
gaagcccctg cccagctgct gttcctgctg ctgctgtggc tgcccgacac caccggcgag     2340
atcgtgctga cacagagccc cgccaccctg tctctgagcc ctggcgagag agccaccctg    2400
agctgtagcg ccagcagcag catcaactac atctactggc tgcagcagaa gcccggccag    2460 gccccagaa tcctgatcta cctgaccagc aacctggcca gcggcgtgcc cgccagattt     2520
tctggcagcg gcagcggcac cgacttcacc ctgaccatca gcagcctgga acccgaggac    2580
ttcgccgtgt actactgcct gcagtggtcc agcaaccccc tgaccttcgg cggaggcacc    2640
aaggtggaaa tcaagcgggg tggtggtggt tctggtggtg gtggttctga ggtgcagctg    2700
gtggaaagcg gcggaggcct ggtcaagcct ggcggcagcc tgagactgag ctgtgccgcc    2760
agcggcttca ccttcagcag ctacgacatg agctgggtcc gacaggctcc aggcaaggga    2820
ctggaatggg tgtccaccat cagcagcggc ggcagctaca cctactacct ggacagcatc    2880
```

```
aagggccggt tcaccatcag ccgggacaac gccaagaaca gcctgtacct gcagatgaac    2940
agcctgcggg ccgaggacac cgccgtctac tactgtgccc ggcagggcct cgactactgg    3000
ggcagaggca ccctggtcac cgtgtccagc ggggatccca agaggcctg ccccaccggc     3060
ctgtacaccc acagcggaga gtgctgcaag gcctgcaacc tgggagaggg cgtggcccag    3120
ccttgcggcg ccaatcagac cgtgtgcgag ccctgcctgg acagcgtgac cttcagcgac    3180
gtggtgtccg ccaccgagcc ctgcaagcct tgcaccgagt gtgtgggcct gcagagcatg    3240
agcgccccct gcgtggaagc cgacgacgcc gtgtgtagat gcgcctacgg ctactaccag    3300
gacgagacaa ccggcagatg cgaggcctgt agagtgtgcg aggccggcag cggcctggtg    3360
ttcagttgtc aggacaagca gaacaccgtg tgtgaagagt gccccgacgg cacctacagc    3420
gacgaggcca accacgtgga ccctgcctg ccctgcactg tgtgcgagga caccgagcgg    3480
cagctgcgcg agtgcacaag atgggccgac gccgagtgcg aggaacccaa attttgggtg    3540
ctggtggtgg ttggtggagt cctgccttgc tatagcttgc tagtaacagt ggcctttatt    3600
attttctggg tgaggagtaa gaggagcagg ctcctgcaca gtgactacat gaacatgact    3660
ccccgccgcc ccgggcccac cgcaagcat taccagccct atgccccacc acgcgacttc    3720
gcagccatc gctccagagt gaagttcagc aggagcgcag acgcccccgc gtaccagcag    3780
ggccagaacc agctctataa cgagctcaat ctaggacgaa gagaggagta cgatgttttg    3840
gacaagagac gtggccggga ccctgagatg gggggaaagc cgagaaggaa gaaccctcag    3900
gaaggcctgt acaatgaact gcagaaagat aagatggcgg aggcctacag tgagattggg    3960
atgaaaggcg agcgccggag gggcaagggg cacgatggcc tttaccaggg tctcagtaca    4020
gccaccaagg acacctacga cgcccttcac atgcaggccc tgcctcctcg ctaagcatgc    4080
aacctcgatc cggattagtc caatttgtta agacaggat atcagtggtc caggctctag    4140
ttttgactca acaatatcac cagctgaagc ctatagagta cgagccatag ataaaataaa    4200
agattttatt tagtctccag aaaaaggggg gaatgaaaga ccccacctgt aggtttggca    4260
agctagctta agtaacgcca ttttgcaagg catggaaaaa tacataactg agaatagaga    4320
agttcagatc aaggtcagga acagatggaa cagctgaata tgggccaaac aggatatctg    4380
tggtaagcag ttcctgcccc ggctcagggc caagaacaga tggaacagct gaatatgggc    4440
caaacaggat atctgtggta agcagttcct gccccggctc agggccaaga acagatggtc    4500
cccagatgcg gtccagccct cagcagtttc tagagaacca tcagatgttt ccagggtgcc    4560
ccaaggacct gaaatgaccc tgtgccttat ttgaactaac caatcagttc gcttctcgct    4620
tctgttcgcg cgcttctgct ccccgagctc aataaaagag cccacaaccc ctcactcggg    4680
gcgccagtcc tccgattgac tgagtcgccc gggtacccgt gtatccaata aaccctcttg    4740
cagttgcatc cgacttgtgg tctcgctgtt ccttgggagg gtctcctctg agtgattgac    4800
tacccgtcag cggggggtctt tcacacatgc agcatgtatc aaaattaatt ggttttttt    4860
tcttaagtat ttacattaaa tggccatagt acttaaagtt acattggctt ccttgaaata    4920
aacatggagt attcagaatg tgtcataaat atttctaatt ttaagatagt atctccattg    4980
gctttctact ttttcttta tttttttttg tcctctgtct tccatttgtt gttgttgttg    5040
tttgtttgtt tgtttgttgg ttggttggtt aattttttt taaagatcct acactatagt    5100
tcaagctaga ctattagcta ctctgtaacc cagggtgacc ttgaagtcat gggtagcctg    5160
ctgttttagc cttcccacat ctaagattac aggtatgagc tatcattttt ggtatattga    5220
ttgattgatt gattgatgtg tgtgtgtgtg attgtgtttg tgtgtgtgac tgtgaaaatg    5280
```

```
tgtgtatggg tgtgtgtgaa tgtgtgtatg tatgtgtgtg tgtgagtgtg tgtgtgtgtg    5340
tgtgcatgtg tgtgtgtgtg actgtgtcta tgtgtatgac tgtgtgtgtg tgtgtgtgtg    5400
tgtgtgtgtg tgtgtgtgtg tgtgtgttgt gaaaaaatat tctatggtag tgagagccaa    5460
cgctccggct caggtgtcag gttggttttt gagacagagt ctttcactta gcttggaatt    5520
cactggccgt cgttttacaa cgtcgtgact gggaaaaccc tggcgttacc caacttaatc    5580
gccttgcagc acatcccct ttcgccagct ggcgtaatag cgaagaggcc cgcaccgatc     5640
gcccttccca acagttgcgc agcctgaatg gcgaatggcg cctgatgcgg tattttctcc    5700
ttacgcatct gtgcggtatt tcacaccgca tatggtgcac tctcagtaca atctgctctg    5760
atgccgcata gttaagccag ccccgacacc cgccaacacc cgctgacgcg ccctgacggg    5820
cttgtctgct cccggcatcc gcttacagac aagctgtgac cgtctccggg agctgcatgt    5880
gtcagaggtt ttcaccgtca tcaccgaaac gcgcgatgac gaaagggcct cgtgatacgc    5940
ctatttttat aggttaatgt catgataata atggtttctt agacgtcagg tggcactttt    6000
cggggaaatg tgcgcggaac ccctatttgt ttatttttct aaatacattc aaatatgtat    6060
ccgctcatga caataaacc ctgataaatg cttcaataat attgaaaaag gaagagtatg     6120
agtattcaac atttccgtgt cgcccttatt cccttttttg cggcattttg ccttcctgtt    6180
tttgctcacc cagaaacgct ggtgaaagta aaagatgctg aagatcagtt gggtgcacga    6240
gtgggttaca tcgaactgga tctcaacagc ggtaagatcc ttgagagttt tcgccccgaa    6300
gaacgttttc caatgatgag cacttttaaa gttctgctat gtggcgcggt attatcccgt    6360
attgacgccg ggcaagagca actcggtcgc cgcatacact attctcagaa tgacttggtt    6420
gagtactcac cagtcacaga aaagcatctt acggatggca tgacagtaag agaattatgc    6480
agtgctgcca taaccatgag tgataacact gcggccaact tacttctgac aacgatcgga    6540
ggaccgaagg agctaaccgc ttttttgcac aacatggggg atcatgtaac tcgccttgat    6600
cgttgggaac cggagctgaa tgaagccata ccaaacgacg agcgtgacac cacgatgcct    6660
gtagcaatgg caacaacgtt gcgcaaacta ttaactggcg aactacttac tctagcttcc    6720
cggcaacaat taatagactg gatggaggcg gataaagttg caggaccact tctgcgctcg    6780
gcccttccgg ctggctggtt tattgctgat aaatctggag ccggtgagcg tgggtctcgc    6840
ggtatcattg cagcactggg gccagatggt aagccctccc gtatcgtagt tatctacacg    6900
acggggagtc aggcaactat ggatgaacga atagacaga tcgctgagat aggtgcctca    6960
ctgattaagc attggtaact gtcagaccaa gtttactcat atatacttta gattgattta    7020
aaacttcatt tttaatttaa aaggatctag gtgaagatcc ttttttgataa tctcatgacc    7080 aaaatccctt aacgtgagtt ttcgttccac tgagcgtcag accccgtaga aaagatcaaa    7140
ggatcttctt gagatccttt ttttctgcgc gtaatctgct gcttgcaaac aaaaaaacca    7200
ccgctaccag cggtggtttg tttgccggat caagagctac caactctttt tccgaaggta    7260
actggcttca gcagagcgca gataccaaat actgtccttc tagtgtagcc gtagttaggc    7320
caccacttca agaactctgt agcaccgcct acatacctcg ctctgctaat cctgttacca    7380
gtggctgctg ccagtggcga taagtcgtgt cttaccgggt tggactcaag acgatagtta    7440
ccggataagg cgcagcggtc gggctgaacg ggggttcgt gcacacagcc cagcttggag    7500
cgaacgacct acaccgaact gagataccta cagcgtgagc attgagaaag cgccacgctt    7560
cccgaaggga gaaaggcgga caggtatccg gtaagcggca gggtcggaac aggagagcgc    7620
```

```
acgagggagc ttccaggggg aaacgcctgg tatctttata gtcctgtcgg gtttcgccac    7680
ctctgacttg agcgtcgatt tttgtgatgc tcgtcagggg ggcggagcct atggaaaaac    7740
gccagcaacg cggccttttt acggttcctg gccttttgct ggccttttgc tcacatgttc    7800
tttcctgcgt tatcccctga ttctgtggat aaccgtatta ccgcctttga gtgagctgat    7860
accgctcgcc gcagccgaac gaccgagcgc agcgagtcag tgagcgagga agcggaagag    7920
cgcccaatac gcaaaccgcc tctccccgcg cgttggccga ttcattaatg cagctggcac    7980
gacaggtttc ccgactggaa agcgggcagt gagcgcaacg caattaatgt gagttagctc    8040
actcattagg cacccaggc tttacacttt atgcttccgg ctcgtatgtt gtgtggaatt    8100
gtgagcggat aacaatttca cacaggaaac agctatgacc atgattacgc c            8151
```

<210> SEQ ID NO 39
<211> LENGTH: 8265
<212> TYPE: DNA
<213> ORGANISM: Artificial Sequence
<220> FEATURE:
<223> OTHER INFORMATION: CD44v6-4GS2-CAR.28Z NGFR MUTATED LONG (V6 NML)

<400> SEQUENCE: 39

```
aagctttgct cttaggagtt tcctaataca tcccaaactc aaatatataa agcatttgac      60
ttgttctatg ccctaggggg cggggggaag ctaagccagc ttttttttaac atttaaaatg    120 ttaattccat tttaaatgca cagatgtttt tatttcataa gggtttcaat gtgcatgaat    180
gctgcaatat tcctgttacc aaagctagta taaataaaaa tagataaacg tggaaattac    240
ttagagtttc tgtcattaac gtttccttcc tcagttgaca acataaatgc gctgctgagc    300
aagccagttt gcatctgtca ggatcaattt cccattatgc cagtcatatt aattactagt    360
caattagttg attttattt ttgacatata catgtgaatg aaagacccca cctgtaggtt    420
tggcaagcta gcttaagtaa cgccatttg caaggcatgg aaaaatacat aactgagaat    480
agaaaagttc agatcaaggt caggaacaga tggaacagct gaatatgggc caaacaggat    540
atctgtggta agcagttcct gccccggctc agggccaaga acagatggaa cagctgaata    600
tgggccaaac aggatatctg tggtaagcag ttcctgcccc ggctcagggc caagaacaga    660
tggtccccag atgcggtcca gccctcagca gtttctagag aaccatcaga tgtttccagg    720
gtgccccaag gacctgaaat gaccctgtgc cttatttgaa ctaaccaatc agttcgcttc    780
tcgcttctgt tcgcgcgctt atgctccccg agctcaataa aagagcccac aacccctcac    840
tcggggcgcc agtcctccga ttgactgagt cgcccgggta cccgtgtatc caataaaccc    900
tcttgcagtt gcatccgact tgtggtctcg ctgttccttg ggagggtctc ctctgagtga    960
ttgactaccc gtcagcgggg gtctttcatt tgggggctcg tccgggatcg ggagacccct   1020
gcccagggac caccgaccca ccacgggag gtaagctggc cagcaactta tctgtgtctg   1080
tccgattgtc tagtgtctat gactgatttt atgcgcctgc gtcggtacta gttagctaac   1140
tagctctgta tctggcggac ccgtggtgga actgacgagt tcggaacacc cggccgcaac   1200
cctgggagac gtcccaggga cttcggggggc cgttttgtg gcccgacctg agtcctaaaa   1260
tcccgatcgt ttaggactct ttggtgcacc cccttagag gagggatatg tggttctggt   1320
aggagacgag aacctaaaac agttcccgcc tccgtctgaa ttttttgcttt cggtttggga   1380 ccgaagccgc gccgcgcgtc ttgtctgctg cagcatcgtt ctgtgttgtc tctgtctgac   1440
tgtgtttctg tatttgtctg aaaatatggg cccgggctag cctgttacca ctcccttaag   1500
tttgacctta ggtcactgga agatgtcga gcggatcgct cacaaccagt cggtagatgt   1560
```

```
caagaagaga cgttgggtta ccttctgctc tgcagaatgg ccaaccttta acgtcggatg    1620
gccgcgagac ggcaccttta accgagacct catcacccag gttaagatca aggtcttttc    1680
acctggcccg catggacacc cagaccaggt ggggtacatc gtgacctggg aagccttggc    1740
ttttgacccc cctccctggg tcaagccctt tgtacaccct aagcctccgc ctcctcttcc    1800
tccatccgcc ccgtctctcc cccttgaacc tcctcgttcg accccgcctc gatcctccct    1860
ttatccagcc ctcactcctt ctctaggcgc cccatatgg ccatatgaga tcttatatgg     1920
ggcacccccg cccccttgtaa acttccctga ccctgacatg acaagagtta ctaacagccc    1980
ctctctccaa gctcacttac aggctctcta cttagtccag cacgaagtct ggagacctct    2040
ggcggcagcc taccaagaac aactggaccg accggtggta cctcacccct accgagtcgg    2100
cgacacagtg tgggtccgcc gacaccagac taagaaccta gaacctcgct ggaaaggacc    2160
ttacacagtc ctgctgacca cccccaccgc cctcaaagta gacggcatcg cagcttggat    2220
acacgccgcc cacgtgaagg ctgccgaccc cggggtgga ccatcctcta gactgccatg      2280
gaagcccctg cccagctgct gttcctgctg ctgctgtggc tgcccgacac caccggcgag    2340
atcgtgctga cacagagccc cgccacccctg tctctgagcc ctggcgagag agccacccctg   2400 agctgtagcg ccagcagcag catcaactac atctactggc tgcagcagaa gcccggccag    2460
gcccccagaa tcctgatcta cctgaccagc aacctggcca gcggcgtgcc cgccagattt    2520
tctggcagcg gcagcggcac cgacttcacc ctgaccatca gcagcctgga acccgaggac    2580
ttcgccgtgt actactgcct gcagtggtcc agcaaccccc tgaccttcgg cggaggcacc    2640
aaggtggaaa tcaagcgggg tggtggtggt tctggtggtg gtggttctga ggtgcagctg    2700
gtggaaagcg gcggaggcct ggtcaagcct ggcggcagcc tgagactgag ctgtgccgcc    2760
agcggcttca ccttcagcag ctacgacatg agctgggtcc gacaggctcc aggcaaggga    2820
ctggaatggg tgtccaccat cagcagcggc ggcagctaca cctactacct ggacagcatc    2880
aagggccggt tcaccatcag ccgggacaac gccaagaaca gcctgtacct gcagatgaac    2940
agcctgcggg ccgaggacac cgccgtctac tactgtgccc ggcagggcct cgactactgg    3000
ggcagaggca ccctggtcac cgtgtccagc ggggatccca aagaggcctg ccccaccggc    3060
ctgtacaccc acagcggaga gtgctgcaag gcctgcaacc tgggagaggg cgtggcccag    3120
ccttgcggcg ccaatcagac cgtgtgcgag ccctgcctgg acagcgtgac cttcagcgac    3180
gtggtgtccg ccaccgagcc ctgcaagcct tgcaccgagt gtgtgggcct gcagagcatg    3240
agcgccccct gcgtggaagc cgacgacgcc gtgtgtagat gcgcctacgg ctactaccag    3300
gacgagacaa ccggcagatg cgaggcctgt agagtgtgcg aggccggcag cggcctggtg    3360
ttcagttgtc aagacaagca gaataccgtg tgtgaagagt gccccgacgg cacctacagc    3420
gacgaagccg ccagagccgc cgacgccgag tgcgaagaga tccccggcag atggatcacc    3480
agaagcaccc cccctgaggg cagcgacagc accgccccta gcacccagga acctgaggcc    3540
cctcccgagc aggacctgat cgcctctaca gtggccggcg tggtgacaac cgtgatgggc    3600
agctctcagc ccgtggtgac acggggcacc accgacaatc ccaaattttg ggtgctggtg    3660
gtggttggtg gagtcctggc ttgctatagc ttgctagtaa cagtggcctt tattattttc    3720
tgggtgagga gtaagaggag caggctcctg cacagtgact acatgaacat gactccccgc    3780
cgccccgggc ccacccgcaa gcattaccag ccctatgccc caccacgcga cttcgcagcc    3840
tatcgctcca gagtgaagtt cagcaggagc gcagacgccc ccgcgtacca gcagggccag    3900
```

```
aaccagctct ataacgagct caatctagga cgaagagagg agtacgatgt tttggacaag    3960
agacgtggcc gggaccctga gatgggggga aagccgagaa ggaagaaccc tcaggaaggc    4020
ctgtacaatg aactgcagaa agataagatg gcggaggcct acagtgagat tgggatgaaa    4080
ggcgagcgcc ggaggggcaa ggggcacgat ggcctttacc agggtctcag tacagccacc    4140
aaggacacct acgacgccct tcacatgcag gccctgcctc ctcgctaagc atgcaacctc    4200
gatccggatt agtccaattt gttaaagaca ggatatcagt ggtccaggct ctagttttga    4260
ctcaacaata tcaccagctg aagcctatag agtacgagcc atagataaaa taaaagattt    4320
tatttagtct ccagaaaaag gggggaatga agacccccac ctgtaggttt ggcaagctag    4380
cttaagtaac gccattttgc aaggcatgga aaatacata actgagaata gagaagttca    4440
gatcaaggtc aggaacagat ggaacagctg aatatgggcc aaacaggata tctgtggtaa    4500
gcagttcctg ccccggctca gggccaagaa cagatggaac agctgaatat gggccaaaca    4560
ggatatctgt ggtaagcagt tcctgccccg gctcagggcc aagaacagat ggtccccaga    4620
tgcggtccag ccctcagcag tttctagaga accatcagat gtttccaggg tgccccaagg    4680
acctgaaatg accctgtgcc ttatttgaac taaccaatca gttcgcttct cgcttctgtt    4740
cgcgcgcttc tgctccccga gctcaataaa agagcccaca cccctcact cggggcgcca    4800 gtcctccgat tgactgagtc gcccgggtac ccgtgtatcc aataaaccct cttgcagttg    4860
catccgactt gtggtctcgc tgttccttgg gagggtctcc tctgagtgat tgactacccg    4920
tcagcggggg tctttcacac atgcagcatg tatcaaaatt aatttggttt tttttcttaa    4980
gtatttacat taaatggcca tagtacttaa agttacattg gcttccttga aataaacatg    5040
gagtattcag aatgtgtcat aaatatttct aattttaaga tagtatctcc attggctttc    5100
tactttttct tttattttt tttgtcctct gtcttccatt tgttgttgtt gttgtttgtt    5160
tgtttgtttg ttggttggtt ggttaatttt tttttaaaga tcctacacta tagttcaagc    5220
tagactatta gctactctgt aacccagggt gaccttgaag tcatgggtag cctgctgttt    5280
tagccttccc acatctaaga ttacaggtat gagctatcat ttttggtata ttgattgatt    5340
gattgattga tgtgtgtgtg tgtgattgtg tttgtgtgtg tgactgtgaa aatgtgtgta    5400
tgggtgtgtg tgaatgtgtg tatgtatgtg tgtgtgtgag tgtgtgtgtg tgtgtgtgca    5460
tgtgtgtgtg tgtgactgtg tctatgtgta tgactgtgtg tgtgtgtgtg tgtgtgtgtg    5520
tgtgtgtgtg tgtgtgtgtg ttgtgaaaaa atattctatg gtagtgagag ccaacgctcc    5580
ggctcaggtg tcaggttggt ttttgagaca gagtctttca cttagcttgg aattcactgg    5640
ccgtcgtttt acaacgtcgt gactgggaaa accctggcgt tacccaactt aatcgccttg    5700
cagcacatcc ccctttcgcc agctggcgta atagcgaaga ggcccgcacc gatcgccctt    5760
cccaacagtt gcgcagcctg aatggcgaat ggcgcctgat gcggtatttt ctccttacgc    5820
atctgtgcgg tatttcacac cgcatatggt gcactctcag tacaatctgc tctgatgccg    5880
catagttaag ccagccccga cacccgccaa cacccgctga cgcgccctga cgggcttgtc    5940
tgctcccggc atccgcttac agacaagctg tgaccgtctc cgggagctgc atgtgtcaga    6000
ggttttcacc gtcatcaccg aaacgcgcga tgacgaaagg gcctcgtgat acgcctattt    6060
ttataggtta atgtcatgat aataatggtt tcttagacgt caggtggcac ttttcgggga    6120
aatgtgcgcg gaacccctat ttgtttattt ttctaaatac attcaaatat gtatccgctc    6180
atgagacaat aaccctgata aatgcttcaa taatattgaa aaaggaagag tatgagtatt    6240
caacatttcc gtgtcgccct tattccctttt tttgcggcat tttgccttcc tgtttttgct    6300
```

```
cacccagaaa cgctggtgaa agtaaaagat gctgaagatc agttgggtgc acgagtgggt    6360
tacatcgaac tggatctcaa cagcggtaag atccttgaga gttttcgccc cgaagaacgt    6420
tttccaatga tgagcacttt taaagttctg ctatgtggcg cggtattatc ccgtattgac    6480
gccgggcaag agcaactcgg tcgccgcata cactattctc agaatgactt ggttgagtac    6540
tcaccagtca cagaaaagca tcttacggat ggcatgacag taagagaatt atgcagtgct    6600
gccataacca tgagtgataa cactgcggcc aacttacttc tgacaacgat cggaggaccg    6660
aaggagctaa ccgcttttt gcacaacatg ggggatcatg taactcgcct tgatcgttgg    6720
gaaccggagc tgaatgaagc cataccaaac gacgagcgtg acaccacgat gcctgtagca    6780
atggcaacaa cgttgcgcaa actattaact ggcgaactac ttactctagc ttcccggcaa    6840
caattaatag actggatgga ggcggataaa gttgcaggac cacttctgcg ctcggccctt    6900
ccggctggct ggtttattgc tgataaatct ggagccggtg agcgtgggtc tcgcggtatc    6960
attgcagcac tggggccaga tggtaagccc tcccgtatcg tagttatcta cacgacgggg    7020
agtcaggcaa ctatggatga acgaaataga cagatcgctg agataggtgc ctcactgatt    7080
aagcattggt aactgtcaga ccaagtttac tcatatatac tttagattga tttaaaactt    7140
catttttaat ttaaaaggat ctaggtgaag atcctttttg ataatctcat gaccaaaatc    7200
ccttaacgtg agttttcgtt ccactgagcg tcagaccccg tagaaaagat caaaggatct    7260
tcttgagatc ctttttttct gcgcgtaatc tgctgcttgc aaacaaaaaa accaccgcta    7320
ccagcggtgg tttgtttgcc ggatcaagag ctaccaactc tttttccgaa ggtaactggc    7380
ttcagcagag cgcagatacc aaatactgtc cttctagtgt agccgtagtt aggccaccac    7440
ttcaagaact ctgtagcacc gcctacatac ctcgctctgc taatcctgtt accagtggct    7500
gctgccagtg gcgataagtc gtgtcttacc gggttggact caagacgata gttaccggat    7560
aaggcgcagc ggtcgggctg aacggggggt tcgtgcacac agcccagctt ggagcgaacg    7620
acctacaccg aactgagata cctacagcgt gagcattgag aaagcgccac gcttcccgaa    7680
gggagaaagg cggacaggta tccggtaagc ggcagggtcg gaacaggaga gcgcacgagg    7740
gagcttccag ggggaaacgc ctggtatctt tatagtcctg tcgggtttcg ccacctctga    7800
cttgagcgtc gatttttgtg atgctcgtca gggggcgga gcctatggaa aaacgccagc    7860
aacgcggcct ttttacggtt cctggccttt tgctggcctt ttgctcacat gttctttcct    7920
gcgttatccc ctgattctgt ggataaccgt attaccgcct ttgagtgagc tgataccgct    7980
cgccgcagcc gaacgaccga gcgcagcgag tcagtgagcg aggaagcgga agagcgccca    8040
atacgcaaac cgcctctccc cgcgcgttgg ccgattcatt aatgcagctg gcacgacagg    8100
tttcccgact ggaaagcggg cagtgagcgc aacgcaatta atgtgagtta gctcactcat    8160
taggcacccc aggctttaca ctttatgctt ccggctcgta tgttgtgtgg aattgtgagc    8220
ggataacaat ttcacacagg aaacagctat gaccatgatt acgcc              8265
```

<210> SEQ ID NO 40
<211> LENGTH: 8085
<212> TYPE: DNA
<213> ORGANISM: Artificial Sequence
<220> FEATURE:
<223> OTHER INFORMATION: CD44v6-4GS2-CAR.28Z NGFR MUTATED SHORT (V6 NMS)

<400> SEQUENCE: 40

```
aagctttgct cttaggagtt tcctaataca tcccaaactc aaatatataa agcatttgac      60
```

| | |
|---|---|
| ttgttctatg cccctagggggg cgggggggaag ctaagccagc ttttttttaac atttaaaatg | 120 |
| ttaattccat tttaaatgca cagatgtttt tatttcataa gggtttcaat gtgcatgaat | 180 |
| gctgcaatat tcctgttacc aaagctagta taaataaaaa tagataaacg tggaaattac | 240 |
| ttagagtttc tgtcattaac gtttccttcc tcagttgaca acataaatgc gctgctgagc | 300 |
| aagccagttt gcatctgtca ggatcaattt cccattatgc cagtcatatt aattactagt | 360 |
| caattagttg atttttatttt ttgacatata catgtgaatg aaagacccca cctgtaggtt | 420 |
| tggcaagcta gcttaagtaa cgccattttg caaggcatgg aaaaatacat aactgagaat | 480 |
| agaaaagttc agatcaaggt caggaacaga tggaacagct gaatatgggc caaacaggat | 540 |
| atctgtggta agcagttcct gccccggctc agggccaaga acagatggaa cagctgaata | 600 |
| tgggccaaac aggatatctg tggtaagcag ttcctgcccc ggctcagggc caagaacaga | 660 |
| tggtccccag atgcggtcca gccctcagca gtttctagag aaccatcaga tgtttccagg | 720 |
| gtgcccaag gacctgaaat gaccctgtgc cttatttgaa ctaaccaatc agttcgcttc | 780 |
| tcgcttctgt tcgcgcgctt atgctccccg agctcaataa aagagcccac aacccctcac | 840 |
| tcggggcgcc agtcctccga ttgactgagt cgcccgggta cccgtgtatc caataaaccc | 900 |
| tcttgcagtt gcatccgact tgtggtctcg ctgttccttg ggagggtctc ctctgagtga | 960 |
| ttgactaccc gtcagcgggg gtctttcatt tggggggctcg tccgggatcg ggagacccct | 1020 |
| gcccagggac caccgaccca ccaccgggag gtaagctggc cagcaactta tctgtgtctg | 1080 |
| tccgattgtc tagtgtctat gactgatttt atgcgcctgc gtcggtacta gttagctaac | 1140 |
| tagctctgta tctggcggac ccgtggtgga actgacgagt tcggaacacc cggccgcaac | 1200 |
| cctgggagac gtcccaggga cttcgggggc cgttttttgtg gcccgacctg agtcctaaaa | 1260 |
| tcccgatcgt ttaggactct ttggtgcacc ccccttagag gagggatatg tggttctggt | 1320 |
| aggagacgag aacctaaaac agttcccgcc tccgtctgaa ttttttgcttt cggtttggga | 1380 |
| ccgaagccgc gccgcgcgtc ttgtctgctg cagcatcgtt ctgtgttgtc tctgtctgac | 1440 |
| tgtgtttctg tatttgtctg aaaatatggg cccgggctag cctgttacca ctcccttaag | 1500 |
| tttgaccctta ggtcactgga aagatgtcga gcggatcgct cacaaccagt cggtagatgt | 1560 |
| caagaagaga cgttgggtta ccttctgctc tgcagaatgg ccaaccttta acgtcggatg | 1620 |
| gccgcgagac ggcacctttta accgagacct catcacccag gttaagatca aggtcttttc | 1680 |
| acctggcccg catggacacc cagaccaggt ggggtacatc gtgacctggg aagccttggc | 1740 |
| ttttgacccc cctccctggg tcaagccctt tgtacaccct aagcctccgc ctcctcttcc | 1800 |
| tccatccgcc ccgtctctcc cccttgaacc tcctcgttcg accccgcctc gatcctccct | 1860 |
| ttatccagcc ctcactcctt ctctaggcgc cccccatatgg ccatatgaga tcttatatgg | 1920 |
| ggcacccccg cccccttgtaa acttccctga ccctgacatg acaagagtta ctaacagccc | 1980 |
| ctctctccaa gctcacttac aggctctcta cttagtccag cacgaagtct ggagacctct | 2040 |
| ggcggcagcc taccaagaac aactggaccg accggtggta cctcacccctt accgagtcgg | 2100 |
| cgacacagtg tgggtccgcc gacaccagac taagaaccta gaacctcgct ggaaaggacc | 2160 |
| ttacacagtc ctgctgacca cccccaccgc cctcaaagta gacggcatcg cagcttggat | 2220 |
| acacgccgcc cacgtgaagg ctgccgaccc cggggggtgga ccatcctcta gactgccatg | 2280 |
| gaagcccctg cccagctgct gttcctgctg ctgctgtggc tgcccgacac caccggcgag | 2340 |
| atcgtgctga cacagagccc cgccaccctg tctctgagcc ctggcgagag agccaccctg | 2400 |
| agctgtagcg ccagcagcag catcaactac atctactggc tgcagcagaa gcccggccag | 2460 |

-continued

```
gcccccagaa tcctgatcta cctgaccagc aacctggcca gcggcgtgcc cgccagattt    2520
tctggcagcg gcagcggcac cgacttcacc ctgaccatca gcagcctgga acccgaggac    2580
ttcgccgtgt actactgcct gcagtggtcc agcaacccCC tgaccttcgg cggaggcacc    2640
aaggtggaaa tcaagcgggg tggtggtggt tctggtggtg gtggttctga ggtgcagctg    2700
gtggaaagcg gcggaggcct ggtcaagcct ggcggcagcc tgagactgag ctgtgccgcc    2760
agcggcttca ccttcagcag ctacgacatg agctgggtcc acaggctcc aggcaaggga    2820
ctggaatggg tgtccaccat cagcagcggc ggcagctaca cctactacct ggacagcatc    2880
aagggccggt tcaccatcag ccgggacaac gccaagaaca ccctgtacct gcagatgaac    2940
agcctgcggg ccgaggacac cgccgtctac tactgtgccc ggcagggcct cgactactgg    3000
ggcagaggca ccctggtcac cgtgtccagc ggggatccca agaggcctg ccccaccggc    3060
ctgtacaccc acagcggaga gtgctgcaag gcctgcaacc tgggagaggg cgtggcccag    3120
ccttgcggcg ccaatcagac cgtgtgcgag ccctgcctgg acagcgtgac cttcagcgac    3180
gtggtgtccg ccaccgagcc ctgcaagcct tgcaccgagt gtgtgggcct gcagagcatg    3240
agcgcccct gcgtggaagc cgacgacgcc gtgtgtagat cgcctacgg ctactaccag    3300
gacgagacaa ccggcagatg cgaggcctgt agagtgtgcg aggccggcag cggcctggtg    3360
ttcagttgtc aggacaagca gaacaccgtg tgtgaagagt gccccgacgg cacctacagc    3420
gacgaggccg cccgggccgc cgacgccgag tgcgaggaac ccaaattttg ggtgctggtg    3480
gtggttggtg gagtcctggc ttgctatagc ttgctagtaa cagtggcctt tattattttc    3540
tgggtgagga gtaagaggag caggctcctg cacagtgact acatgaacat gactccccgc    3600
cgccccgggc ccaccccaa gcattaccag ccctatgccc caccacgcga cttcgcagcc    3660
tatcgctcca gagtgaagtt cagcaggagc gcagacgccc ccgcgtacca gcagggccag    3720
aaccagctct ataacgagct caatctagga cgaagagagg agtacgatgt tttggacaag    3780
agacgtggcc gggaccctga gatgggggga aagccgagaa ggaagaaccc tcaggaaggc    3840
ctgtacaatg aactgcagaa agataagatg gcggaggcct acagtgagat tgggatgaaa    3900
ggcgagcgcc ggaggggcaa ggggcacgat ggcctttacc agggtctcag tacagccacc    3960
aaggacacct acgacgccct tcacatgcag gccctgcctc ctcgctaagc atgcaacctc    4020
gatccggatt agtccaattt gttaaagaca ggatatcagt ggtccaggct ctagttttga    4080
ctcaacaata tcaccagctg aagcctatag agtacgagcc atagataaaa taaaagattt    4140
tatttagtct ccagaaaaag gggggaatga agacccccac ctgtaggttt ggcaagctag    4200
cttaagtaac gccattttgc aaggcatgga aaatacata actgagaata gagaagttca    4260
gatcaaggtc aggaacagat ggaacagctg aatatgggcc aaacaggata tctgtggtaa    4320
gcagttcctg ccccggctca gggccaagaa cagatggaac agctgaatat gggccaaaca    4380
ggatatctgt ggtaagcagt tcctgccccg gctcagggcc aagaacagat ggtccccaga    4440
tgcggtccag ccctcagcag tttctagaga accatcagat gtttccaggg tgccccaagg    4500
acctgaaatg accctgtgcc ttatttgaac taaccaatca gttcgcttct cgcttctgtt    4560
cgcgcgcttc tgctccccga gctcaataaa agagcccaca cccctcact cggggcgcca    4620
gtcctccgat tgactgagtc gcccgggtac ccgtgtatcc aataaaccct cttgcagttg    4680
catccgactt gtggtctcgc tgttccttgg gagggtctcc tctgagtgat tgactacccg    4740
tcagcggggg tctttcacac atgcagcatg tatcaaaatt aatttggttt tttttcttaa    4800
```

```
gtatttacat taaatggcca tagtacttaa agttacattg gcttccttga aataaacatg    4860
gagtattcag aatgtgtcat aaatatttct aatttttaaga tagtatctcc attggctttc    4920 tacttttttct tttattttttt tttgtcctct gtcttccatt tgttgttgtt gttgtttgtt    4980
tgtttgtttg ttggttggtt ggttaatttt ttttttaaaga tcctacacta tagttcaagc    5040
tagactatta gctactctgt aacccagggt gaccttgaag tcatgggtag cctgctgttt    5100
tagccttccc acatctaaga ttacaggtat gagctatcat ttttggtata ttgattgatt    5160
gattgattga tgtgtgtgtg tgtgattgtg tttgtgtgtg tgactgtgaa aatgtgtgta    5220
tgggtgtgtg tgaatgtgtg tatgtatgtg tgtgtgtgag tgtgtgtgtg tgtgtgtgca    5280
tgtgtgtgtg tgtgactgtg tctatgtgta tgactgtgtg tgtgtgtgtg tgtgtgtgtg    5340
tgtgtgtgtg tgtgtgtgtg ttgtgaaaaa atattctatg gtagtgagag ccaacgctcc    5400
ggctcaggtg tcaggttggt ttttgagaca gagtctttca cttagcttgg aattcactgg    5460
ccgtcgtttt acaacgtcgt gactgggaaa accctggcgt tacccaactt aatcgccttg    5520
cagcacatcc cccttttcgcc agctggcgta atagcgaaga ggcccgcacc gatcgccctt    5580
cccaacagtt gcgcagcctg aatggcgaat ggcgcctgat gcggtatttt ctccttacgc    5640
atctgtgcgg tatttcacac cgcatatggt gcactctcag tacaatctgc tctgatgccg    5700
catagttaag ccagccccga cacccgccaa cacccgctga cgcgccctga cgggcttgtc    5760
tgctcccggc atccgcttac agacaagctg tgaccgtctc cgggagctgc atgtgtcaga    5820
ggttttcacc gtcatcaccg aaacgcgcga tgacgaaagg gcctcgtgat acgcctattt    5880
ttataggtta atgtcatgat aataatggtt tcttagacgt caggtggcac ttttcgggga    5940
aatgtgcgcg gaacccctat ttgtttattt ttctaaatac attcaaatat gtatccgctc    6000
atgagacaat aaccctgata aatgcttcaa taatattgaa aaaggaagag tatgagtatt    6060
caacatttcc gtgtcgccct tattcccttt tttgcggcat tttgccttcc tgtttttgct    6120
cacccagaaa cgctggtgaa agtaaaagat gctgaagatc agttgggtgc acgagtgggt    6180
tacatcgaac tggatctcaa cagcggtaag atccttgaga gttttcgccc cgaagaacgt    6240
tttccaatga tgagcacttt taaagttctg ctatgtggcg cggtattatc ccgtattgac    6300
gccgggcaag agcaactcgg tcgccgcata cactattctc agaatgactt ggttgagtac    6360
tcaccagtca cagaaaagca tcttacggat ggcatgacag taagagaatt atgcagtgct    6420
gccataacca tgagtgataa cactgcggcc aacttacttc tgacaacgat cggaggaccg    6480
aaggagctaa ccgcttttttt gcacaacatg ggggatcatg taactcgcct tgatcgttgg    6540
gaaccggagc tgaatgaagc cataccaaac gacgagcgtg acaccacgat gcctgtagca    6600
atggcaacaa cgttgcgcaa actattaact ggcgaactac ttactctagc ttcccggcaa    6660
caattaatag actggatgga ggcggataaa gttgcaggac cacttctgcg ctcggccctt    6720
ccggctggct ggtttattgc tgataaatct ggagccggtg agcgtgggtc tcgcggtatc    6780
attgcagcac tggggccaga tggtaagccc tcccgtatcg tagttatcta cacgacgggg    6840
agtcaggcaa ctatggatga acgaaataga cagatcgctg agataggtgc ctcactgatt    6900
aagcattggt aactgtcaga ccaagtttac tcatatatac tttagattga tttaaaactt    6960
catttttaat ttaaaaggat ctaggtgaag atcctttttg ataatctcat gaccaaaatc    7020
ccttaacgtg agttttcgtt ccactgagcg tcagaccccg tagaaaagat caaaggatct    7080
tcttgagatc cttttttttct gcgcgtaatc tgctgcttgc aaacaaaaaa accaccgcta    7140
ccagcggtgg tttgtttgcc ggatcaagag ctaccaactc tttttccgaa ggtaactggc    7200
```

```
ttcagcagag cgcagatacc aaatactgtc cttctagtgt agccgtagtt aggccaccac    7260
ttcaagaact ctgtagcacc gcctacatac ctcgctctgc taatcctgtt accagtggct    7320
gctgccagtg gcgataagtc gtgtcttacc gggttggact caagacgata gttaccggat    7380
aaggcgcagc ggtcgggctg aacgggggt tcgtgcacac agcccagctt ggagcgaacg     7440
acctacaccg aactgagata cctacagcgt gagcattgag aaagcgccac gcttcccgaa    7500
gggagaaagg cggacaggta tccggtaagc ggcagggtcg gaacaggaga gcgcacgagg    7560
gagcttccag ggggaaacgc ctggtatctt tatagtcctg tcgggtttcg ccacctctga    7620
cttgagcgtc gattttgtg atgctcgtca gggggcgga gcctatggaa aaacgccagc      7680
aacgcggcct ttttacggtt cctggccttt tgctggcctt ttgctcacat gttctttcct    7740
gcgttatccc ctgattctgt ggataaccgt attaccgcct ttgagtgagc tgataccgct    7800
cgccgcagcc gaacgaccga gcgcagcgag tcagtgagcg aggaagcgga agagcgccca    7860
atacgcaaac cgcctctccc cgcgcgttgg ccgattcatt aatgcagctg gcacgacagg    7920
tttcccgact ggaaagcggg cagtgagcgc aacgcaatta atgtgagtta gctcactcat    7980
taggcacccc aggctttaca ctttatgctt ccggctcgta tgttgtgtgg aattgtgagc    8040
ggataacaat ttcacacagg aaacagctat gaccatgatt acgcc                    8085
```